United States Patent
Norris et al.

(10) Patent No.: US 7,575,918 B2
(45) Date of Patent: Aug. 18, 2009

(54) TISSUE-SPECIFIC AND PATHOGEN-SPECIFIC RIBOZYMES

(75) Inventors: James Norris, Mt. Pleasant, SC (US); Gary Clawson, Bethesda, MD (US); Caroline Westwater, Mt. Pleasant, SC (US); David Schofield, Mt. Pleasant, SC (US); Michael G. Schmidt, Charleston, SC (US); Brian Hoel, Charleston, SC (US); Joseph Dolan, Mt. Pleasant, SC (US); Wei-Hua Pan, Hummelstown, PA (US)

(73) Assignee: The Penn State Research Foundation, University Park, PA (US)

(*) Notice: Subject to any disclaimer, the term of this patent is extended or adjusted under 35 U.S.C. 154(b) by 0 days.

(21) Appl. No.: 10/935,962

(22) Filed: Sep. 8, 2004

(65) Prior Publication Data

US 2005/0107326 A1 May 19, 2005

Related U.S. Application Data

(63) Continuation of application No. 09/548,449, filed on Apr. 13, 2000, now abandoned, which is a continuation-in-part of application No. 09/291,902, filed on Apr. 14, 1999, now Pat. No. 6,271,359.

(51) Int. Cl.
C07H 21/04 (2006.01)
C07H 21/02 (2006.01)
C12Q 1/68 (2006.01)
A61K 31/70 (2006.01)

(52) U.S. Cl. .................. 435/320.1; 435/6; 536/23.1; 536/24.1; 536/24.5; 514/44

(58) Field of Classification Search .................. None
See application file for complete search history.

(56) References Cited

U.S. PATENT DOCUMENTS

| | | | |
|---|---|---|---|
| 4,511,713 A | 4/1985 | Miller et al. |
| 4,560,678 A | 12/1985 | Ranson |
| 4,683,195 A | 7/1987 | Mullis et al. |
| 4,740,463 A | 4/1988 | Weinberg et al. |
| 4,814,268 A | 3/1989 | Kreider et al. |
| 4,849,331 A | 7/1989 | Lorincz |
| 4,849,332 A | 7/1989 | Lorincz |
| 4,849,334 A | 7/1989 | Lorincz |
| 4,873,191 A | 10/1989 | Wagner et al. |
| 4,908,306 A | 3/1990 | Lorincz |
| 4,983,728 A | 1/1991 | Herzog et al. |
| 5,023,243 A | 6/1991 | Tullis |
| 5,057,411 A | 10/1991 | Lancaster et al. |
| 5,071,757 A | 12/1991 | Kreider et al. |
| 5,126,331 A | 6/1992 | Gazzani |
| 5,142,032 A | 8/1992 | Grimmel et al. |
| 5,166,057 A | 11/1992 | Palese et al. |
| 5,187,090 A | 2/1993 | de Villiers et al. |
| 5,190,931 A | 3/1993 | Inouye |
| 5,254,678 A | 10/1993 | Haseloff et al. |
| 5,272,065 A | 12/1993 | Inouye et al. |
| 5,294,533 A | 3/1994 | Lupski et al. |
| 5,334,761 A | 8/1994 | Gebeyehu et al. |
| 5,411,857 A | 5/1995 | Beaudenon et al. |
| 5,436,330 A | 7/1995 | Taira et al. |
| 5,457,189 A | 10/1995 | Crooke et al. |
| 5,491,133 A | 2/1996 | Walder et al. |
| 5,494,814 A | 2/1996 | Haseloff et al. |
| 5,496,698 A | 3/1996 | Draper et al. |
| 5,500,357 A * | 3/1996 | Taira et al. ............... 435/91.31 |
| 5,501,947 A | 3/1996 | Emery et al. |
| 5,525,468 A | 6/1996 | McSwiggen |
| 5,543,508 A | 8/1996 | Haseloff et al. |
| 5,554,538 A | 9/1996 | Cole et al. |
| 5,574,143 A | 11/1996 | Haseloff et al. |

(Continued)

FOREIGN PATENT DOCUMENTS

AU  611135  6/1991

(Continued)

OTHER PUBLICATIONS

Lu et al. Cancer Gene Therapy, vol. 1(4)267-277, 1994.*

(Continued)

*Primary Examiner*—Sean R McGarry
(74) *Attorney, Agent, or Firm*—Fish & Richardson P.C.

(57) ABSTRACT

The present invention relates to the discovery, identification and characterization of toxic agents which are lethal to pathogens and methods for targeting such toxic agents to a pathogen or pathogen infected cells in order to treat and/or eradicate the infection. In particular, the present invention relates to toxic agents which target bacteria at different stages of the bacterial life cycle, which are delivered alone or in combination to bacteria or bacteria-infected cells. The invention relates to toxic agents which are lethal to diseased cells and methods for targeting such toxic agents to a diseased cell in order to treat and/or eradicate the disease. The present invention relates to promoter elements which are pathogen-specific or tissue-specific and the use of such promoter elements to achieve pathogen-specific or tissue-specific expression of the toxic agent(s) and/or ribozyme(s) of the present invention. Specifically, the invention relates to the delivery of one or more toxic gene products, antisense RNAs, or ribozymes, or combination thereof. The invention provides a novel system by which multiple pathogenic targets may be simultaneously targeted to cause the death of a pathogen, or cell infected with a pathogen. Further, the invention has important implications in the eradication of drug-resistant bacterium and bacterial pathogens. The invention provides a novel system by which multiple targets may be simultaneously targeted to cause the death of a diseased cell. The invention has important implications in the eradication of drug-resistant pathogens (such as antibiotic resistant bacteria) and drug-resistant diseased cells (such as drug-resistant cancer cells).

10 Claims, 23 Drawing Sheets

U.S. PATENT DOCUMENTS

Figures 1A, 1B, 1C:
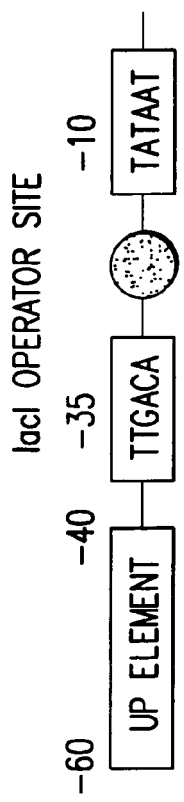

| | | | |
|---|---|---|---|
| 5,578,473 A | 11/1996 | Palese et al. | |
| 5,580,547 A | 12/1996 | Gilchrest et al. | |
| 5,580,859 A | 12/1996 | Felgner et al. | |
| 5,589,466 A | 12/1996 | Felgner et al. | |
| 5,589,580 A | 12/1996 | Haseloff et al. | |
| 5,591,574 A | 1/1997 | Orth et al. | |
| 5,595,884 A | 1/1997 | Androphy et al. | |
| 5,610,054 A | 3/1997 | Draper | |
| 5,622,854 A | 4/1997 | Draper | |
| 5,631,360 A | 5/1997 | Usman et al. | |
| 5,635,385 A | 6/1997 | Leopold et al. | |
| 5,643,715 A | 7/1997 | Lancaster | |
| 5,646,020 A | 7/1997 | Swiggen et al. | |
| 5,656,423 A | 8/1997 | Orth et al. | |
| 5,665,580 A | 9/1997 | Crooke et al. | |
| 5,670,488 A | 9/1997 | Gregory et al. | |
| 5,674,835 A | 10/1997 | Androphy et al. | |
| 5,681,944 A | 10/1997 | Crooke et al. | |
| 5,683,902 A * | 11/1997 | Hampel et al. | 435/325 |
| 5,686,599 A | 11/1997 | Tracz | |
| 5,693,535 A | 12/1997 | Draper et al. | |
| 5,712,092 A | 1/1998 | Orth et al. | |
| 5,739,013 A | 4/1998 | Budowsky et al. | |
| 5,756,282 A | 5/1998 | Crooke et al. | |
| 5,767,263 A | 6/1998 | Usman et al. | |
| 5,776,502 A | 7/1998 | Foulkes et al. | |
| 5,795,778 A | 8/1998 | Draper | |
| 5,804,683 A | 9/1998 | Usman et al. | |
| 5,807,718 A | 9/1998 | Joyce et al. | |
| 5,811,232 A | 9/1998 | Crooke et al. | |
| 5,821,050 A | 10/1998 | Cowsert et al. | |
| 5,831,071 A | 11/1998 | Usman et al. | |
| 5,837,856 A | 11/1998 | Arnold, Jr. et al. | |
| 5,869,253 A | 2/1999 | Draper | |
| 5,876,922 A | 3/1999 | Orth et al. | |
| 5,879,938 A | 3/1999 | Usman et al. | |
| 5,891,684 A | 4/1999 | Usman et al. | |
| 5,912,149 A | 6/1999 | Ruiz et al. | |
| 5,952,487 A | 9/1999 | Philipp et al. | |
| 5,955,597 A | 9/1999 | Arnold, Jr. et al. | |
| 5,962,425 A | 10/1999 | Walder et al. | |
| 5,972,699 A | 10/1999 | Draper | |
| 5,977,343 A | 11/1999 | Tracz | |
| 5,981,173 A | 11/1999 | Orth et al. | |
| 5,986,083 A | 11/1999 | Dwyer et al. | |
| 6,004,513 A | 12/1999 | Albagli et al. | |
| 6,015,694 A | 1/2000 | Dubensky, Jr. et al. | |
| 6,017,756 A | 1/2000 | Draper | |
| 6,022,863 A | 2/2000 | Peyman | |
| 6,025,163 A | 2/2000 | Shamanin et al. | |
| 6,028,188 A | 2/2000 | Arnold, Jr. et al. | |
| 6,060,456 A | 5/2000 | Arnold, Jr. et al. | |
| 6,083,695 A | 7/2000 | Hardin et al. | |
| 6,084,090 A | 7/2000 | DiPaolo et al. | |
| 6,087,164 A * | 7/2000 | Hochberg et al. | 435/320.1 |
| 6,087,341 A | 7/2000 | Khavari et al. | |
| 6,127,164 A | 10/2000 | deVilliers et al. | |
| 6,132,966 A | 10/2000 | Draper | |
| 6,136,332 A | 10/2000 | Grollier et al. | |
| 6,159,692 A | 12/2000 | Draper et al. | |
| 6,172,048 B1 | 1/2001 | Behr et al. | |
| 6,174,870 B1 | 1/2001 | Crooke et al. | |
| 6,258,585 B1 | 7/2001 | Draper | |
| 6,271,359 B1 | 8/2001 | Norris et al. | |
| 6,277,980 B1 * | 8/2001 | DiPaolo et al. | 536/24.5 |
| 6,326,174 B1 | 12/2001 | Joyce et al. | |
| 6,353,098 B1 | 3/2002 | Usman et al. | |
| 6,432,704 B1 | 8/2002 | Draper | |
| 6,437,117 B1 | 8/2002 | Usman et al. | |
| 6,440,719 B1 | 8/2002 | Draper | |
| 6,469,158 B1 | 10/2002 | Usman | |
| 6,506,559 B1 | 1/2003 | Fire et al. | |
| 6,632,641 B1 * | 10/2003 | Brennan et al. | 435/91.2 |
| 2001/0006801 A1 | 7/2001 | Usman et al. | |
| 2002/0160393 A1 | 10/2002 | Symonds et al. | |
| 2003/0068301 A1 | 4/2003 | Draper et al. | |
| 2003/0088087 A1 | 5/2003 | Usman et al. | |
| 2003/0125280 A1 | 7/2003 | Norris et al. | |
| 2003/0166896 A1 | 9/2003 | Usman et al. | |
| 2003/0166917 A1 | 9/2003 | Usman et al. | |
| 2003/0206887 A1 | 11/2003 | Morrissey et al. | |
| 2004/0054156 A1 | 3/2004 | Draper et al. | |
| 2004/0127446 A1 | 7/2004 | Blatt et al. | |

FOREIGN PATENT DOCUMENTS

| | | |
|---|---|---|
| AU | 632993 | 1/1993 |
| AU | 687736 | 3/1998 |
| AU | 728732 | 1/2001 |
| AU | 743119 | 1/2002 |
| CA | 2002776 | 5/1990 |
| CA | 2142181 | 2/1994 |
| CA | 2236998 | 5/1997 |
| CA | 2274584 | 6/1998 |
| DE | 3838269 | 5/1990 |
| DE | 44 24 762 | 7/1995 |
| DE | 4424762 | 7/1995 |
| DE | 69126027 | 6/1997 |
| EP | 0301968 | 2/1989 |
| EP | 0321201 | 6/1989 |
| EP | 0334694 | 9/1989 |
| EP | 0357611 | 3/1990 |
| EP | 0373352 | 6/1990 |
| EP | 0402132 | 12/1990 |
| EP | 0433396 | 6/1991 |
| EP | 477972 | 4/1992 |
| EP | 0539461 | 5/1993 |
| EP | 0 640 688 | 3/1995 |
| EP | 0642589 | 3/1995 |
| EP | 0656060 | 6/1995 |
| EP | 792375 | 9/1997 |
| EP | 0866852 | 9/1998 |
| EP | 0943005 | 9/1999 |
| EP | 1288296 | 3/2003 |
| ES | 2103819 | 10/1997 |
| FR | 2618782 | 2/1989 |
| FR | 2627590 | 8/1989 |
| FR | 2629458 | 10/1989 |
| FR | 2679254 | 1/1993 |
| JP | 1128800 | 5/1989 |
| JP | 1317400 | 12/1989 |
| JP | 2187000 | 7/1990 |
| JP | 3010700 | 1/1991 |
| JP | 3502638 | 6/1991 |
| JP | 3219874 | 9/1991 |
| JP | 5192151 | 8/1993 |
| JP | 2507895 | 6/1996 |
| JP | 2580512 | 2/1997 |
| JP | 2003342285 | 12/2000 |
| JP | 2003342286 | 12/2000 |
| JP | 2001505427 | 4/2001 |
| WO | 8806634 | 9/1988 |
| WO | 8905852 | 6/1989 |
| WO | WO 90/00624 | 1/1990 |
| WO | 9002821 | 3/1990 |
| WO | WO 91/08312 | 6/1991 |
| WO | 92/01815 | 2/1992 |
| WO | WO 92/01815 | 2/1992 |
| WO | WO 92/10590 | 6/1992 |
| WO | WO 93/02217 | 2/1993 |
| WO | 93/11230 | 6/1993 |
| WO | WO 93/11230 | 6/1993 |
| WO | 9320095 | 10/1993 |
| WO | WO 93/23569 | 11/1993 |

| WO | WO 94/03594 | 2/1994 |
| WO | WO 94/26934 | 11/1994 |
| WO | WO 95/07923 | 3/1995 |
| WO | 9528942 | 11/1995 |
| WO | 96/17086 | 6/1996 |
| WO | 96/20013 | 7/1996 |
| WO | WO 97/03211 | 1/1997 |
| WO | WO 97/17433 | 5/1997 |
| WO | WO 97/17458 | 5/1997 |
| WO | 9727206 | 7/1997 |
| WO | 9804575 | 2/1998 |
| WO | WO 98/17815 | 4/1998 |
| WO | WO 98/17816 | 4/1998 |
| WO | WO 98/17817 | 4/1998 |
| WO | WO 98/24925 | 6/1998 |
| WO | 98/37240 | 8/1998 |
| WO | 98/49346 | 11/1998 |
| WO | 99/14377 | 3/1999 |
| WO | 99/50452 | 10/1999 |
| WO | WO 99/67400 | 12/1999 |
| WO | 0009673 | 2/2000 |
| WO | WO 00/09673 | 2/2000 |
| WO | 00/14244 | 3/2000 |
| WO | 0034466 | 6/2000 |
| WO | WO 00/60115 | 10/2000 |
| WO | WO 00/61804 | 10/2000 |
| WO | 01/79524 | 10/2001 |
| WO | 0196608 | 12/2001 |
| WO | WO 02/46449 | 6/2002 |
| WO | 2004/002416 | 1/2004 |

OTHER PUBLICATIONS

Seedorf et al. Virology vol. 145: 181-185, 1985).*
He et al. FEBS vol. 322(1): 21-24, May 1993.*
Searle et al. Journal of General Virology vol. 75: 1125-1137, 1994.*
Sriram et al., In vitro-selected RNA cleaving DNA enzymes from a combinatorial library are potent inhibitors of HIV-1 gene expression., 2000. The Biochemistry Journal, vol. 352, pp. 667-673.*
Bruice et al., Control of complexity constraints on combinatorial screening for preferred oligonucleotide hybridization sites on structured RNA, 1997, Biochemistry, vol. 36. pp. 5004-5019.*
"Generalized Transduction," *Escherichia coli* and *Salmonella*: Cellular and Molecular Biology, 2nd ed., vol. 2, Neidhardt et al. (eds.), ASM Press, Washington, DC., pp. 2421-2441, 1996.
Agrawal and Kandimalia, "Antisense therapeutics: is it as simple as complementary base recognition?" *Molecular Medicine Today*, 2000, 6:72-81.
Alvarez et al., "Inhibition of HPV-16 E6/E7 immortalization of normal keratinocytes by hairpin ribozymes," *Proc. Natl. Acad. Sci. USA*, 1998, 95(3):1189-1194.
Anderson, "Human Gene Therapy," *Nature*, 1998, 392(Supp.):25-30.
Bassford et al., "The Primary Pathway of Protein Export in *E. coli*", *Cell*, 1991, 65(3):367-368.
Bell et al., "RNA Molecules That Bind to and Inhibit the Active Site of a Tyrosine Phosphatase," *J. Biol. Chem.*, 1998, 273(23):14309-14314.
Benedict et al., "Triple ribozyme-mediated down-regulation of the retinoblastoma gene," *Carcinogenesis*, 1998, 19(7):1223-1230.
Bennett et al., "Pharmacology of Antisense Therapeutic Agents. Cancer and Inflammation," *Methods in Molecular Medicine: Antisense Therapeutics*, 1996, Agrawal (ed.), Chapter 2, pp. 13-46.
Bernard and Couturier, "Cell Killing by the F Plasmid CcdB Protein Involves Poisoning of DNA-Topoisomerase II Complexes," *J. Mol. Biol.*, 1992, 226(3):735-745.
Bernard et al., "Positive-selection vectors using the F plasmid *ccdB* killer gene," *Gene*, 1994, 148(1):71-74.
Bertrand et al., "Can hammerhead ribozymes be efficient tools to inactivate gene function?" *Nucl. Acids Res.*, 1994, 22(3):293-300.
Birikh et al., "The structure, function and application of the hammerhead ribozyme," *Eur. J. Biochem.*, 1997, 245:1-16.
Blanchard and Hood, "Sequence to array: probing the genome's secrets," *Nat. Biotech.*, 1996, 14:1649.

Boletta et al., "High Efficient Non-Viral Gene Delivery to the Rat Kidney by Novel Polycationic Vectors," *J. Am. Soc. Nephrol.*, 1996, 7(9):1728, Abstract No. A2409.
Bouché et al., "*dnaG* Gene Product, a Rifampicin-resistant RNA Polymerase, Initiates the Conversion of a Single-stranded Coliphage DNA to Its Duplex Replicative Form," *J. Biol. Chem.*, 1975, 250:5995-6001.
Bouché and Bouché, "Genetic evidence that DicF, a second division inhibitor encoded by the *Escherichia coli dicB* operon, is probably RNA," *Mol. Microbiol.*, 1989, 3(7):991-994.
Boyce, "Epidemiology and Prevention of Nosocomial Infections," *The Staphylococci in Human Disease*, 1997, Crossley and Archer (eds.), Churchill Livingstone, New York, NY, Chapter 12, pp. 309-329.
Branch, "A good antisense molecule is hard to find," *TIBS*, 1998, 23:45-50.
Casadaban et al., "β-Galactosidase Gene Fusions for Analyzing Gene Expression in *Escherichia coli* and Yeast," *Meth. Enzymol.*, 1983, 100:293-308.
Castanotto et al., "Antisense Catalytic RNAs as Therapeutic Agents" *Advances in Pharmacol.*, 1994, 25:289-317.
Chen et al., "Effectiveness of Three Ribozymes for Cleavage of an RNA Transcript from Human Papillomavirus Type 18," *Cancer Gene Therapy*, 1995, 2(4):263-271.
Chomczynski and Sacchi, "Single-Step Method of RNA Isolation by Acid Guanidinium Thiocyanate-Phenol-Chloroform Extraction," *Anal. Biochem.*, 1987, 162:156-159.
Christoffersen and Marr, "Ribozymes as Human Therapeutic Agents," *J. Med. Chem.*, 1995, 38(12):2023-2037.
Clawson et al., "Focal Altered Compartmentation of Repetitive B2 (Alu-like) Sequences in Rat Liver following Hepatocarcinogen Exposure," *Cell Growth Differ.*, 1996, 7(5):635-646.
Colbère-Garapin et al., "A New Dominant Hybrid Selective Marker for Higher Eukaryotic Cells," *J. Mol. Biol.*, 1981, 150(1):1-14.
Couturier et al., "Bacterial death by DNA gyrase poisoning," *Trends Microbiol.*, 1998, 6(7):269-275.
Crone et al., "Growth Inhibition by a Triple Ribozyme Targeted to Repetitive B2 Transcripts," *Hepatology*, 1999, 29:1114-1123.
Dachs et al., "Targeting Gene Therapy to Cancer: A Review," *Oncol. Res.*, 1997, 9:313-325.
Davis et al., "Preparation and analysis of RNA from Eukaryotic Cells," *Basic Methods in Molecular Biology*, 1986, Elsevier Science Publishing Co., Inc, New York, pp. 130-156.
Delaney and Isom, "Hepatitis B Virus Replication in Human HepG2 Cells Mediated by Hepatitis B Virus Recombinant Baculovirus," *Hepatology*, 1998, 28:1134-1146.
Diaz-Flores Estévez et al., "Detection of human Papillomavirus types 6b, 11, 16 and 18 in cervical scrapes by a multiplex polymerase chain reaction," *Quimica Clinica*, 1996, 15(6):420-424 (with English-language Summary).
Donis-Keller, "Phy M: an RNase activity specific for U and A residues useful in RNA sequence analysis," *Nucl. Acids Res.*, 1980, 8(14):3133-3142.
Eaton, "The joys of in vitro selection: chemically dressing oligonucleotides to satiate protein targets," *Curr. Opin. Chem. Biol.*, 1997, 1:10-16.
Eldadah et al.,"Ribozyme-Mediated Inhibition of Caspase-3 Protects Cerebellar Granule Cells from Apoptosis Induced by Serum-Potassium Deprivation," *J. Neurosci.*, 2000, 20(1):179-186.
Ellington and Szostak, "In vitro selection of RNA molecules that bind specific ligands," *Nature*, 1990, 346:818-822.
Engelberg-Kulka and Glaser, "Addiction Modules and Programmed Cell Death and Antideath in Bacterial Cultures," *Ann. Rev. Microbiol.*, 1999, 53:43-70.
Felgner et al., "Lipofection: a highly efficient, lipid-mediated DNA-transfection procedure," *Proc. Natl. Acad. Sci. USA*, 1987, 84:7413-7417.
Flanagan et al., "Cellular penetration and antisense activity by a phenoxazine-substituted heptanucleotide," *Nat. Biotech.*, 1999, 17:48-52.
Folini et al., "Inhibition of Telomerase Activity by a Hammerhead Ribozyme Targeting the RNA Component of Telomerase in Human Melanoma Cells," *J. Invest. Dermatol.*, 2000, 114:259-267.

Furuya et al., "Mortality rates amongst mice with endogenous septicaemia caused by *Pseudomonas aeruginosa* isolates from various sources," *J. Med. Microbiol.*, 1993, 39:141-146.
Gal et al., "Selection of a RNA aptamer that binds to human activated protein C and inhibits its protease function," *Eur. J. Biochem.*, 1998, 252:553-562.
Gerdes et al., "Antisense RNA-Regulated Programmed Cell Death," *Ann. Rev. Genet.*, 1997, 31:1-31.
Gerdes et al., "The *hok* Killer Gene Family in Gram-Negative Bacteria," *New Biologist*, 1990, 2(11):946-956.
Gewirtz et al., "Facilitating oligonucleotide delivery: Helping antisense deliver on its promise," *Proc. Natl. Acad. Sci. USA*, 1996, 93:3161-3163.
Goodchild and Kohli, "Ribozymes That Cleave an RNA Sequence from Human Immunodeficiency Virus: The Effect of Flanking Sequence on Rate," *Arch. Biochem. Biophys.*, 1991, 284(2):386-391.
Green et al., "Antisense Oligonucleotides: An Evolving Technology for the Modulation of Gene Expression in Human Disease," *J. Am. Coll. Surg.*, 2000, 191(1):93-105.
Greenberg et al., "The Rat Probasin Gene Promoter Directs Hormonally and Developmentally Regulated Expression of a Heterologous Gene Specifically to the Prostate in Transgenic Mice," *Mol. Endocrin.*, 1994, 8(2):230-239.
Härtl et al., "*Pseudomonas aeruginosa* Infection in Embryonated Hen's Eggs," *Arzneim.-Forsch./Drug. Res.*, 1997, 47(11):1061-1064.
Haseloff and Gerlach, "Simple RNA enzymes with new and highly specific endoribonuclease activities," *Nature*, 1988, 334(6183):585-591.
Hawley-Nelson et al., "LipofectAMINE reagent: a new, higher efficiency polycationic liposome transfection reagent," *Focus*, 1993, 15(3):73-83.
Hendry and McCall, "Unexpected anisotropy in substrate cleavage rates by asymmetric hammerhead ribozymes," *Nucl. Acids Res.*, 1996, 24(14):2679-2684.
Holcik et al., "Conditionally lethal genes associated with bacterial plasmids," *Microbiology*, 1997, 143:3403-3416.
Homann and Göringer, "Combinatorial selection of high affinity RNA ligands to live African trypanosomes," *Nucl. Acids Res.*, 1999, 27(9): 2006-2014.
Inokuchi et al., "A Hammerhead Ribozyme Inhibits the Proliferation of an RNA Coliphage SP in *Escherichia coli*," *J. Biol. Chem.*, 1994, 269(15):11361-11366.
Jen and Gewirtz, "Suppression of Gene Expression by Targeted Disruption of Messenger RNA: Available Options and Current Strategies," *Stem Cells*, 2000, 18:307-319.
Jensen et al., "Programmed cell death in bacteria: proteic plasmid stabilization systems," *Mol. Microbiol.*, 1995, 17(2):205-210.
Ji et al., "Inhibition of hepatitis B virus by retroviral vectors expressing antisense RNA," *J. Viral Hepatitis*, 1997, 4(3):167-173.
Koizumi et al., "Design of RNA enzymes distinguishing a single base mutation in RNA," *Nucl. Acids Res.*, 1989, 17(17):7059-7071.
Kraus et al., "Cutting Edge: Novel RNA Ligands Able to Bind CD4 Antigen and Inhibit CD4+ T Lymphocyte Function," *J. Immunol.*, 1998, 160:5209-5212.
Lehnherr et al., "Plasmid Addiction Genes of Bacteriophage P1: *doc*, which Causes Cell Death on Curing of Prophage, and *phd*, which Prevents Host Death when Prophage is Retained," *J. Mol. Biol.*, 1993, 233:414-428.
Lieber and Kay, "Adenovirus-Mediated Expression of Ribozymes in Mice," *J. Virol.*, 1996, 70(5):3153-3158.
Lieber and Strauss, "Selection of Efficient Cleavage Sites in Target RNAs by Using a Ribozyme Expression Library," *Mol. Cell. Biol.*, 1995, 15:540-551.
Lindsay et al., "The gene for toxic shock toxin is carried by a family of mobile pathogenicity islands in *Staphylococcus aureus*," *Mol. Microbiol.*, 1998, 29(2):527-543.
Lockhart et al., "Expression monitoring by hybridization to high-density oligonucleotide arrays," *Nat. Biotechnol.*, 1996, 14(13):1675-1680.
Lowy et al., "Isolation of Transforming DNA: Cloning the Hamster aprt Gene," *Cell*, 1980, 22:817-823.
Ma et al., "Synthetic oligonucleotides as therapeutics: the coming of age," *Biotech. Ann. Rev.*, 2000, 5:155-196.

Macejak et al., "Inhibition of Hepatitis C Virus (HCV)—RNA-dependent Translation and Replication of a Chimeric HCV Poliovirus Using Synthetic Stabilized Ribozymes," *Hepatology*, 2000, 31:769-776.
Major et al., "The Combination of Symbolic and Numerical Computation for Three-Dimensional Modeling of RNA," *Science*, 1991, 253:1255-1260.
Marians, "Replication Fork Propagation," *Escherichia coli and Salmonella: Cellular and Molecular Biology*, 1996, 2nd ed., vol. 1, Neidhardt et al. (eds.), American Society for Microbiology, Washington, DC., pp. 749-763.
Masuda et al., "*chpA* and *chpB*, *Escherichia coli* Chromosomal Homologs of the *pem* Locus Responsible for Stable Maintenance of Plasmid R100," *J. Bacteriol.*, 1993, 175(21):6850-6856.
Merril et al., "Long-circulating bacteriophage as antibacterial agents," *Proc. Natl. Acad. Sci. USA*, 1996, 93(8):3188-3192.
Meyer et al., "Search for a putative scrapie genome in purified prion fractions reveals a paucity of nucleic acids," *J. Gen. Virol.*, 1991, 72:1031-1038.
Meyer et al., "Mapping of deletions in the genome of the highly attenuated vaccinia virus MVA and their influence on virulence," *J. Gen. Virol.*, 1991, 72:1031-1038.
Miller and Whelan, "Progress in Transcriptionally Targeted and Regulatable Vectors for Genetic Therapy," *Human Gene Therapy*, 1997, 8:803-815.
Mulligan & Berg, "Selection for animal cells that express the *Escherichia coli* gene coding for xanthine-guanine phosphoribosyltransferase," *Proc. Natl. Acad. Sci. USA*, 1981, 78(4):2072-2076.
Neely and Holder, "A murine model with aspects of clinical relevance for the study of antibiotic-induced endotoxin release in septic hosts," *J. Endotoxin Research*, 1996, 3(3):229-235.
Nicolau et al., "Liposomes as Carriers for in Vivo Gene Transfer and Expression," *Meth. Enzymol.*, 1987, 149:157-176.
Norris et al., "Design and Testing of Ribozymes for Cancer Gene Therapy," *Adv. Exp. Med. Biol.*, 2000, 465:293-301.
O'Hare et al., "Transformation of mouse fibroblasts to methotrexate resistance by a recombinant plasmid expressing a prokaryotic dihydrofolate reductase," *Proc. Natl. Acad. Sci. USA*, 1981, 78(3):1527-1531.
Ohme-Takagi et al., "In vivo RNA transcript-releasing plasmid possessing a universal pseudo-terminator by means of artificial ribozymes," *Nucl. Acids Res.—Symposium Series*, 1990, 22:49-50.
Osborne and Ellington, "Nucleic Acid Selection and the Challenge of Combinatorial Chemistry," *Chem. Rev.*, 1997, 97:349-370.
Pace and Smith, "Ribonuclease P: Function and Variation," *J. Biol. Chem.*, 1990, 265(7):3587-3590.
Palese et al., "Negative-strand RNA viruses: genetic engineering and applications," *Proc. Natl. Acad. Sci USA*, 1996, 93:11354-11358.
Pan et al., "A selection system for identifying accessible sites in target RNAs," *RNA*, 2001, 7(4):610-621.
Pan et al., "Isolation of virus-neutralizing RNAs from a large pool of random sequences," *Proc. Natl. Acad. Sci. USA*, 1995, 92(25):11509-11513.
Parker et al., "Ribozymes: Principles and Designs for Their Use as Antisense and Therapeutic Agents," *Gene Regulation: Biology of Antisense RNA and DNA*, 1992, Erickson et al. (eds.), Raven Press, New York, pp. 55-70.
Passman et al., "In situ demonstration of inhibitory effects of hammerhead ribozymes that are targeted to the hepatitis Bx sequence in cultured cells," *Biochem. Biophys. Res. Commun.*, 2000, 268:728-733.
Perlman et al., "Adenovirus-encoded hammerhead ribozyme to Bcl-2 inhibits neointimal hyperplasia and induces vascular smooth muscle cell apoptosis," *Cardiovasc. Res.*, 2000, 45:570-578.
Pier et al., "Role of Mutant CFTR in Hypersusceptibility of Cystic Fibrosis Patients to Lung Infections" *Science*, 1996, 271:64-67.
Poulsen et al., "The *gef* gene from *Escherichia coli* is regulated at the level of translation," *Mol. Microbiol.*, 1991, 5(7):1639-1648.
Recsei et al., "Cloning, Sequence, and Expression of the Lysostaphin Gene from *Staphylococcus simulans*," *Proc. Natl. Acad. Sci. USA*, 1987, 84:1127-1131.

Ren et al., "Construction and deployment of triple ribozymes targeted to multicatalytic proteinase subunits C3 and C9," *Gene Ther. Mol. Biol.*, 1999, 3:257-269.

Salmi et al., "Dopamine $D_2$ receptor ribozyme inhibits quinpirole-induced stereotypy in rats," *Eur. J. Pharmacol.*, 2000, 388:R1-R2.

Santerre et al., "Expression of prokaryotic genes for hygromycin B and G418 resistance as dominant-selection markers in mouse L cells," *Gene*, 1984, 30:147-156.

Savioz et al., "*Pseudomonas aeruginosa* promoters which contain a conserved GG-$N_{10}$-GC motif but appear to be RpoN-independent," *Mol. Gen. Genet.*, 1993, 238:74-80.

Schena et al., "Quantitative Monitoring of Gene Expression Patterns with a Complementary DNA Microarray," *Science*, 1995, 270:467-470.

Schmidt et al., "Regulation of *Escherichia coli secA* mRNA Translation by a Secretion-Responsive Element," *J. Bacteriol.*, 1991, 173(20):6605-6611.

Schmidt et al., "Base and sugar requirements for RNA cleavage of essential nucleoside residues in internal loop B of the hairpin ribozyme: implications for secondary structure," *Nucl. Acids Res.*, 1996, 24(4):573-581.

Schmidt and Oliver, "SecA Protein Autogenously Represses Its Own Translation during Normal Portein Secretion in *Escherichia coli*," *J. Bacteriol.*, 1989, 171(2):643-649.

Slopek et al., "Results of Bacteriophage Treatment of Suppurative Bacterial Infections in the Years 1981-1986," *Archivum Immunologiae et Therapiae Experimentalis*, 1987, 35:569-583.

Soothill, "Treatment of experimental infections of mice with bacteriophages," *J. Med. Microbiol.*, 1992, 37(4):258-261.

Steele et al., "Effects of Human Papillomavirus Type 18-Specific Antisense Oligonucleotides on the Transformed Phenotype of Human Carcinoma Cell Lines," *Cancer Res.*, 1993, 53(10):2330-2337.

Sternberg and Coulby, "Recognition and Cleavage of the Bacteriophage P1 Packaging Site (*pac*) II. Functional limits of *pac* and location of *pac* cleavage termini," *J. Mol. Biol.*, 1987, 194(3):469-479.

Stewart et al., "Gene Transfer In Vivo with DNA-Liposome Complexes: Safety and Acute Toxicity in Mice," *Hum. Gene Ther.*, 1992, 3:267-275.

Stieritz and Holder, "Experimental Studies of the Pathogenesis of Infections Due to *Pseudomonas aeruginosa*: Description of a Burned Mouse Model," *J. Infect. Dis.*, 1975, 131(6):688-691.

Stull and Szoka Jr., "Antigene, Ribozyme and Aptamer Nucleic Acid Drugs: Progress and Prospects," *Pharmaceutical Res.*, 1995, 12(4):465-483.

Sullivan et al., "Development of Ribozymes for Gene Therapy," *J. Invest. Dermatol.*, 1994, 103:85S-95S.

Suzuki et al., "Adenovirus-mediated ribozyme targeting of HER-2/neu inhibits in vivo growth of breast cancer cells," *Gene Ther.*, 2000, 7:241-248.

Szybalska & Szybalski, "Genetics of Human Cell Lines, IV. DNA-Mediated Heritable Transformation of a Biochemical Trait," *Proc. Natl. Acad. Sci. USA*, 1962, 48:2026-2034.

Taira et al., "Construction of a novel artificial-ribozyme-releasing-plasmid," *Protein Eng.*, 1990, 3(8):733-737.

Taira et al., "Construction of a novel RNA-transcript-trimming plasmid which can be used both in vitro in place of run-off and (G)-free transcriptions and in vivo as multi sequences transcription vectors," *Nucl. Acids Res.*, 1991, 19:5125-5130.

Taira and Nishikawa, "Construction of Several Kinds of Ribozymes," *Gene Regulation: Biology of Antisense RNA and DNA*, vol. 1, Erickson and Izant (eds.), 1992, Raven Press, New York, pp. 35-53.

Templeton et al., "Improved DNA: liposome complexes for increased systemic delivery and gene expression," *Nat. Biotech.*, 1997, 15:647-652.

Tétart and Bouché, "Regulation of the expression of the cell-cycle gene *ftsZ* by DicF antisense RNA. Division does not require a fixed number of FtsZ molecules," *Mol. Microbiol.*, 1992, 6(5):615-620.

Tuerk and Gold, "Systematic Evolution of Ligands by Exponential Enrichment: RNA Ligands to Bacteriophage T4 DNA Polymerase," 1990, *Science*, 249:505-510.

Uhlenbeck, "A small catalytic oligoribonucleotide," *Nature*, 1987, 328:596-600.

Usman et al., "Design, synthesis, and function of therapeutic hammerhead ribozymes," *Nucl. Acids Res.*, 1996, 10:243-264.

Usman et al., "Hammerhead ribozyme engineering," *Curr. Opin. Struct. Biol.*, 1996, 1:527-533.

Vieweg et al., "Efficient Gene Transfer with Adeno-associated Virus-based Plasmids Complexed to Cationic Liposomes for Gene Therapy of Human Prostate Cancer," *Cancer Res.*, 1995, 55:2366-2372.

Wang et al., "In vitro selection of novel RNA ligands that bind human cytomegalovirus and block viral infection," *RNA*, 2000, 6:571-583.

Waymack et al., "An evaluation of cyclophosphamide as an immunomodulator in multiple septic animal models," *J. Burn Care Rehabil.*, 1988, 9(3):271-274.

Wechsler and Gross, "*Escherichia coli* Mutants Temperature-Sensitive for DNA Synthesis," *Mol. Gen. Genet.*, 1971, 113:273-284.

Wei et al., "Relationship between Viral DNA Synthesis and Virion Envelopment in Hapatitis B Viruses," *J. Virol.*, 1996, 70(9):6455-6458.

Weizsaecker et al., "Cleavage of Hepatitis B Virus RNA by Three Ribozymes Transcribed from A Single DNA Template," *Biochem. Biophys. Res. Comm.*, 1992, 189(2):743-748.

Welch et al., "Intracellular application of hairpin ribozyme genes against hepatitis B virus," *Gene Therapy*, 1997, 4(7):736-743.

Whitton, "Antisense Treatment of Viral Infection," *Adv. Virus Res.*, 1994, 44:267-303.

Wigler et al., "Transfer of Purified Herpes Virus Thymidine Kinase Gene to Cultured Mouse Cells," *Cell*, 1977, 11:223-232.

Wigler et al., "Transformation of mammalian cells with an amplifiable dominant-acting gene," *Proc. Natl. Acad. Sci. USA*, 1980, 77(6):3567-3570.

Woods et al., "Correlation of *Pseudomonas aeruginosa* virulence factors from clinical and environmental isolates with pathogenicity in the neutropenic mouse," *Can. J. Microbiol.*, 1997, 43:541-551.

Yang et al., "DNA ligands that bind tightly and selectively to cellobiose," *Proc. Natl. Acad. Sci. USA*, 1998, 95:5462-5467.

Yarmolinsky and Stevens, "Replication-Control Functions Block the Induction of an SOS Response by a Damaged P1 Bacteriophage," *Mol. Gen. Genet.*, 1983, 192:140-148.

Yuyama et al., "Construction of a tRNA-embedded-ribozyme trimming plasmid," *Biochem. Biophys. Res. Comm.*, 1992, 186(3):1271-1279.

Zaidi et al., "Cystic Fibrosis Transmembrane Conductance Regulator-Mediated Corneal Epithelial Cell Ingestion of *Pseudomonas aeruginosa* Is a Key Component in the Pathogenesis of Experimental Murine Keratitis" *Infection and Immunity*, 1999, 67(3):1481-1492.

Zhou et al., "Expression of Hammerhead Ribozymes by Retroviral Vectors to Inhibit HIV-1 Replication: Comparison of RNA Levels and Viral Inhibition," *Antisense & Nucleic Acid Drug Development*, 1996, 6:17-24.

Zuker and Jacobson, "Using reliability information to annotate RNA secondary structures," *RNA*, 1998, 4:669-679.

Zuker and Stiegler, "Optimal computer folding of large RNA sequences using thermodynamics and auxiliary information," *Nucl. Acids Res.*, 1981, 9:133-148.

Plourde and Wu, "Targeted therapy for viral hepatitis," *Adv. Drug Del. Rev.*, 1995, 17:311-315.

Venturini et al., "Kinetic selection of HPV 16 *E6/E7*-directed antisense nucleic acids: anti-proliferative effects on HPV 16-transformed cells," *Nucl. Acids Res.*, 1999, 27(7):1585-1592.

Sriram and Banerjea, "In vitro-selected RNA cleaving DNA enzymes from a combinatorial library are potent inhibitors of HIV-1 gene expression," *Biochem. J.*, 2000, 352:667-673.

Bruice and Lima, "Control of complexity constraints on combinatorial screening for preferred oligonucleotide hybridization sites on structured RNA," *Biochem.*, 1997, 36:5004-5019.

Abul-Hassan et al., 1990 Bacteriophage therapy of *Pseudomonas* burn wound sepsis. Annals of Med Burn Club. 34:262-264.

Altschul et al., Nat. Genet., 1994, 6:119-129.

Alvarez- Salas et al. Anti Nuc Ac Drug Dev 9:441-50 (1999).

Arruda, S. et al. Science 261:1454-1457, 1993.

Ausubel et al., Short Prot. In Mol. Biol. 2nd Ed. 1989, Ch.8: 1-25.

Beutner et al. Jour of Amer. Acad. Of Derm., vol. 38, No. 2, Part 1: 230-239 1998).

Buchardt et al., TIBTECH., 1993, 11:384-386.

Buhr et al. The Plant Jour. 30(2), 155-163 (2002).
Cairns, M. et al. Nature Bitech vol. 17 May 1999 pp. 480-486.
Cao et al., World J. Gastroenterol., 1998, 4(5):388-391.
Caskey, Ann. N.Y. Acad. Sciences-Antisense Strategies, 1992, 660:154-158.
Choo et al. Gynecol. Oncol. 2000; 78(3 pt 1): 293-301.
Cole et al. J. Mol. Biol. 193 (4)1 599-608 (1987).
Corey, TIBTECH., 1997, 15:224-229.
Crooke, Annu. Rev. Med., 2004, 55:61-95.
Crooke, Antisense Research and Applications, 1998, Springer-Verlag Press, Berlin, Heidelber, New York, Chapter 1, p. 3.
Dachs et al., Oncol. Res., 1997, 9:313-325.
Dartmann et al. Virology 151(1)1 124-130 (1986).
De Mesmaeker et al., Curr. Opin. Struc. Biol., 1995, 5:343-355.
Doudna and Cech, Nature, 2002, 418:222-228.
Dueholm and Nielsen, New J. Chem., 1997, 21:19-31.
Elbashir et al., Nature, 2001, 411:494-498.
Fedor and Uhlenbeck Proc. Nat. Acad.Sci. 87:1668-1672, 1990.
Feldman and Sen, J. Mol. Biol. 313, 283-294 (2001).
Fields et al. (eds.), Fields Virology, 1996, 3rd Edition, Lippincott Williams & Wilkins, New York, New York, pp. 186-191.
Galibert, et al. Nature 281, 646-650, 1979.
Garber, K., Technology Review, 2002:42-48.
GenBank® Accession No. AF003019 dated Sep. 20, 1997, 2 pages.
GenBank® Accession No. K02718 dated Mar. 18, 1994, 6 pages.
GenBank® Accession No. U34113 dated Mar. 8, 1996, 2 pages.
GenBank® Accession No. U34135 dated Mar. 8, 1996, 2 pages.
GenBank® Accession No. U89348 dated Oct. 27, 1999, 5 pages.
GenBank® Accession No. X02496 dated Apr. 27, 1999, 4 pages.
Gossler et al., Proc. Natl. Acad. Sci. USA, 1986, 83(23):9065-9069.
Guidotti et al. Journal of Virology p. 6158-6169, 1995.
Hammond et al., Nature, 2000, 404:293-296.
Hara et al., Gene Therapy, 1995, 2(10):784-788.
Hara et al., Biochim. Biophys. Acta, 1996, 1278:51-58.
Hara et al., Gene, 1995, 159(2):167-174.
Henikoff and Henikoff, Proc. Natl. Acad. Sci. USA, 1992, 89:10915-10919.
Herasse et al. Moll and Cell Biol vol. 19, No. 6, p. 4047-4055 (1999).
Hyrup and Nielsen, Bioorg. Med. Chem., 1996, 4:5-23.
Jang et al., J. Virol., 1988, 62(8):2636-2643.
Jiang and Milner, Oncogene 21, 6041-6048 (2002).
Karlin and Altschul, Proc. Natl. Acad. Sci. USA, 1990, 87:2264-2268.
Knudsen and Nielsen, Anti-Cancer Drugs, 1997, 8:113-118.
Kreider et al. J. of Virol. vol. 61, No. 2, 590-593 (1987).
Kunke et al. Cancer Gene Ther. 2000; 7(5):766-77.
Laemmli, U.K. Nature vol. 227, p. 680-5 (1970).
Lederberg J., Smaller fleas . . . ad infinitum: therapeutic bacteriophage redux,: Proc Natl Acad Sci USA Apr. 16, 1996;93(8):3167-8.
Lewis et al. Antiviral Res. 2000; 48(3)187-96.
Lo, Mol. Cell. Biol., 1983, 3(10):1803-1814.
Lutz et al., J. Am. Chem. Soc., 1997, 119:3177-3178.
Madrigal et al. Gynec. Onco. 64, 18-25 (1997).
Maitland et al., Br. J. Cancer, 1989, 59(5):698-703.
Meyer et al. J. Gen. Virol., 1991, 72:37-49.
Mizuno et al. 1984.Proc. Natl Acad sci USA, 81(7):1966070.
Nedbal and Sczakiel, Antisense & Nuc. Ac. Drug Dev. 7:585-589 (1997).
Neidhardt et al. (eds.), *Escherichia coli* and *Slmonella*: Cell and Mol Biol19961 2nd ed., vol. 2, ASM Press, Washington DC, pp. 2421-2441.

Nielsen and Haaima, Chem. Soc. Rev., 1997, pp. 73-78.
Nielsen and Ørum, Molecular Biology: Current Innovations and Future Trends, 1995, Part 2, Horizon Scientific Press, pp. 73-89.
Nielsen et al., Antisense Research and Applications, 1992, Crooke and Lebleu (eds.), CRC Press, Chapter 19, pp. 363-372.
Nielsen et al., Bioconjugate Chem., 1994, 5:3-7.
Nielsen et al., Science, 1991, 254:1497-1500.
Nielsen et al., Anti-Cancer Drug Design, 1993, 8:53-63.
Nielsen, Annu. Rev. Biophys. Biomol. Struct., 1995, 24:167-183.
Nielsen, Chem. Eur. J., 1997, 3(4):505-508.
Nielsen, Antisense Therapeutics. Perspectives in Drug Discovery and Design, 1996, 4:76-84.
Okumoto et al. Biochem. 42, 2158-2165 (2003).
Opalinska et al., Nature Review, 2002, 1:503-514.
Ørum et al., Nucleic Acid Amplification Technologies: Application to Disease Diagnostics, 1997, Lee et al. (eds.), BioTechniques Books Div., Eaton Publishing, pp. 29-48.
Pan et al. Mol Ther. 7:1-11, 129-139 (2003).
Plourde and Wu, Advanced Drug Delivery Reviews, 1995, 17:311-315.
Robertson et al., Cancer Gene Therapy, 1998, 5(5):331-336.
Rorke, E. J. of Nat. Can. Res. vol. 89, No. 17 1243-1246 (1997).
Sambrook et al. Mol Clon.: A Lab Man, 2nd Ed. Cold Springs Harbor Laboratory, NY, 21-41, 1989.
Santiago et al. Nat. Med.vol. 5, No. 11, 1264-1269 (1999).
Santoro, S.W. and Joyce, G.F.BiochemSep. 1998, 37, 13330-42.
Santoro, S.W. and Joyce, G.F.Proc Natl Acad Sci USA, vol. 94, pp. 4262-4266 Apr. 1997.
Schnieke et al., Science, 1997, 278:2130-2133.
Schwarze et al. Science vol. 285, 1569-1572, 1999.
Slebos et al. Proc. Acad. Sci. USA vol. 91, pp. 5320-5324 (1994).
Smith, H. Williams, Journal of General Microbiology, (1982) 128:307-318.
Smith, J. et al. Cell 82:101-110, 1995.
Stacey et al. Oncogene 9, 635-645 (1994).
Takagi et al. Biochem. Soc. Trans. vol. 30, Part 6, 1145-1149 (2002).
Tan et al., Cancer Res. 55, 4599-4605 (1995).
Tan et al., J. Gen. Virol.75:2663-2670, 1994.
Templeton et al., Nat. Biotechnol., 1997, 15:647-652.
Thompson et al., Cell, 1989, 56:313-321.
Van der Putten et al., Proc. Natl. Acad. Sci. USA, 1985, 82:6148-6152.
Voeks et al. Gene Therapy and Molecular Biology. vol. 1 (407-418) Mar. 1998.
Voeks et al. Ribo in Gene Ther.R.G. Landes publ. Chap. 13, 99.165-173, 1998.
Voelkel-Johnson et al., Proc. Annu. Meet. Am. Assoc. Cancer Res., 1997, 38, A1286.
Wagatsuma et al., J. Virol., 1990, 64(2):813-821.
Walboomers et al. J. of Path. 189: 12-19 (1999).
Walder et al. Nucleic Ac. Res. 1993; 21(18):4339-43.
Wang et al., J. Biol. Chem., 2000, 275(51):40174-40179.
Warashina, M. et al. Chem & Biol 1999 vol. 6 pp. 237-250.
Wu et al., Hepatology, 1998, 27(3):772-778.
Yuyama et al. Nuc. Acids Res. 1994, vol. 22, No. 13: 5060-5067.
Zhang et al. Exper. Cell Res. 273. 73-84 (2002).
Zheng et al. Chin Med J (Engl) 2002; 115(10):1501-6.
Clawson, Gary A. "Ribozyme Libraries and Cleavage Site Identification" U.S. Appl. No. 60/417,997, filed Oct. 14, 2002.

\* cited by examiner

```
         ACTCGCGGA TCATCTTCAC CATCGGCCGC AACTCCTGCG
GGATATCCTC GTCCTCCTCC TCCACCGGCA CCCCCATGGT AGCGGCCAGC-
TCGCGCCCTG CCTGGGAAAG CTGTACATGC TGATCGGCGG CGTCGGTGCC
GGCGGCCGGG TCTTCCGCCT GCTCGGCGGT GCCGGTCCGT GCGGCCTTGG
CGTCCGCGGC GGCGCGCGAT GAGGGCGGCA CCTGGGTGGT GATCCAGCCA
CTGAGGGTCA ACATTCCAGT CACTCCGGGA AAAATGGAAT TCTTCCATTG
GATCGGCCCA CGCGTCGCGA ACTTGAGCCC CCTTTTCGTC GCCCCTTGAC
AGGGTGCGAC AGGTAGTCGC AGTTGTTTGA CGCAAGTCAC TGATTGGAAA
CGCCATCGGC CTGTCAGAAA TGGTCGTTGCC AGACCTATGG CTGGCACCCG
CATCGCGGCT GCGTTACCCT TACTCCTGTT GTGCCTTTAA CCTAGCAAGG AC
```

FIG.1D

```
         AATTCCTCGA AGTCCTTGCG CTGCTTGTCG TTCATGATGT
CGTAGATCAG CGCATGCACC TGCTTGTGTT CCAGCGGTGG CAGGTTGATC
CGGCGTACAT CGCCATCCAC CCGGATCATG GGTGGCAGGC CGGCGGAGAG
GTGCAGGTCC GAAGCGCCCT GTTTGGCACT GAAGGCGAGC AGCTCGGTAA
TATCCATGGG ACTCCCCAAT TACAAGCAAG CAGGTAGAAT GCCGCCAAAG
CCGCCGTCTC GGACAAGGAA AACACCGGAT GAGCCAGGGT GCTTCCAGGA
CACGCGTGGT GTCCTGCGCC AGACGCGGAA CCTCGACACT GGAACAGGAA
GATGGCCATC GAGGCCGGCG GTTTCGAGGG CGTCGAGCCG ACGCCGACCG
CACTTCCATA GGGCGCAGGT AATGTCCACG ATAGCAGAGA ATATTGCAAA
GGTTGCCGCG CGCATCCGTG AGGCAGCGCA AGCTGCGGGG CGCGATCCGG
CCACGGTCGG CCTGCTCGCC GTGAGCAAGA CCAAGCCCGC CGCCGCGGTG
CGCGAGGCGC ACGCCGCCGG CCTTCGCGAC TTCGGCGAAA ACTACCTGCA
GGAGGCCCTC GGCAAGCAGG CCGAACTGGC CGACCTGCCC TTGAACTGGC
ACTTCATCGG CCCCATCCAG TCGAACAAGA CGCGGCCCAT CGCCGAGCAT
TTCCAGTGGG TGCACTCGGT GGACCGGTTG AAGATCGCGC AGCGCCTGTC
GGAGCAACGC CCGGCCGGGC TGCCGCCCCT GAATGTCTGC CTGCAGGTCA
ACGTCAGCGG CGAAGCCAGC AAGTCCGGCT GCGCCCCCGA GGACCTGCCC
GCCCTGGCCC AGGCCGTGAA GCAACTGCCC AACCTCCGAT TGCGTGGCCT
GATGGCCATC CCCGAACCCA CCGCCGAACG CGCCGCGCAA CACGCCGCGT
TCGCCCGCCT GCGCGAACTG CTGCTGGACC TGAACCTTGG CCTGGACACC
CTGTCCATGG GCATGAGCGA CGACCTCGAG GCAGCCATCGG CGAAGGTGCG
ACCTGGGTCC GCATCGGTAC CGCCCTGTTC GGCGCCCGCGA CTACGGCGCG
CCGGCTTCTT GAATGAATCCC
```

FIG.1E

CTAGAGCTAT TGATGTGGAT CAACATTGTC CACTAGCCGC
TGCCGCCTAA TCTCCAGAAT TGTGAG

FIG.1F

```
   1 ttatttagca ggaataatta gccagattat cgagggagtt ccagggcaatccaaacattg
  61 ttatatatgc atttataaaa ttttcaagat aatttattat tcatacccttgcccttttgtt
 121 tcaaaattat gccctttttt tgcccttgga aacaaccaca ctcctaaattaataggtggt
 181 gtggtttgat catttataat ataacataaa aacaaccacc cagtaactagtatgagtggc
 241 gtagcgacta taacaactct atgttatcaa gatatatgta tatgagtgatgacaaggaag
 301 atgtctcctg tgagccaaac agccagatat atggcctctt gccgggctatatagttcact
 361 cctactatat acacatgtaa ttataacata aaaaaataga caagtaccgaagtacctgcc
 421 taaataacaa caagattaac atgtgaataa tggaaataaa aagtcacgcccgaaggctaac
 481 ttacgaatag atgaaaattt gaacacattg ctgtgtctaa aatgattatagcataaataa
 541 cgaatatttc cagctcgaaa ttaatatatt gtaataataa tattttatatctttgttaat
 601 aattatttaa ttgatttaca taaataataa ttgtaaaatt aatttgtaatcgattgcaaa
 661 taagttatag gagaaaataa aatgaataaa aaactattaa caaaaacattgatagcaagt
 721 gctttagttt taacaacagt aggttcaggt tttcattctt cttcaaattataatggtatt
 781 aataacgttg aaaaagctga gcaaacgaca gataacgcat tgtggaaaaatgtaagagac
 841 gctttaaaag acgcgaatat tatcgataaa acagataatg aaaatgtcaaggttacgtat
 901 aaaatagaaa atggtggaga aaataccata gaaggaacag ttaatttagaaaatattagt
 961 acttcaaaca atcctaaaat aaaccctcaa aatgttacaa aaattaatataactagaaaa
1021 aatccgaact accctaatat tgatgctaat aatacatgga aaaaattaccagaaaaattg
1081 aaagaaaaaa atatagtgga acaacggcga caatgtttca atcttaagtacagaccctaa
1141 agatgagact gtattcggta aagtaggaga agataaatca aacgtaagcaatagatacat
1201 caatcctaaa gatataaatg aattcaaatc actaaaaata cttttttccgaggcagatta
1261 ctcctgcctc tttctttgaa cagtgatatc ttctgatcta tgtaacactcaattacttca
1321 gattctttac ctttaacttc ctttaattca tttctctcta tctcctcaaaaagttgtgct
1381 ttttgatttg tgattggagt tgggcgtttt ttcatcgcgt tgtttcaattcctttttaag
1441 gtattctaat tctcttctag tcatatcaat tgttttttta cttctcacctttagtgaaat
1501 actcttatcc tttctcttct tgcgttaatg ttgctaatta gtataaaatacatgcgccca
1561 tatattccaa tggtaggaca tttaattctg gatttttcagc tattttcataaatctattat
1621 ctgataattt gcttaatcca attttcaagc catagcctaa attccccatccactaagtca
1681 ttttgtttca tatggttttta atctacggcc aatctcaaag atagattgaccagcgatgtt
1741 taaagtcata tttcacggat ccacatttac gataaacata tctagttacacaatattatc
1801 ccttactgca acacaggacg tttctcagcg taaaaaacac cactagaaagtgactttaaa
1861 gaatataact aattcaaact tatattaatt aatattcttt aaatgaccactcacactttg
1921 tttttttgcta tttgtaactt taaaatgttg tttgaaatct atatttttttgatatagctc
1981 cctatgtaac aaacaatttt taattaatat atatttaaac aagtcaatttagagatcggt
2041 taattcgatt catttaaata atatttatac attctatatg taaacgtttacacatttgaa
2101 gtaaggagaa ttaaaaatga
```

FIG.1G

Figure 11A:
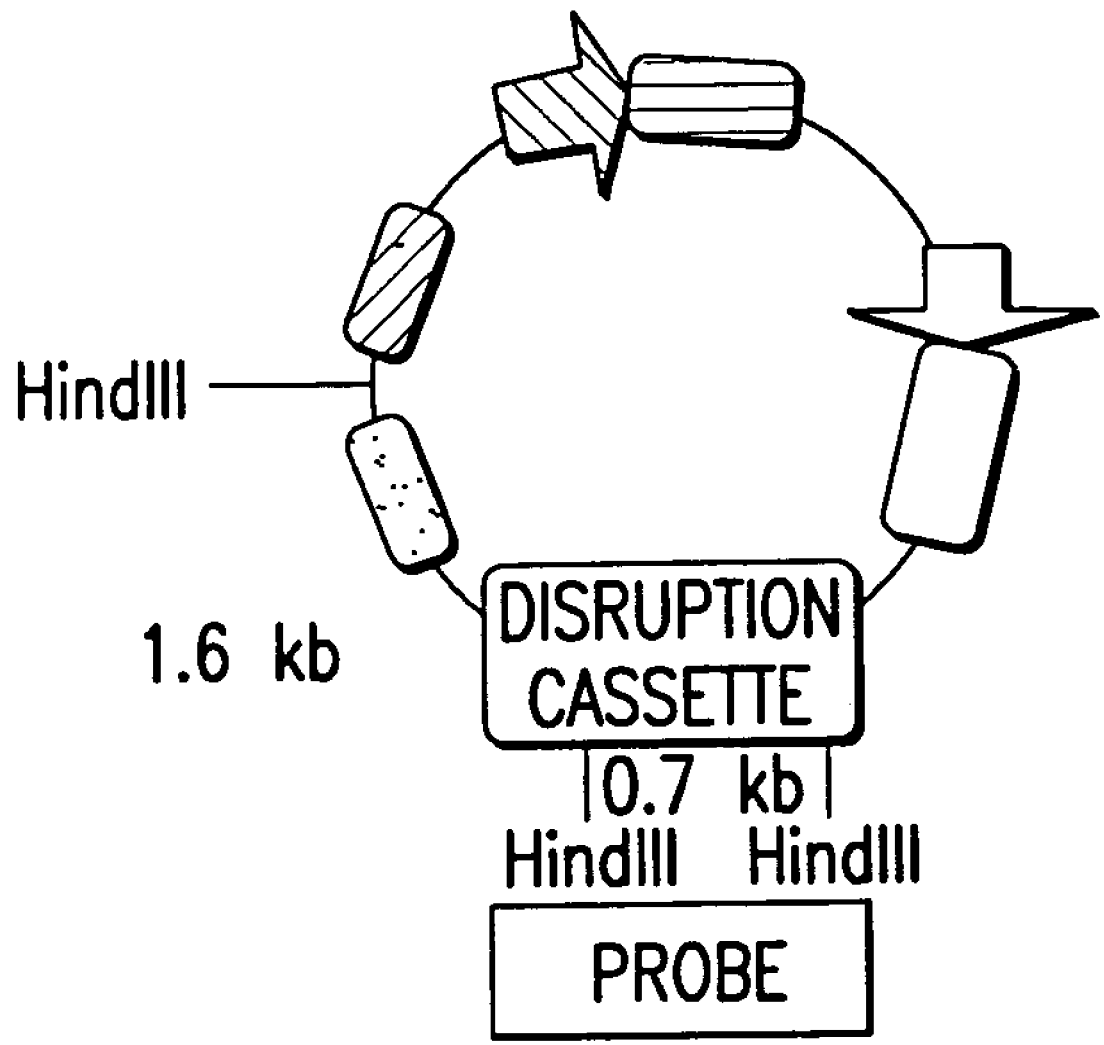

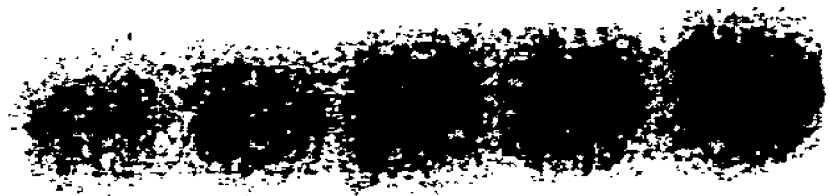
FIG. 11B

```
           a  a  c            c   c                    g   c
CCACTAAAAAGCA TGATCA ACTCTAA TGATCA ACATGCAGG TGATCA CATTGCG
Pro Leu Lys Ser Met Ile Ile Asp His Ser Asn Asp Gln His Ala Gly Asp His Ile Ala g   g   g
GCTGAAATAGCGGAAAAACAAAGAGTTAATGCCCGTTGTCAGTGCCGCCAGTCGAGAATGCC
Ala Glu Ile Ala Glu Lys Glu Arg Val Asn Ala Val Val Ser Ala Ala Val Glu Asn Ala
AATCAANNANTTA c        c          c                 t    t
AAGCGCCAAAATAAGCCGCATAAA TGATCG TTCAGA TGATCA TGACG TGATCA CCCGC
Lys Arg Gln Asn Lys Arg Ile Asn Asp Arg Ser Asp Asp His Asp Val Ile Thr Arg
```

FIG. 12

5'-CAGGCGACAGGTATAGTTTCTCTCCGATTTGTGCCTGTCGCCTGC

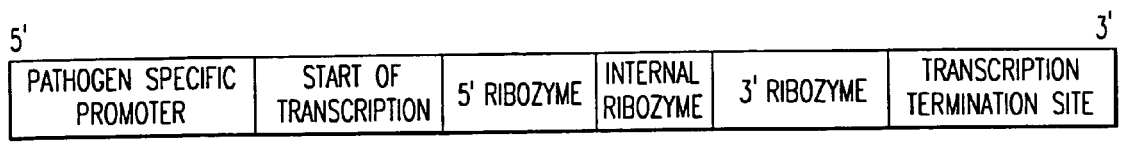
FIG.22A
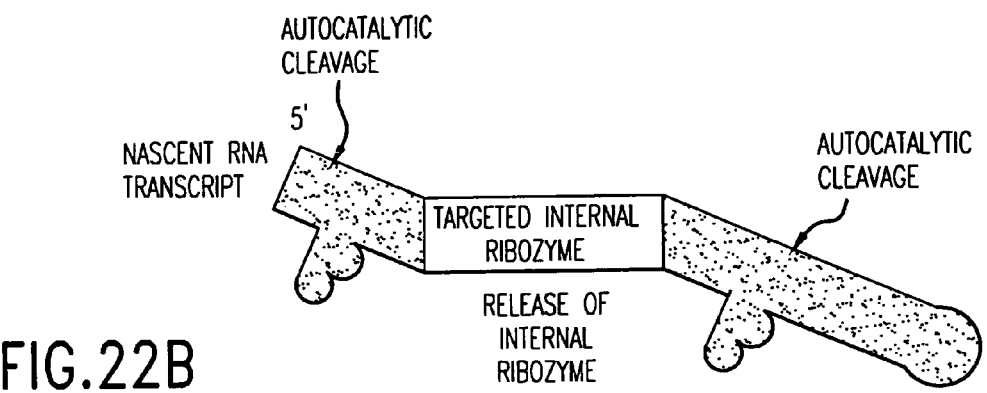
FIG.22B
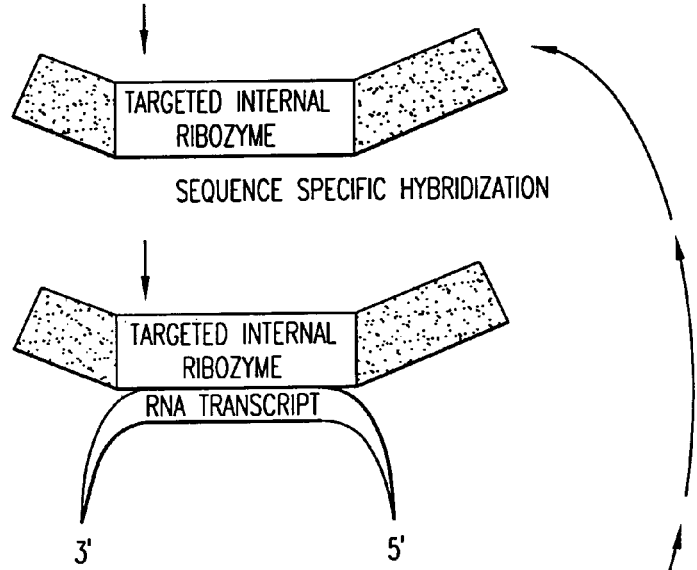
FIG.22C
FIG.22D
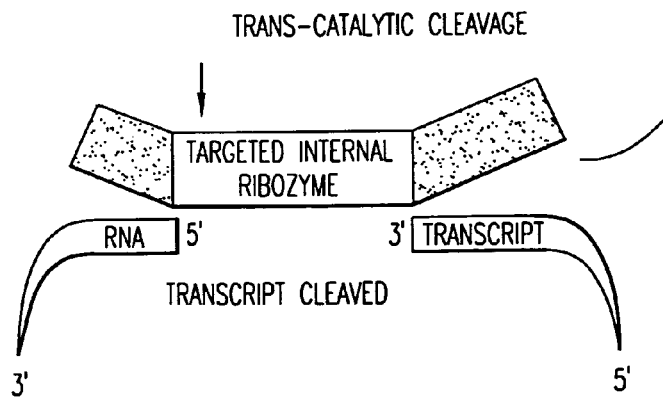
FIG.22E

SEQUENCE LISTING

<160> NUMBER OF SEQ ID NOS: 14

<210> SEQ ID NO 1
<211> LENGTH: 66
<212> TYPE: DNA
<213> ORGANISM: Artificial Sequence
<220> FEATURE:
<223> OTHER INFORMATION: LEASHI promoter

<400> SEQUENCE: 1
gatcctcaga aaattatttt aaatttccaa ttgacattgt gagcggataa caatataatg     60
tgtgga                                                                66

<210> SEQ ID NO 2
<211> LENGTH: 74
<212> TYPE: DNA
<213> ORGANISM: Artificial Sequence
<220> FEATURE:
<223> OTHER INFORMATION: Modified rrnb promoter

<400> SEQUENCE: 2
agaaagcaaa aataaatgct tgacactgta gcgggaaggc gtataatgga attgtgagcg     60
gataacaatt caca                                                       74

<210> SEQ ID NO 3
<211> LENGTH: 492
<212> TYPE: DNA
<213> ORGANISM: Artificial Sequence
<220> FEATURE:
<223> OTHER INFORMATION: ANR promoter

<400> SEQUENCE: 3
actcgcggat catcttcacc atcggccgca actcctgcgg gatatcctcg tcctcctcct     60
ccaccggcac ccccatggta gcggccagct cgcgccctgc ctgggaaagc tgtacatgct    120
gatcggcggc gtcggtgccg gcggccgggt cttccgcctg ctcggcggtg ccggtccgtg    180
cggccttggc gtccgcggcg gcgcgcgatg agggcggcac ctgggtggtg atccagccac    240
tgagggtcaa cattccagtc actccgggaa aaatggaatt cttccattgg atcgcccac     300 gcgtcgcgaa cttgagcccc cttttcgtcg cccttgaca gggtgcgaca ggtagtcgca     360
gttgtttgac gcaagtcact gattggaaac gccatcggcc tgtcagaaat ggtcgttgcc    420
agacctatgg ctggcacccg catcgcggct gcgttaccct tactcctgtt gtgcctttaa    480
cctagcaagg ac                                                        492

<210> SEQ ID NO 4
<211> LENGTH: 1113
<212> TYPE: DNA
<213> ORGANISM: Artificial Sequence
<220> FEATURE:
<223> OTHER INFORMATION: ProC promoter

<400> SEQUENCE: 4
aattcctcga gtccttgcg ctgcttgtcg ttcatgatgt cgtagatcag cgcatgcacc      60
tgcttgtgtt ccagcggtgg caggttgatc cggcgtacat cgccatccac ccggatcatg    120
ggtggcaggc cggcggagag gtgcaggtcc gaagcgccct gtttggcact gaaggcgagc    180
agctcggtaa tatccatggg actccccaat tacaagcaag caggtagaat gccgccaaag    240
ccgccgtctc ggacaaggaa aacaccggat gagccagggt gcttccagga cacgcgtggt    300

| | |
|---|---|
| gtcctgcgcc agacgcggaa cctcgacact ggaacaggaa gatggccatc gaggccggcg | 360 |
| gtttcgaggg cgtcgagccg acgccgaccg cacttccata gggcgcaggt aatgtccacg | 420 |
| atagcagaga atattgcaaa ggttgccgcg cgcatccgtg aggcagcgca agctgcgggg | 480 |
| cgcgatccgg ccacggtcgg cctgctcgcc gtgagcaaga ccaagcccgc cgccgcggtg | 540 |
| cgcgaggcgc acgccgccgg cctcgcgac ttcggcgaaa actacctgca ggaggccctc | 600 |
| ggcaagcagg ccgaactggc cgacctgccc ttgaactggc acttcatcgg ccccatccag | 660 |
| tcgaacaaga cgcggcccat cgccgagcat ttccagtggg tgcactcggt ggaccggttg | 720 |
| aagatcgcgc agcgcctgtc ggagcaacgc ccggccgggc tgccgcccct gaatgtctgc | 780 |
| ctgcaggtca acgtcagcgg cgaagccagc aagtccggct cgcccccga ggacctgccg | 840 |
| gccctggccg aggccgtgaa gcaactgccc aacctccgat tgcgtggcct gatggccatc | 900 |
| cccgaaccca ccgccgaacg cgccgcgcaa cacgccgcgt tcgcccgcct gcgcgaactg | 960 |
| ctgctggacc tgaaccttgg cctggacacc ctgtccatgg gcatgagcga cgacctcgag | 1020 |
| gcagccatcg gcgaaggtgc gacctgggtc gcatcggta ccgccctgtt cggcgcccgc | 1080 |
| gactacggcg cgccggcttc ttgaatgaat ccc | 1113 |

<210> SEQ ID NO 5
<211> LENGTH: 66
<212> TYPE: DNA
<213> ORGANISM: Artificial Sequence
<220> FEATURE:
<223> OTHER INFORMATION: ARC promoter

<400> SEQUENCE: 5

| | |
|---|---|
| ctagagctat tgatgtggat caacattgtc cactagccgc tgccgcctaa tctccagaat | 60 |
| tgtgag | 66 |

<210> SEQ ID NO 6
<211> LENGTH: 2120
<212> TYPE: DNA
<213> ORGANISM: Staphylococcus aureus

<400> SEQUENCE: 6

| | |
|---|---|
| ttatttagca ggaataatta gccagattat cgagggagtt ccagggcaat ccaaacattg | 60 |
| ttatatatgc atttataaaa ttttcaagat aatttattat tcatacccett gccctttgtt | 120 |
| tcaaaattat gccctttttt tgcccttgga acaaccaca ctcctaaatt aataggtggt | 180 |
| gtggtttgat catttataat ataacataaa acaaccacc cagtaactag tatgagtggc | 240 |
| gtagcgacta taacaactct atgttatcaa gatatatgta tatgagtgat gacaaggaag | 300 |
| atgtctcctg tgagaccaac agccagatat atggcctctt gccgggctat atagttcact | 360 |
| cctactatat acacatgtaa ttataacata aaaaaataga caagtaccga agtacctgcc | 420 |
| taaataacaa caagattaac atgtgaataa tggaaataaa aagtcagccc gaaggctaac | 480 |
| ttacgaatag atgaaaattt gaacacattg ctgtgtctaa aatgattata gcataaataa | 540 |
| cgaatatttc cagctcgaaa ttaatatatt gtaataataa tatttatat ctttgttaat | 600 |
| aattatttaa ttgatttaca taaataataa ttgtaaaatt aatttgtaat cgattgcaaa | 660 |
| taagttatag gagaaaataa aatgaataaa aaactattaa caaaaacatt gatagcaagt | 720 |
| gctttagttt taacaacagt aggttcaggt tttcattctt cttcaaatta taatggtatt | 780 |
| aataacgttg aaaagctga gcaaacgaca gataacgcat tgtggaaaaa tgtaagagac | 840 |
| gctttaaaag acgcgaatat tatcgataaa acagataatg aaaatgtcaa ggttacgtat | 900 |

```
aaaatagaaa atggtggaga aaataccata gaaggaacag ttaatttaga aaatattagt    960
acttcaaaca atcctaaaat aaaccctcaa aatgttacaa aaattaatat aactagaaaa   1020
aatccgaact accctaatat tgatgctaat aatacatgga aaaaattacc agaaaaattg   1080
aaagaaaaaa atatagtgga caacggcga caatgtttca atcttaagta cagaccctaa   1140
agatgagact gtattcggta agtaggaga agataaatca aacgtaagca atagatacat   1200
caatcctaaa gatataaatg aattcaaatc actaaaaata cttttttccg aggcagatta   1260
ctcctgcctc tttctttgaa cagtgatatc ttctgatcta tgtaacactc aattacttca   1320
gattctttac ctttaacttc ctttaattca tttctctcta tctcctcaaa aagttgtgct   1380
ttttgatttg tgattggagt tgggcgtttt ttcatcgcgt tgtttcaatt ccttttaag   1440 gtattctaat tctcttctag tcatatcaat tgtttttta cttctcacct ttagtgaaat   1500
actcttatcc tttctcttct tgcgttaatg ttgctaatta gtataaaata catgcgccca   1560
tatattccaa tggtaggaca tttaattctg gattttcagc tattttcata aatctattat   1620
ctgataattt gcttaatcca attttcaagc catagcctaa attccccatc cactaagtca   1680
ttttgtttca tatggttta atctacggcc aatctcaaag atagattgac cagcgatgtt   1740
taaagtcata tttcacggat ccacatttac gataaacata tctagttaca caatattatc   1800
ccttactgca acacaggacg tttctcagcg taaaaaacac cactagaaag tgactttaaa   1860
gaatataact aattcaaact tatattaatt aatattcttt aaatgaccac tcacactttg   1920 tttttgcta tttgtaactt taaaatgttg tttgaaatct atattttttt gatatagctc   1980
cctatgtaac aaacaatttt taattaatat atatttaaac aagtcaattt agagatcggt   2040
taattcgatt catttaaata atatttatac attctatatg taaacgttta cacatttgaa   2100
gtaaggagaa ttaaaaatga                                               2120
```

<210> SEQ ID NO 7
<211> LENGTH: 177
<212> TYPE: DNA
<213> ORGANISM: Artificial Sequence
<220> FEATURE:
<223> OTHER INFORMATION: P1 pac site
<220> FEATURE:
<221> NAME/KEY: CDS
<222> LOCATION: (1)...(177)

<400> SEQUENCE: 7

```
cca cta aaa agc atg atc att gat cac tct aat gat caa cat gca ggt    48
Pro Leu Lys Ser Met Ile Ile Asp His Ser Asn Asp Gln His Ala Gly
 1               5                  10                  15 gat cac att gcg gct gaa ata gcg gaa aaa caa aga gtt aat gcc gtt    96
Asp His Ile Ala Ala Glu Ile Ala Glu Lys Gln Arg Val Asn Ala Val
             20                  25                  30 gtc agt gcc gca gtc gag aat gcg aag cgc caa aat aag cgc ata aat   144
Val Ser Ala Ala Val Glu Asn Ala Lys Arg Gln Asn Lys Arg Ile Asn
         35                  40                  45 gat cgt tca gat gat cat gac gtg atc acc cgc                       177
Asp Arg Ser Asp Asp His Asp Val Ile Thr Arg
     50                  55
```

<210> SEQ ID NO 8
<211> LENGTH: 13
<212> TYPE: DNA
<213> ORGANISM: Artificial Sequence
<220> FEATURE:
<223> OTHER INFORMATION: IHF binding site

```
<220> FEATURE:
<221> NAME/KEY: modified_base
<222> LOCATION: all "n" positions
<223> OTHER INFORMATION: n=a, c, g, or t

<400> SEQUENCE: 8
aatcaannan tta                                                              13

<210> SEQ ID NO 9
<211> LENGTH: 45
<212> TYPE: DNA
<213> ORGANISM: Artificial Sequence
<220> FEATURE:
<223> OTHER INFORMATION: DicF1 molecule

<400> SEQUENCE: 9
caggcgacag gtatagtttc tctccgattt gtgcctgtcg cctgc                            45

<210> SEQ ID NO 10
<211> LENGTH: 172
<212> TYPE: RNA
<213> ORGANISM: Artificial Sequence
<220> FEATURE:
<223> OTHER INFORMATION: ribozyme
<220> FEATURE:
<221> NAME/KEY: modified_base
<222> LOCATION: all "n" positions
<223> OTHER INFORMATION: n=a, c, g, or u

<400> SEQUENCE: 10
gcggccgcuc gagcucugau gaguccguga ggacgaaacg guacccggua ccgucagcuc            60
gagaucucun nnnnnncuga ugaguccgug aggacgaaan nnnnagaucc gucgacggau           120
cuagauccgu ccugaugagu ccgugaggac gaaacggauc ugcagcggcc gc                   172

<210> SEQ ID NO 11
<211> LENGTH: 242
<212> TYPE: RNA
<213> ORGANISM: Artificial Sequence
<220> FEATURE:
<223> OTHER INFORMATION: ribozyme
<220> FEATURE:
<221> NAME/KEY: modified_base
<222> LOCATION: all "n" positions
<223> OTHER INFORMATION: n=a, c, g, or u

<400> SEQUENCE: 11
aagcuuugga acccugauga guccgugagg acgaaacgau gacauucugc ugaccagauu            60
cacggucagc agaaugucau cgucgguucc agauccnnnn nncugaugag uccgugagga           120
cgaaannnnn nnnngcaagg gucugcgcaa cgacgacgau gagguaccac aucgucgucg           180
uugcgcacug augaggccgu gaggccgaaa cccuugacgc guuccaugc ggccgcucua            240 ga                                                                          242

<210> SEQ ID NO 12
<211> LENGTH: 14
<212> TYPE: DNA
<213> ORGANISM: Artificial Sequence
<220> FEATURE:
<223> OTHER INFORMATION: consensus ribosome binding site
<220> FEATURE:
<221> NAME/KEY: modified_base
<222> LOCATION: (8)...(11)
<223> OTHER INFORMATION: n=a, c, g, or t

<400> SEQUENCE: 12
```

```
ggaggtgnnn natg                                            14

<210> SEQ ID NO 13
<211> LENGTH: 16
<212> TYPE: DNA
<213> ORGANISM: Artificial Sequence
<220> FEATURE:
<223> OTHER INFORMATION: promoter

<400> SEQUENCE: 13
gagtcgacgg atccgg                                          16

<210> SEQ ID NO 14
<211> LENGTH: 17
<212> TYPE: DNA
<213> ORGANISM: Artificial Sequence
<220> FEATURE:
<223> OTHER INFORMATION: promoter

<400> SEQUENCE: 14
tgggggtggg ggtgggg                                         17
```

TISSUE-SPECIFIC AND PATHOGEN-SPECIFIC RIBOZYMES

CROSS-RELATED APPLICATIONS

This is a continuation of U.S. application Ser. No. 09/548,449, filed Apr. 13, 2000, now abandoned which is a continuation-in-part of U.S. application Ser. No. 09/291,902, filed Apr. 14, 1999, now U.S. Pat. No. 6,271,359. The disclosures of these prior applications are considered part of (and are incorporated by reference in) the disclosure of this application.

1. INTRODUCTION

The present invention relates to the discovery, identification, and characterization of toxic agents which are lethal to pathogens and methods for targeting and delivering such toxic agents to a pathogen or pathogen infected cell in order to treat and/or eradicate an infection. In particular, the present invention relates to toxic agents which target bacteria at different stages of the bacterial life cycle, which are delivered alone or in combination to bacteria or bacteria-infected cells. In particular, the invention relates to a phage delivery vehicle approach for the treatment of bacterial infections in humans and animals. The invention also relates to toxic agents which are lethal to diseased cells and methods for targeting such toxic agents to a diseased cell in order to treat and/or eradicate the disease. The present invention relates to promoter elements which are pathogen-specific. The invention also relates to promoter elements which are used to achieve pathogen-specific or tissue specific expression of the toxic agent(s) and/or ribozyme(s) of the present invention. Specifically, the invention relates to the delivery of one or more toxic gene products, antisense RNAs, or ribozymes, or combination thereof. The invention provides a novel system by which multiple pathogenic targets may be simultaneously targeted in order to kill a pathogen or pathogen-infected cell or render it less fit. Further, the invention has important implications in the eradication of drug-resistant bacterium and bacterial pathogens. The invention provides a novel system by which multiple targets may be simultaneously targeted to cause the death of a diseased cell or render it less fit. The invention has important implications in the eradication of drug-resistant pathogens (such as antibiotic resistant bacteria) and drug-resistant diseased cells (such as drug-resistant cancer cells).

2. BACKGROUND

2.1. Antimicrobial Agents

Infectious diseases sicken or kill millions of people each year. Each year in the United States alone, hundreds of thousands of people are infected with resistant bacterial strains that are no longer treatable with drugs like penicillin and vancomycin (Hiramatsu et al, 1997, Morbidity and Mortality Weekly Report 46:624-26). Infections associated with antimicrobial resistance include those acquired in hospitals (nosocomial), such as pneumonia particularly in the young, elderly and immunocompromised), typhoid fever, bacterial meningitis, and tuberculosis. Around the world, nearly 1.5 billion people carry various types of the tuberculosis bacteria and depending on the country, up to 40 percent have proven to be resistant to antibiotics (see, Boyce et al, 1997, Epidemilogy and prevention of nosocomil infections. In The *Staphylococcus* in Human Disease. Crossley and Archer Eds, Chruchill Livingston Inc., New York, N.Y.). It is estimated that in some developed countries, up to 60% of all nosocomial infections result from bacteria resistant to antibiotics. For example, *Pseudomonas aeruginosa*, is of the most common gram-negative bacterium associated with nosocomial infections and outbreaks in burn units. Infections by this organism are associated with high mortality (60%), which is attributed to the high intrinsic resistance of members of this genus to many structurally unrelated antibiotics. Gram-positive bacteria also have a significant impact on infectious diseases. For example, *Staphylococcus aureus*, is a Gram-positive organism which is responsible for about 260,000 hospital acquired infections in the United States which subsequently causes between 60,000 and 80,000 deaths annually (see, Boyce et al, supra).

Although, numerous antimicrobial therapies have been designed to target one or several infectious agents, many therapies show varying degrees of success in eradicating infection. Only a very limited number of new antibiotics have come onto the market in the last decade, yet the number of deadly bacteria that are resistant to these drug therapies has soared. For example, vancomycin is one of the last effective antimicrobial available for the treatment of methicillin-resistant *S. aureus* infection (MRSA). However, vancomycin resistant isolates *S. aureus* have now emerged (Hiramatsu et al, 1997, Morbidity and Mortality Weekly Report 46:624-26). Additionally, the failure of many of these therapies to target specific infectious agents has lead to overuse or inappropriate use of the therapies, which in turn has lead to the development of drug resistant microbes. The development of drug resistance in many infectious agents has reduced the efficacy and increased the risk of using the traditional antimicrobial therapies.

Accordingly, there is need in the art for novel molecules and novel combinations of molecules that can act as lethal agents in bacteria and which may be delivered to a pathogen, without causing toxicity to the infected host. Further, there is a need in the art for novel methods of targeting particular species of pathogens while leaving the host's beneficial flora intact. The present invention provides such novel products, therapeutics, and methods for delivery which may be used as toxic agents against pathogens such as bacteria.

2.2. Antisense

Antisense technology seeks to use RNA molecules which are complementary to (or antisense to) a cellular RNA, for the purpose of inhibiting a cellular RNA from being translated into the encoded protein. In this way, the expression of a specific protein is targeted for down regulation. However, a large number of difficulties exist in the art surrounding antisense technology. Commonly, delivery of an exogenous antisense molecule to the target cell is difficult or impossible to achieve. Further, antisense molecules do not consistently lead to a decrease in protein expression. For example, it has been shown that the expression of antisense RNA in transgenic mice did not invariably lead to a reduction in target RNA molecules, and when reduction in target RNA molecules did occur, it was not predictably paralleled by a reduction in protein. Even when protein levels were reduced sometimes no biological effect was detected (Whitton, J. Lindsay "Antisense Treatment of Viral Infection" *Adv. in Virus Res*. Vol. 44, 1994). Thus, there is a need in the art for a delivery system in which antisense molecules may be efficiently delivered to a target cell such as a bacterial pathogen.

2.3. Ribozymes

A ribozyme is a catalytic RNA molecule that cleaves RNA in a sequence specific manner. A key technical concern in the use of ribozymes as antimicrobial agents is that the ribozyme must be introduced into and expressed by the targeted microbe so that the ribozyme(s) can cleave the targeted RNA(s) inside the microorganism. A second important concern is the tight coupling of transcription and translation in microorganisms which can prevent binding to and cleavage of the bacterial RNA targets. Additionally, bacterial RNAs often have a shorter half life than eukaryotic RNAs, thus lessening the time in which to target a bacterial RNA. The invention described herein addresses these concerns and proves novel therapeutic treatments of bacterial infections using combinations of ribozymes and toxic agents.

3. SUMMARY OF THE INVENTION

The present invention provides toxic agents and methods for specifically targeting toxic agents to bacteria or bacteria-infected cells or other pathogens. Toxic agents of the present invention are directed to one or more targets and thus can be used alone or in combination to eradicate bacteria. The invention relates to the delivery of toxic gene products or the combination of ribozmes and toxic gene products for the eradication of a pathogen or diseased cell. Specifically, the invention provides the delivery of one or more toxic proteins, antisense RNA, multi-ribozymes, or nucleic acids encoding the same, or a combination thereof, to a cell, tissue, or subject containing an infectious bacteria or pathogen in order to eradicate such bacteria or pathogen.

The present invention further encompasses the use of a toxic agent and/or ribozymes of the present invention for the treatment of disease, viral infection, parasitic infection and microbial infection. The present invention further relates to a method of treating a subject having a proliferative disease of a specific tissue by inhibiting cell proliferation in the tissue, comprising administering to the subject a toxic agent and/or ribozyme operably linked to a tissue-specific promoter sequence, which promoter is specific for the diseased tissue, and whereby the ribozyme and/or toxic agent encoded by the nucleic acid is expressed, cell proliferation is inhibited, and the proliferative disease is treated.

The present invention further relates to a method of treating a subject having a pathogenic infection or disease, by inhibiting replication of the pathogen, comprising administering to the subject a toxic agent and/or ribozyme operably linked to a pathogen-specific promoter, whereby the ribozyme and/or toxic agent encoded by the nucleic acid is expressed, the pathogen is inhibited from replicating or is killed or rendered less fit, and the infection or disease is treated. In specific embodiments of the invention, the toxic agents of the invention are useful to treat microbial infections associated with severe burns, cystic fibrosis, cancer, or other immunocompromising conditions. The present invention encompasses the toxic agent(s) and/or ribozyme(s) of the present invention in pharmaceutical formulations.

The present invention further encompasses the use of the toxic agents and/or ribozymes of the present invention for research and screening purposes. In one embodiment of the present invention, the ribozymes and/or toxic agents may be used to screen for viral, microbial, prokaryotic, or eukaryotic gene products or molecules to be targeted in order to effectively inhibit the selected virus or microbial agent or selected cell.

In yet another embodiment, the present invention relates to a novel vector encoding the toxic agent(s) and/or ribozyme(s). The novel vectors of the present invention may be used to engineer a wide variety of toxic agents and/or ribozymes including, but not limited to, tissue-specific, pathogen-specific, promoter-specific, antimicrobial specific, antiviral specific, anticancer specific, antitumor specific, or target-specific.

In one embodiment, the invention relates to toxic agents which specifically target gene products essential for the survival or life cycle of a pathogen (such as replication, packaging, etc). In one embodiment, the present invention relates to naturally occurring bactericidal addiction system toxins which have been modified to be expressed in the absence of their corresponding addiction system antidote. In another embodiment, the present invention relates to naturally occurring addiction system toxins which have been modified to be expressed at higher levels than their corresponding addiction system antidote. In one example, an addiction system toxin (e.g., doc, chpBK, kicB, or gef) is used as a toxic agent and is uncoupled from its antidote. In specific embodiments, the invention provides for delivery of toxic agents such as bactericidal proteins (or nucleic acids encoding such toxic agents) by a bacteriophage delivery system. In other specific embodiments, the invention provides novel transfer plasmids encoding toxic agents which may be used in combination with a bacteriophage delivery system in order to treat a bacterial infection in a host.

The invention also relates to antisense RNA which targets essential nucleotide sequences, such as DicF1 or a DicF1-like antisense molecule that specifically target a nucleotide sequence encoding a protein essential for replication or survival. Further, the invention relates to modified antisense structures with increased stability which act as lethal agents when expressed in bacteria. The invention also relates to toxic sense molecules designed to target essential antisense molecules.

The present invention relates to multi-ribozymes and their use to target RNA in a tissue-specific or pathogen-specific manner for the treatment of disease (such as pathogen infection or cancer). The invention provides multi-ribozymes containing one or more internal trans-acting ribozyme. Transacting ribozymes act in a target-specific manner and therefore may act as a toxic agent to a pathogen (such as bacteria) or a selected cell (such as a diseased cell). In accordance with the present invention, the multi-ribozyme may comprise a) a trans-acting ribozyme flanked by 5' and 3' autocatalytically cleaving ribozymes or enhanced autocatalytically cleaving ribozymes; b) a trans-acting ribozyme flanked by either a 5' or 3' autocatalytically cleaving ribozyme; or c) multiple trans-acting ribozymes, flanked by one or both 5' and 3' autocatalytically cleaving ribozymes or enhanced autocatalytically cleaving ribozymes. Multi-ribozymes of the invention may also be used to deliver one or more toxic agents to a pathogen cell or tissue. Ribozymes useful in the present invention include those described in U.S. Pat. No. 5,824,519 and PCT publications No. WO98/24925, WO97/17433, WO98/24925, WO99/67400, which are incorporated by reference herein in their entirety. In accordance with the present invention the multi-transacting ribozymes may be targeted to the same site on the same RNA, different sites on the same RNA or different RNAs. In accordance with the present invention the multiple toxic agents may be targeted to the same site on the same target (such as a cellular RNA or protein), different sites on the same target or different targets. For example, in certain embodiments a toxic agent (such as an antisense nucleic acid or nucleic acid encoding a toxic protein) may be engineered into a multi-ribozyme in place of a trans-acting ribozyme, or in addition to a trans-acting ribozyme. In this embodiment, the toxic agent is flanked by a 5' and/or 3' autocatalytically cleaving ribozyme.

The invention additionally provides nucleic acids and expression cassettes which encode the toxic agent and/or ribozymes of the invention. These nucleic acids can be used to express the toxic agent(s) and/or ribozyme(s) of the invention at the selected site.

At the molecular genetic level the coding sequence for a toxic agent, ribozyme, or multi-ribozyme of the invention may be placed under the control of one or more of the following genetic elements: a naturally occurring strong, intermediate, or weak constitutively expressed or regulated promoter from the targeted microorganism, or an artificially contrived constitutively expressed or regulated promoter containing either a strong, intermediate or weak consensus sequence that accords the desired levels of ribozyme and/or toxic agent expression. The present invention relates to promoter elements which are pathogen-specific. The invention relates to promoter elements which are used to achieve pathogen-specific expression of the toxic agents of the present invention. The present invention also relates to promoter elements which are tissue-specific. The invention relates to promoter elements which are used to achieve tissue-specific expression of the toxic agents of the present invention.

In one embodiment, the nucleic acids comprise a tissue-specific promoter operably linked to a sequence encoding one or more toxic agent(s). In another embodiment, the nucleic acids comprise a pathogen-specific promoter operably linked a sequence encoding one or more toxic agent(s). In accordance with the present invention, toxic agents of the invention may act on the same or different targets.

The present invention relates to a toxic agent and/or a trans-acting ribozyme which targets any cellular, viral, bacterial, fungal, or other single cellular or multicellular organism from any known taxonomic family, genus, or species. Another embodiment of the invention relates to a toxic agent which is lethal or toxic to a pathogen such as a bacteria, fungus, yeast, diseased cell.

The targets of the antimicrobial ribozyme therapeutics described herein are the RNAs of invading or normal flora microorganisms. The targets of the antimicrobial toxic agent therapeutics described herein include RNAs, proteins, genes and other molecules of invading or normal flora microorganisms. The invention provides the delivery of a series of ribozymes and/or toxic agents directed towards essential, housekeeping, or virulence genes of one or a series of candidate microorganisms. Inactivation of essential proteins and virulence determinants render the invading microbes inactive or slow their growth, while at the same time, the essential processes of the host are not significantly affected.

The present invention also relates to the delivery of the toxic agents of the invention to cell or pathogen by abiologic or biologic systems. In a specific embodiment, a toxic agent of the invention is delivered to a bacterial cell by a modified bacteriophage capable of infecting a pathogenic bacteria. In a further embodiment, bacteriophage are selected for their ability to infect a particular species or genera of bacteria, and are used to deliver a toxic agent for the eradication of such bacterial species or genera from a host. In a preferred embodiment, the delivery vehicle or nucleic acids native to the delivery vehicle are modified such that they contain insufficient genetic information for the delivery of nucleic acids native to the delivery vehicle. Thus, the modified delivery vehicle (e.g., virion or bacteriophage) can serve as a molecular vehicle that delivers the ribozyme(s) and/or toxic agent(s) of the invention to the target cell or pathogen, but does not deliver replicable nucleic acids native to the delivery vehicle. Alternatively, an abiologic delivery system (e.g., liposomes) can be used to package nucleic acid carrying the genetic elements necessary and sufficient for the proper expression of the ribozyme(s) and/or toxic agent(s). In one embodiment, delivery of a toxic agent to a pathogen is by use of a bacteriophage or other delivery vehicle which targets the pathogen of interest. In one embodiment, a recombinant bacteriophage delivers the toxic agent or nucleic acids encoding the toxic agent to the pathogen.

The present invention provides compositions of matter which has resulted from the development of methods and compositions for the delivery of one or more ribozymes and/or toxic agents directed against fundamental and essential cellular processes specific to a targeted microorganism through an inactivated, altered, virus (virion), bacteriophage, or abiologic delivery vehicles, capable of delivering a nucleic acid comprising the toxic agent(s) and/or ribozyme(s) into the targeted microorganism. The microorganisms may be any virus, nonvirus, bacterium, or lower eukaryotes such as fungi, yeast, parasites, protozoa, or other eukaryotes that may be considered pathogens of humans, animals, fish, plants, or other forms of life. Thus, the invention has important implications in human and veterinary medicine.

In certain preferred embodiments, a toxic agent of the invention is used as an antimicrobial therapeutic. A toxic agent may be used alone, or in combination with one or more other toxic agents. Thus, delivery of a toxic agent to an invading microorganism, kills or render it less fit. A toxic agent may also be used in combination with one or more ribozymes. Further, a combination of ribozymes and toxic agents may be used as an antimicrobial therapeutic.

The toxic agent approaches of the invention offer advances for antimicrobial therapeutics including but not limited to: (1) the bypass of de novo or built-in drug resistance, which sophisticated microbes may have or develop (2) the decreased ability of cells to counteract ribozymes or toxic agents delivered into them, (3) the use of broad RNA targets and non-RNA targets available in microbes that can be attacked in simultaneously (4) the flexibility of custom design of the present delivery vehicle can be readily tailored to different families of organisms or different species of organisms, (5) the ease of assembly construction and manufacture of the modified delivery vehicle, (6) the availability of a variety of methods of administration of the pharmaceutical preparations of the invention such as topically, or via injection, inhalation, or ingestion, etc. (7) the ability to lyophilize the pharmaceutical preparation and thus confer stability to the antimicrobial therapeutic, (8) the reduced immunogenicity of the therapeutic preparations, and (9) the availability of animal test systems that enable the evaluation of the ribozymes and/or toxic agents of the invention. Therefore, the unique delivery approach and an aggressive mechanism for depriving the pathogen essential or important gene products can achieve the timely defeat of pathogen within the infected host. Accordingly, the invention has important implication in the eradication of drug-resistant pathogens.

4. BRIEF DESCRIPTION OF THE FIGURES

FIG. 1A Diagram depicts the components of the lacI-regulated broad spectrum promoter.

FIG. 1B The sequence of the LEASHI promoter (SEQ ID NO:1).

FIG. 1C The sequence of a modified rrnB promoter (SEQ ID NO:2).

FIG. 1D The sequence of the Anr promoter (SEQ ID NO:3).

FIG. 1E The sequence of the Proc promoter (SEQ ID NO:4).

FIG. 1F The sequence of the Arc promoter (SEQ ID NO:5).

FIG. 1G The sequence of the TSST-1 promoter (SEQ ID NO:6).

Figure 2:
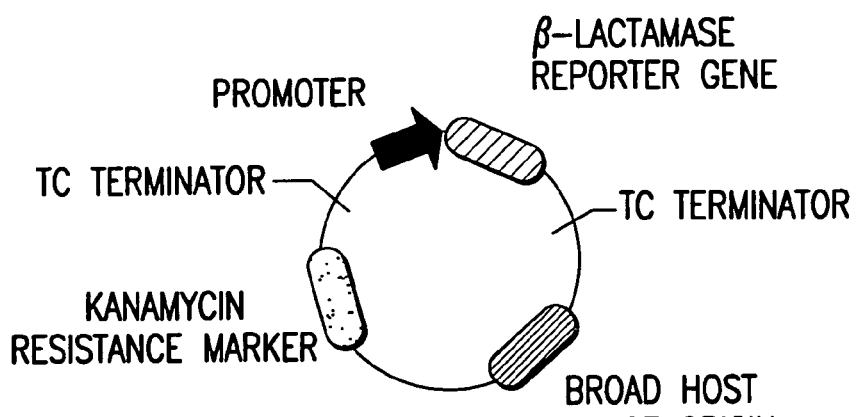

FIG. 2 Diagram of a β-lactamase reporter plasmid.

Figure 3A:
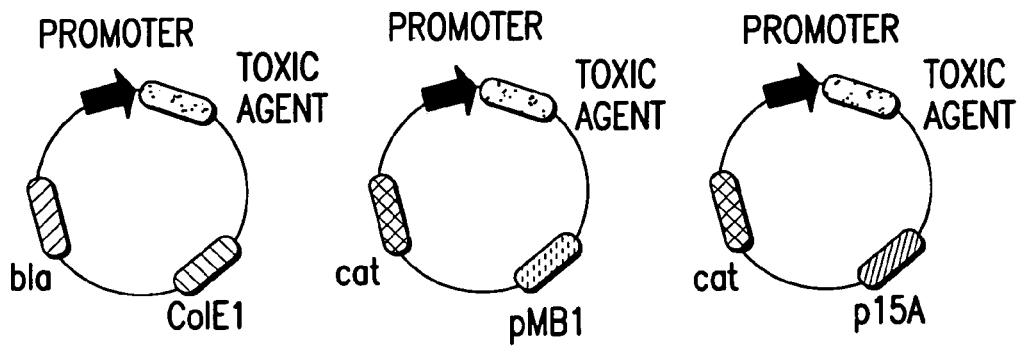
Figure 3B:
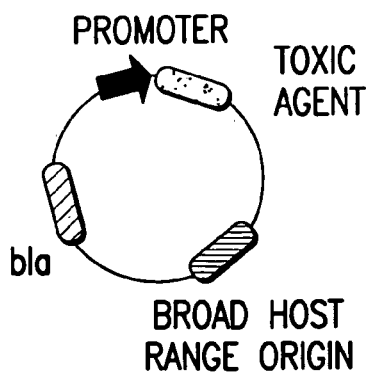

FIG. 3A-B Expression vectors for cloning Toxic Agents.

Figure 4:
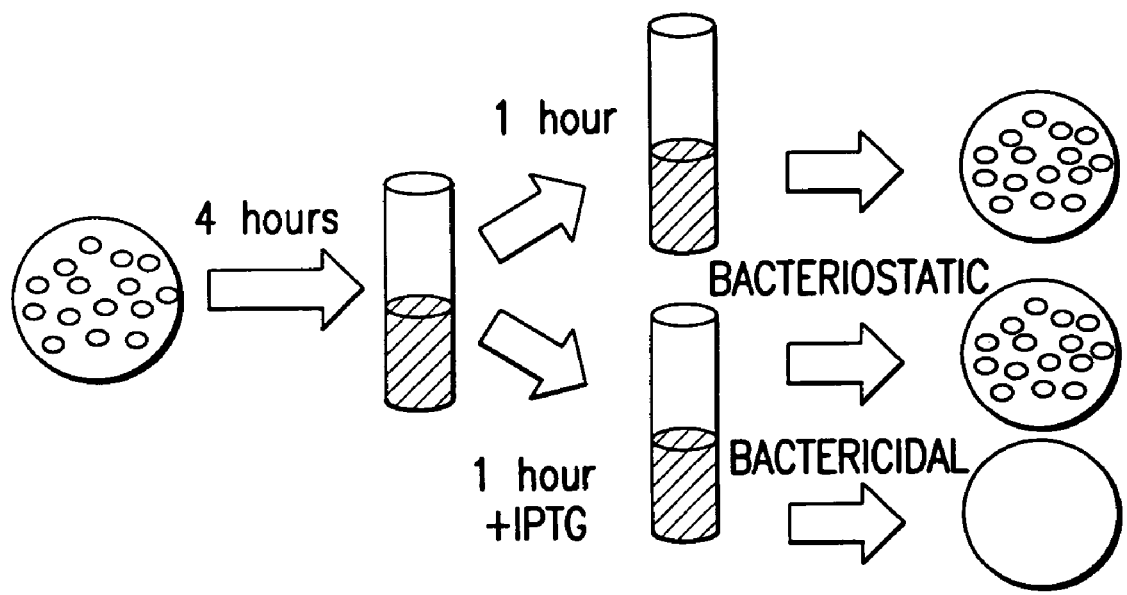

FIG. 4 Assay for lethality of Toxic Agents

Figure 5A:
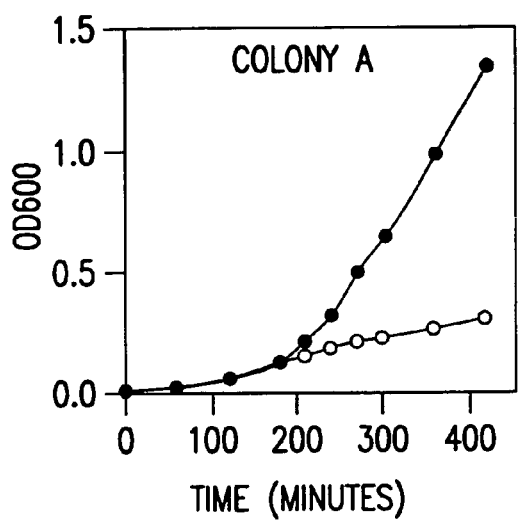
Figure 5B:
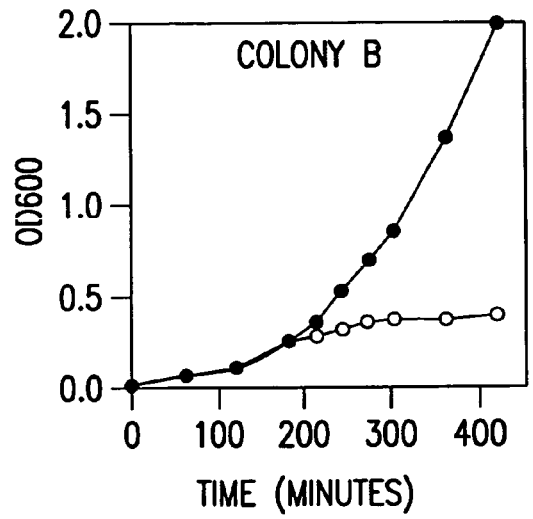
Figure 5C:
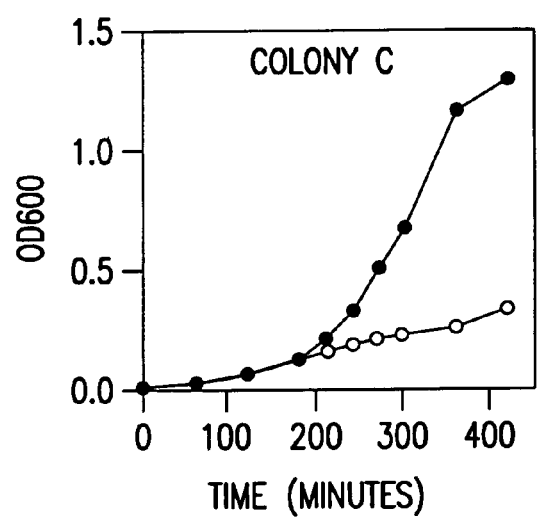

FIG. 5 Growth of $E.\ coli$ harboring a doc expression plasmid.

Figure 6A:
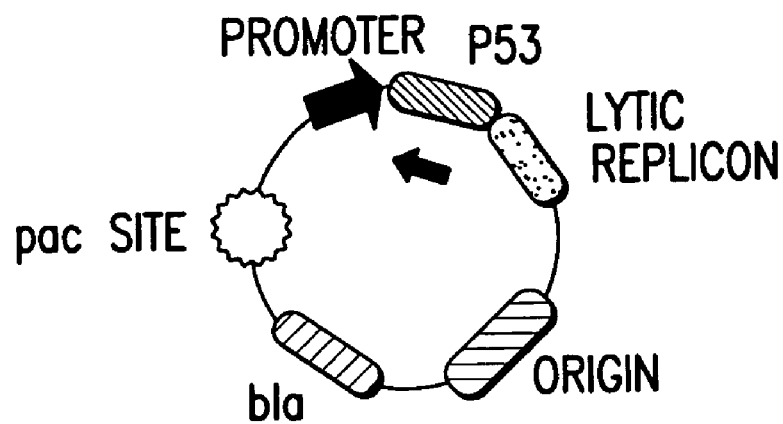
Figure 6B:
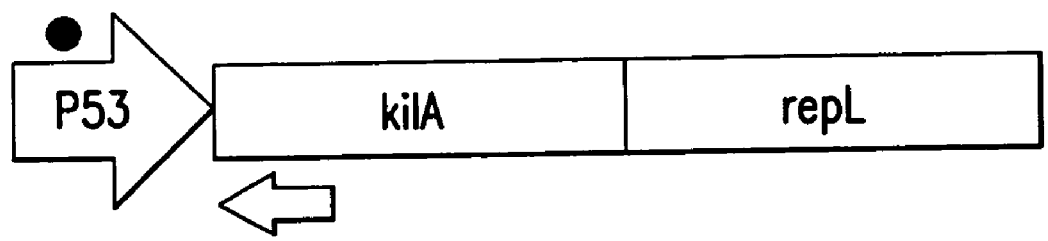

FIG. 6A-B Structure of a Transfer Plasmid.

Figure 7:
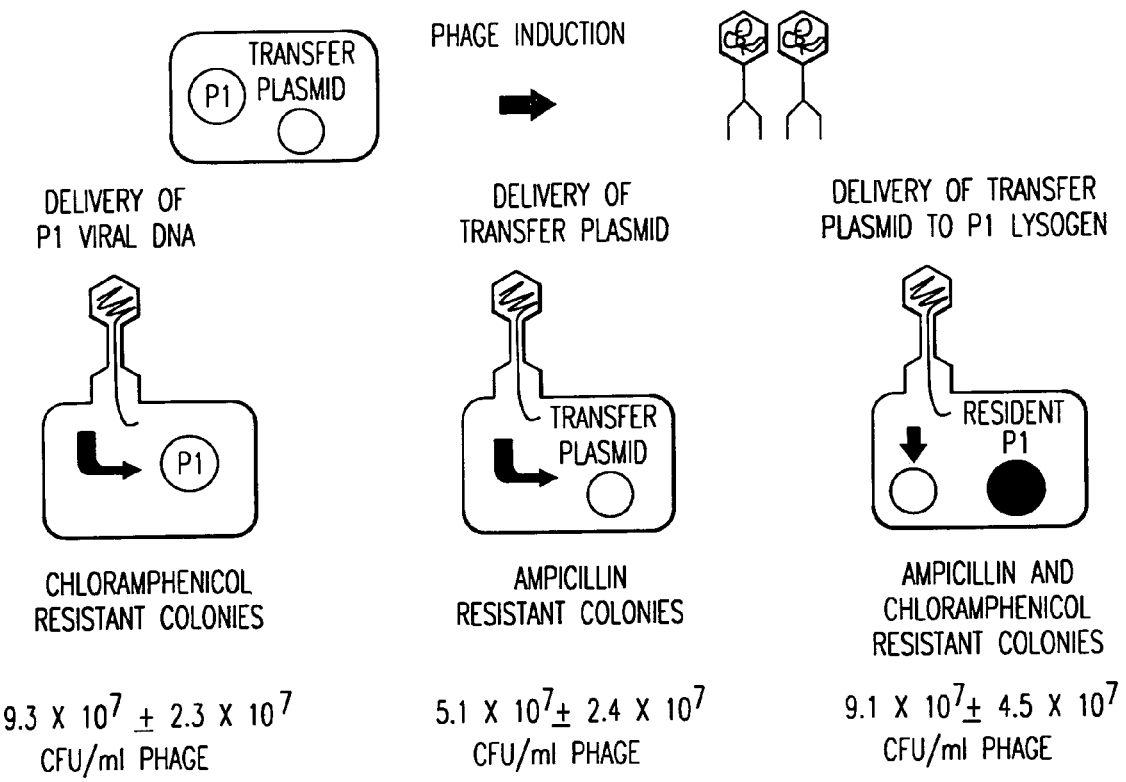

FIG. 7 Delivery Efficiency of the Transfer Plasmid by the P1 bacteriophage vehicle to $E.\ coli$.

Figure 8:
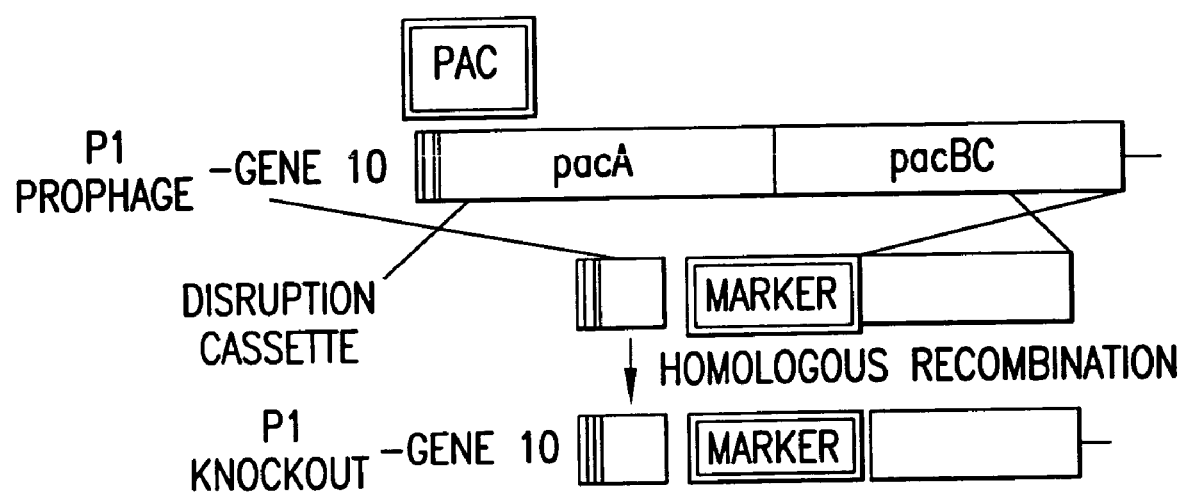

FIG. 8 Scheme for generation of the P1 pac site knockout.

Figure 9A:
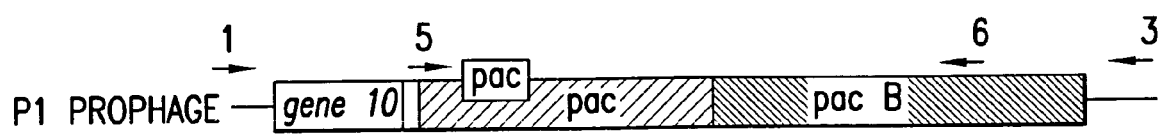
Figure 9B:
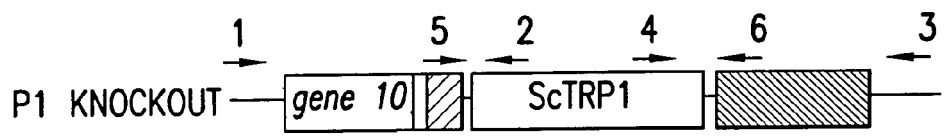
Figure 9C:
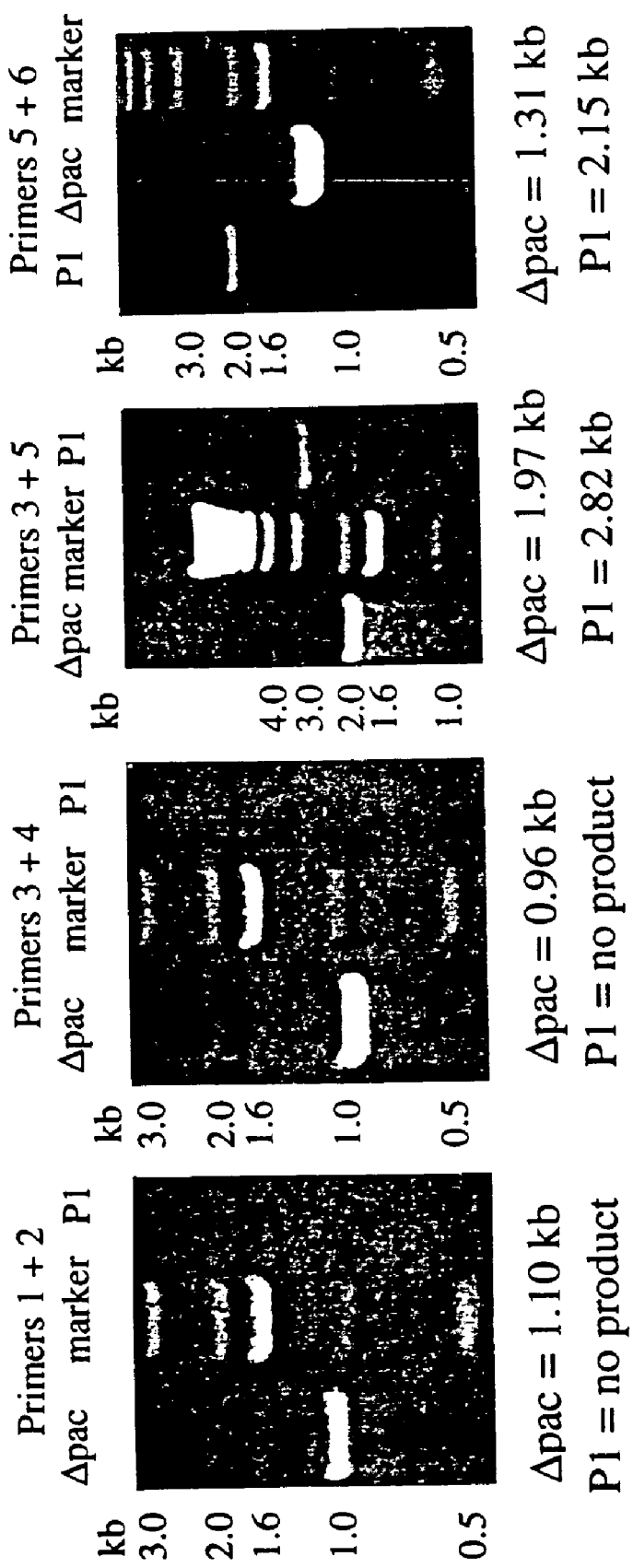

FIG. 9 Identification and confirmation of the P1 pac site knockout by PCR screening.

Figure 10:
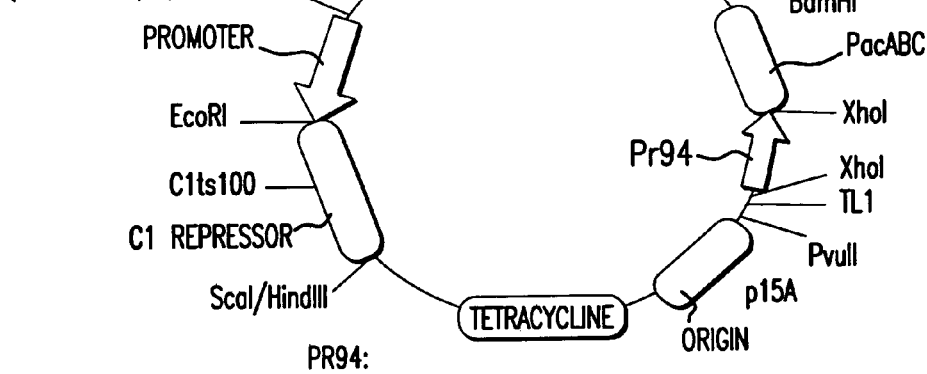

FIG. 10 Diagram of the pacABC Complementing plasmid.

FIG. 11 Recombination between the P1 pac mutant and the pacABC Complementing plasmid.

FIG. 12 Sequence of the minimal P1 pac site (SEQ ID NO:7).

Figure 13:
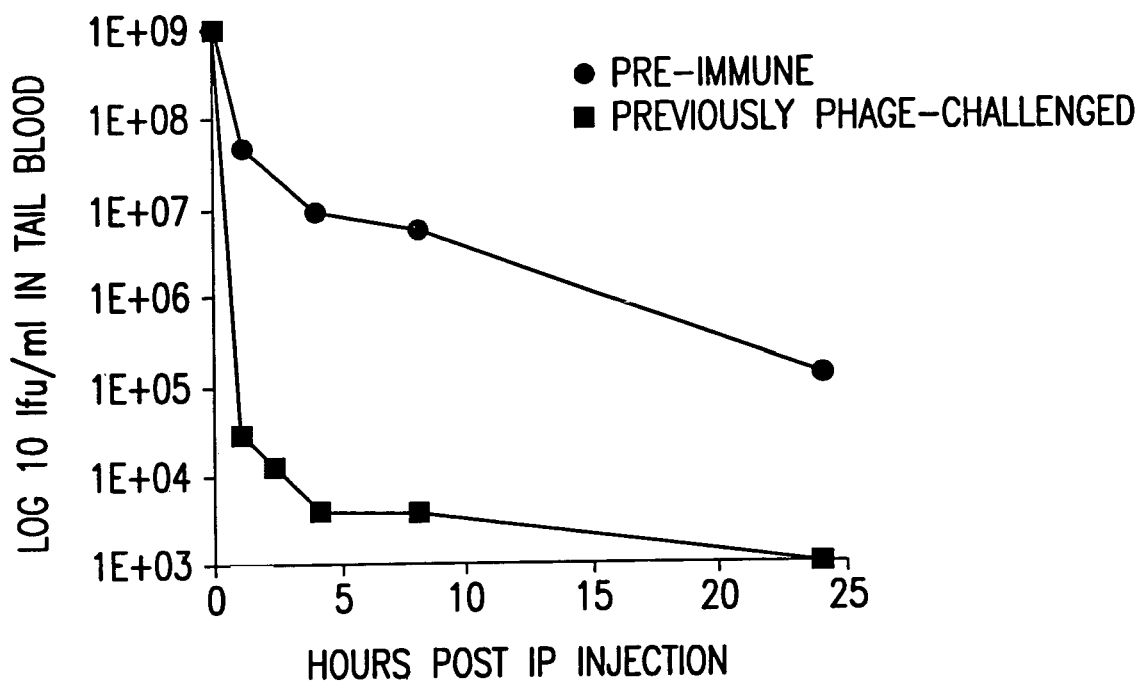

FIG. 13 Immunogenicity of replicating phage in mice.

Figure 14:
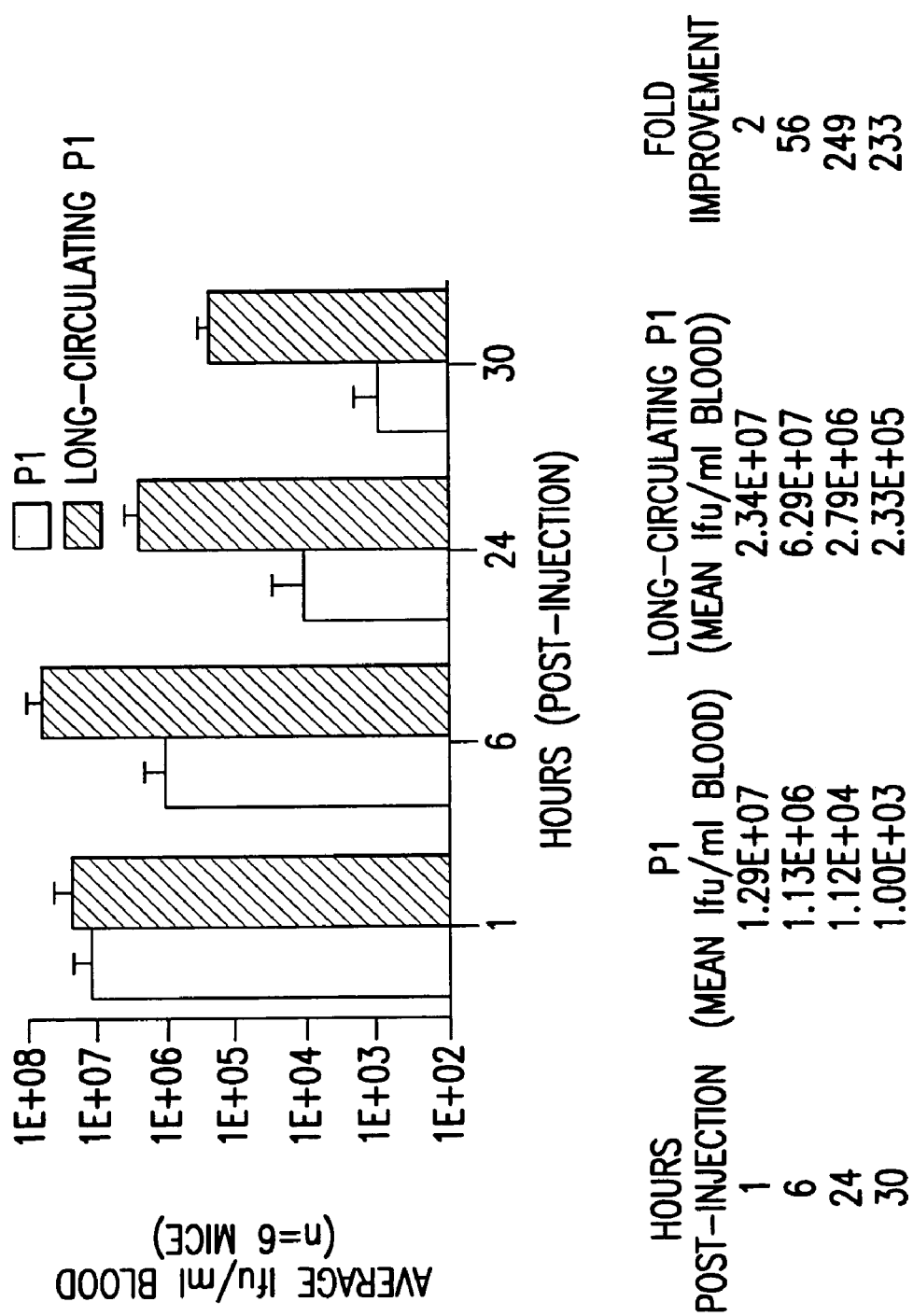

FIG. 14 Comparison of original and long-circulating P1 phage persistence in vivo.

Figure 15:
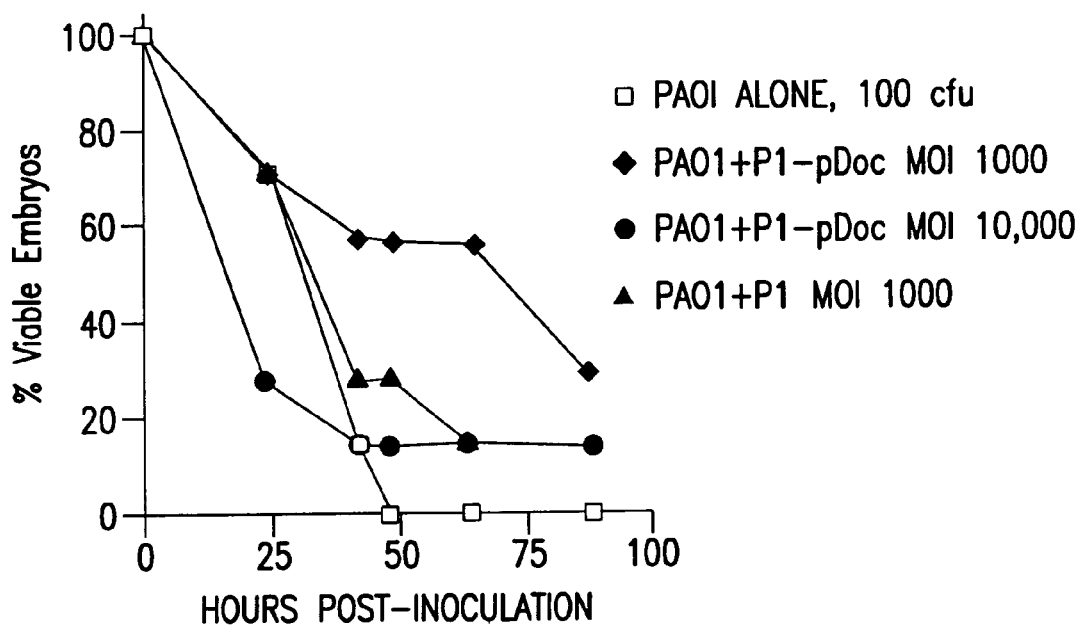

FIG. 15 Treatment of $P.\ aeruginosa$ (PA01) infections in embryonated hen eggs.

Figure 16:
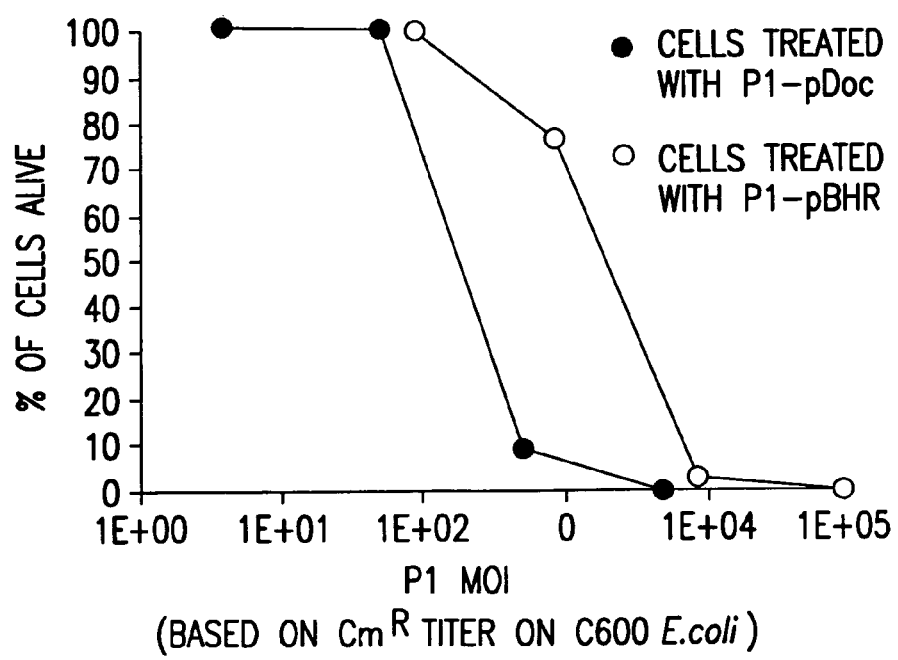

FIG. 16 In vitro killing of $E.\ coli$ EC-4 bacterial cells.

Figure 17:
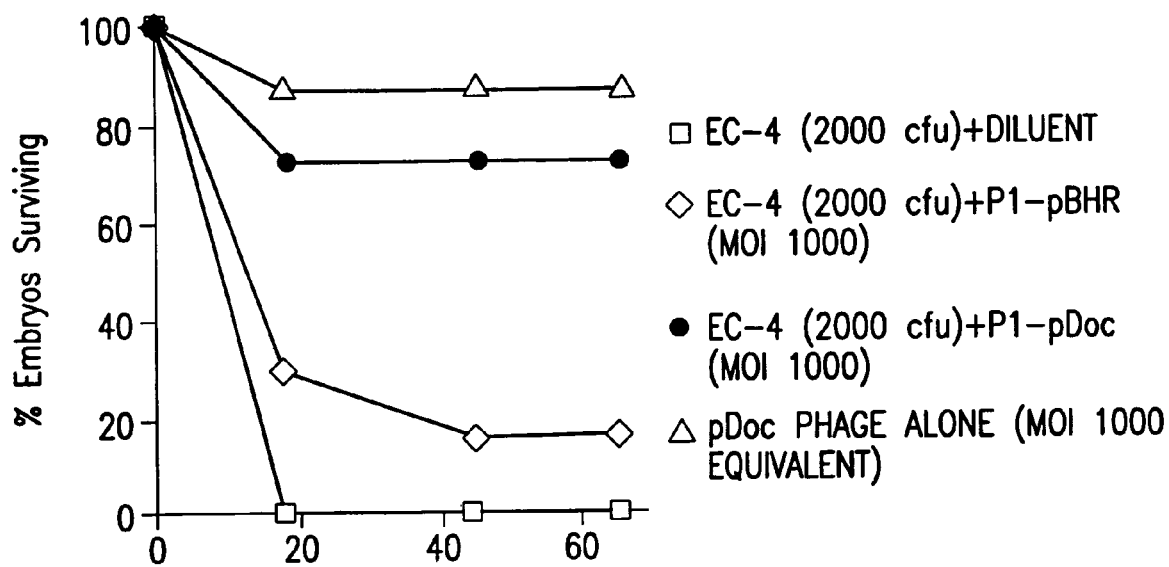

FIG. 17 Treatment of $E.\ coli$ EC-4 infection in embryonated hen eggs.

Figures 18, 19:
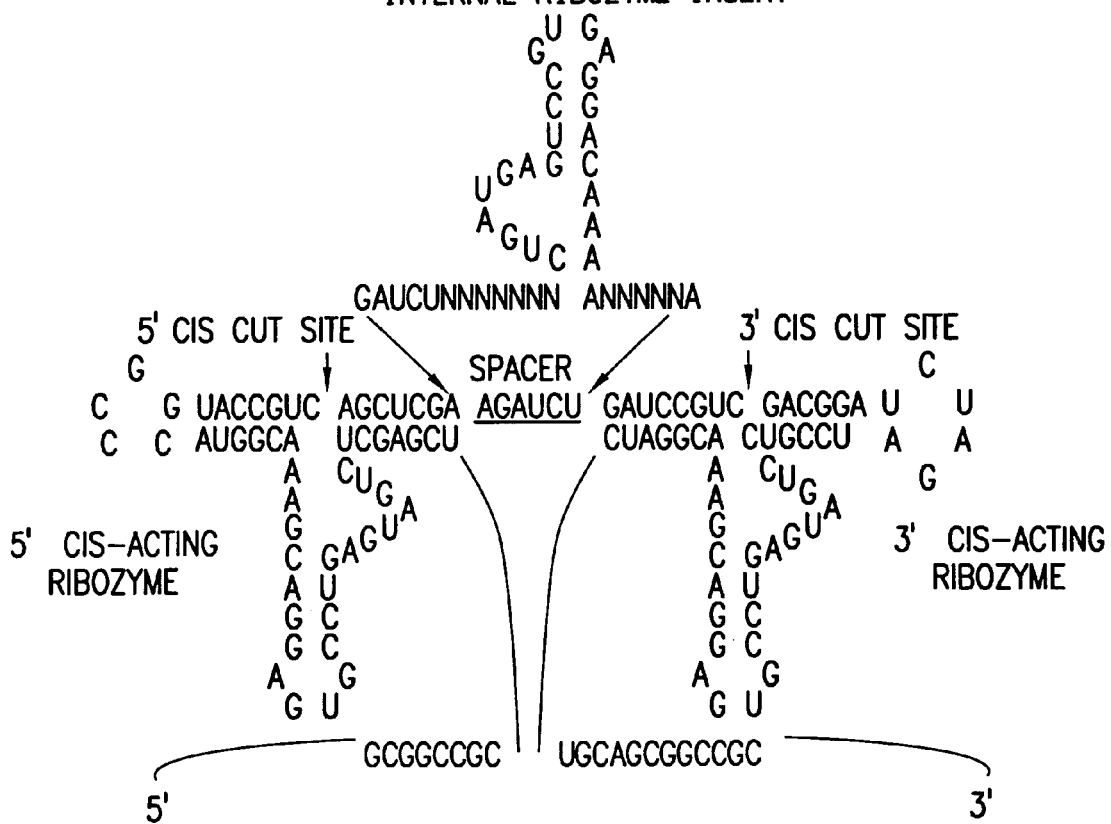

FIG. 18 Sequence of the DicF1 molecule (SEQ ID NO:9).

FIG. 19 Diagram and nucleotide sequence of the pClip ribozyme cassette (SEQ ID NOs: 15 and 16).

Figure 20:
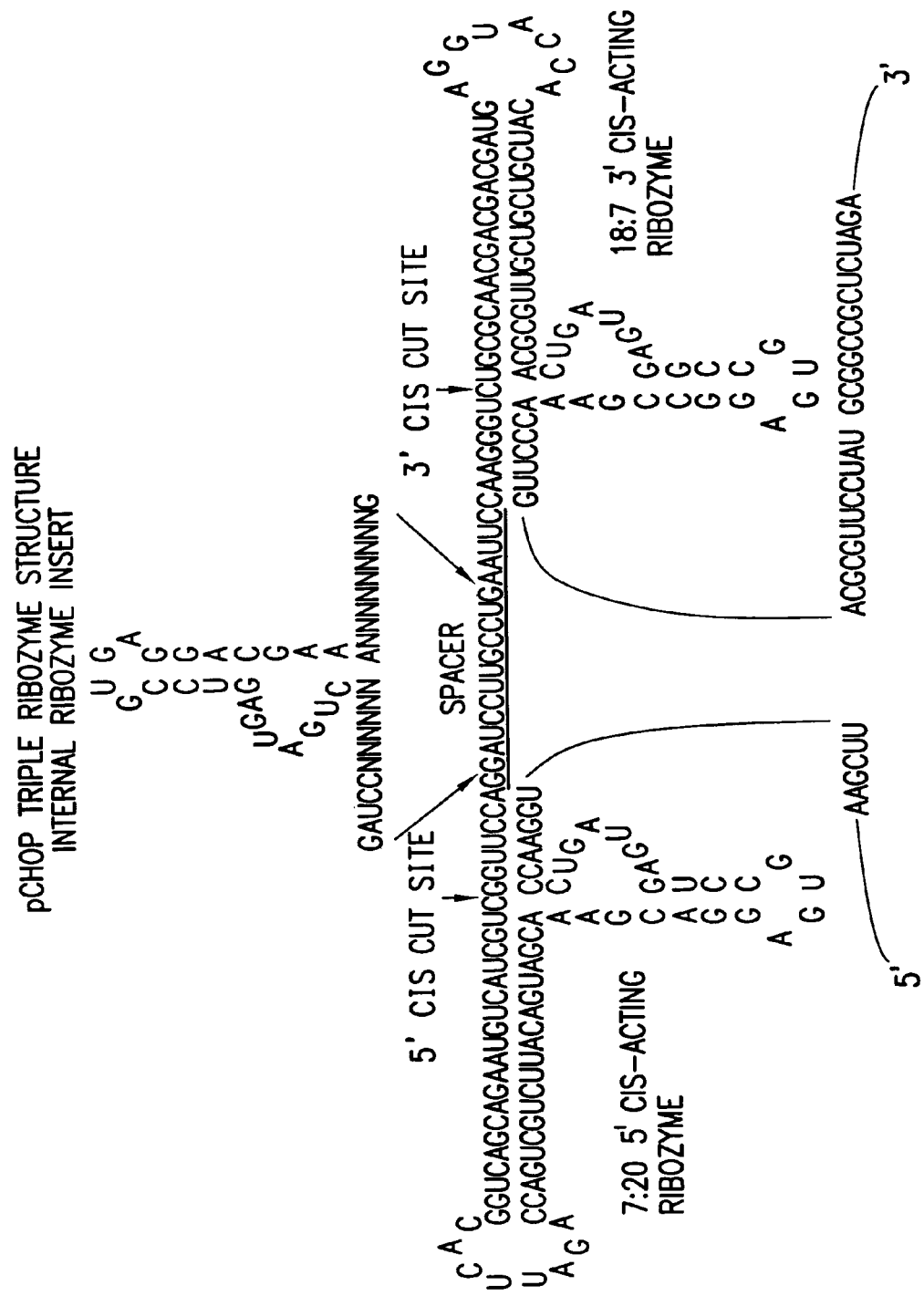

FIG. 20 Diagram and nucleotide sequence of the pChop ribozyme cassette (SEQ ID NOs: 17 and 18).

Figure 21:
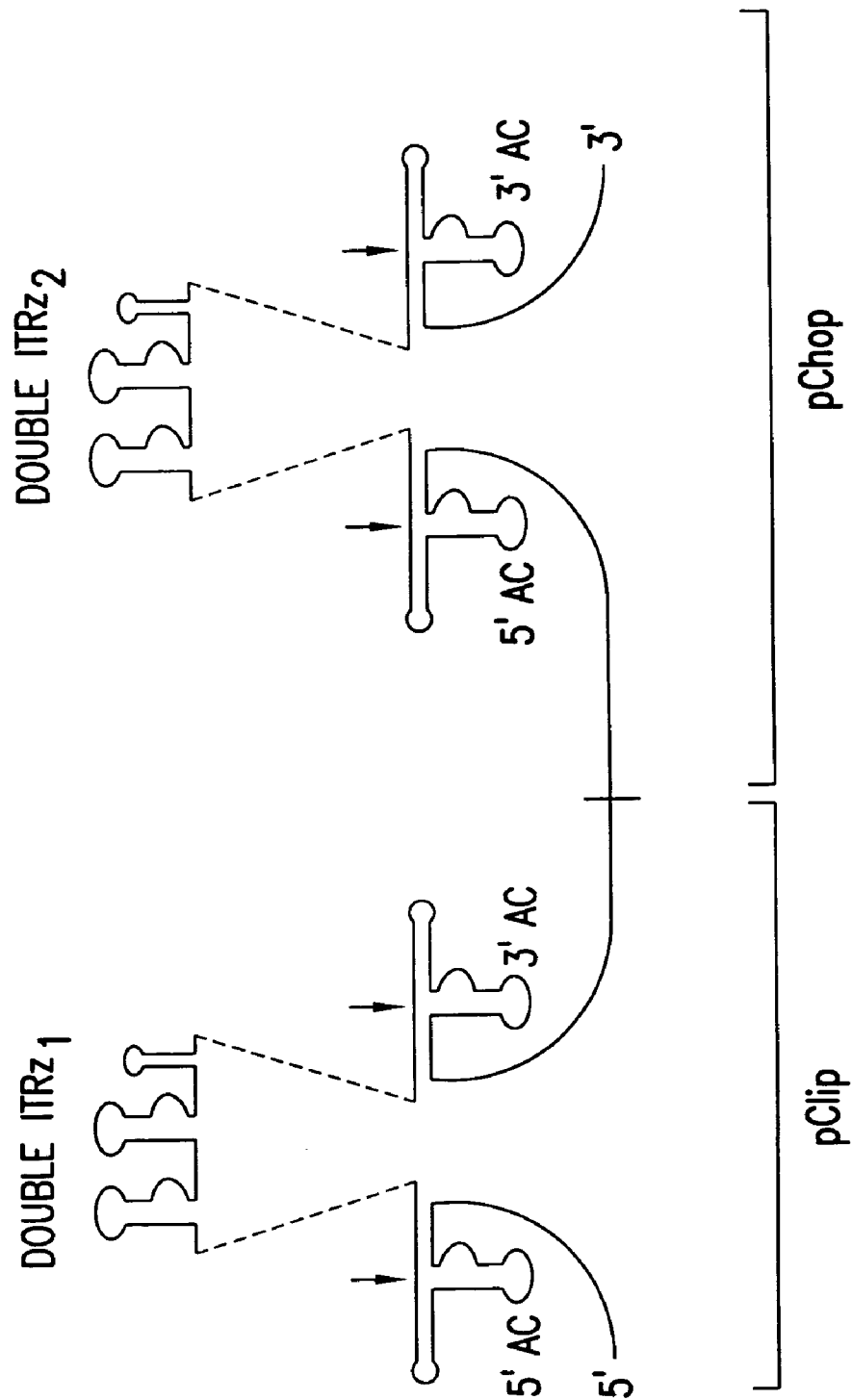

FIG. 21 Schematic diagram of the pSnip ribozyme cassette. pSnip includes sequences of the pClip triple ribozyme cassette, catalytic core targeted ribozymes comprising two linked trans-acting ribozymes, and sequences from the pChop triple ribozyme cassette.

FIG. 22A A schematic of DNA encoding the ribozyme used in the molecular sequence of events in ribozyme maturation and action.

FIG. 22B The primary RNA transcript. Autocatalytic cleavage takes place upon completion of transcription.

FIG. 22C The release of the trans-acting ribozyme. As a direct result of cleavage of the two cis-acting ribozymes, the internal ribozyme containing a reverse and complementary sequence to the mRNA target is released.

FIG. 22D The sequence specific hybridization of the ribozyme. The internal or trans-acting ribozymes comprise two trans-acting ribozymes linked by a short nucleotide "spacer". Each of the two trans-acting ribozymes contain a sequence that is reverse complementary to the targeted message of the same or at different sites. The ribozyme is synthesized at a concentration sufficient to locate and hybridize to all or substantially all targeted transcripts.

FIG. 22E The trans-catalytic cleavage. Upon hybridization of the internal trans-acting ribozyme to the targeted mRNA transcript, the internal ribozyme achieves a catalytic topology and cleaves the targeted message. Upon cleavage the trans-acting ribozyme is released and its activity and function are recycled.

5. DETAILED DESCRIPTION OF THE INVENTION

The present invention provides toxic agent(s) and/or ribozyme(s) and their use in a tissue-specific, target-specific, or pathogen-specific manner for the treatment of disorders and disease related to bacterial, parasitic or viral infections or to cellular proliferation, and cancers. The ribozymes and/or toxic agents of the present invention may be engineered to target one or more specific RNAs contained in a specific cell or tissue in the host. The ribozymes of the present invention may also be engineered to target one or more specific RNAs encoded by a specific pathogen, virus, or microbial agent. The toxic agents of the present invention may also be engineered to target one or more specific RNAs, proteins, or molecules of a specific pathogen, virus, or microbial agent.

The present invention also provides toxic agents which are lethal or toxic to a selected pathogen. In one embodiment of the invention, the toxic agents of the invention comprise toxic proteins which cause lethality to a pathogen or selected cell (e.g., a diseased cell) or which render the pathogen or selected cell less fit. In one embodiment, such toxic proteins of the invention are lethal when overexpressed in a pathogen or selected cell. In other embodiments, a toxic protein is an exogenous protein that is toxic when expressed in a pathogen or selected cell. A toxic protein of the invention may further be engineered to have increased toxicity. For example, many methods are known in the art for introducing mutations, deletion, insertions etc. into a known sequence. Thus, optimization of a toxic protein is provided. The invention also provides methods for inhibiting the toxicity of a toxic protein, so that the toxic protein may be produced or manufactured in a producing cell. Inhibiting the toxicity may be performed by any methods known in the art, for example, the toxic protein may be expressed from an inducible promoter which allows expression to be turned on/off under appropriate conditions. A toxic protein may be expressed in a cell without causing lethality in the cell by overexpressing an antidote protein in the same cell. Other methods will be apparent to one skilled in the art and are within the scope of the invention.

The present invention provides toxic agents and methods for specifically targeting toxic agents to bacteria or bacteria-infected cells or other pathogens. Toxic agents of the present invention are directed to one or more targets and thus can be used alone or in combination to eradicate bacteria. Specifically, the invention provides the delivery of one or more toxic proteins, antisense RNAs, multi-ribozymes, or nucleic acids encoding the same, or a combination thereof, to a cell, tissue, or subject containing an infectious bacteria or pathogen in order to eradicate such bacteria or pathogen.

The present invention further encompasses the use of the toxic agents and/or ribozymes of the present invention as therapeutics and pharmaceutical compositions. In specific embodiments of the invention, the toxic agents of the invention are useful to treat microbial infections associated with severe burns, cystic fibrosis, cancer, or other immunocompromising conditions.

The present invention further encompasses the use of the toxic agents and/or ribozymes of the present invention for research and screening purposes. In one embodiment of the present invention, the ribozymes and/or toxic agents may be used to screen for viral, microbial, prokaryotic, or eukaryotic gene products or molecules to be targeted in order to effectively inhibit the selected virus or microbial agent or selected cell.

5.1. Pathogen-Specific and Tissue-Specific Toxic Agents

The invention provides specific nucleic acids which act as or encode toxic agents and are therefore useful as antimicrobial agents. A variety of toxic agents are within the scope of the invention. For clarity, the toxic agents of the invention are described herein below in several sub-types. The toxic agents of the invention include but are not limited to antisense nucleic acids, toxic gene products, sense nucleic acids,

5.1.1. Toxic Gene Products

The present invention relates to the use of toxic gene products or toxic proteins as toxic agents for the treatment of disorders and disease related to bacterial, parasitic, fungal, or viral infections or to cellular proliferation, and cancers, or to diseased cells. A toxic gene product of the invention is any gene product (such as DNA, RNA or protein), which is toxic to a pathogen or selected cell (such as a diseased cell). Such toxic gene products may be naturally occurring (endogenous), or may be non-naturally occurring (exogenous) in the target pathogen or selected cell. A toxic agent of the invention may be a chromosomally encoded, plasmid encoded, pathogen encoded, synthetic, or encoded in any other nucleic acid or nucleotide sequence. The present invention provides toxic agents which are endogenous toxic gene products that are expressed in a pathogen or selected cell which kill or render the pathogen or selected cell less fit. The present invention also provides toxic agents which are exogenous toxic gene products that are introduced into or expressed in a pathogen or selected cell which kill or render the pathogen or selected cell less fit. A pathogen or selected cell which is less fit is one which is weakened, or which is more susceptible to chemical treatment (such as drugs, toxins, pharmaceuticals, mutagens, solvents, etc.), or which is more susceptible to physical stress (such as temperature), or which is more susceptible to genetic alterations (such as by radiation or UV), or is more susceptible to environmental changes (such as available nutrients).

In several embodiments, the present invention provides the use of a plasmid addiction system protein as a toxic agent when expressed in bacteria or a selected cell. For example, in certain types of bacteriophage, the lysogenic (dormant) pathway is manifested by a bacterial cell maintaining only a single copy of the bacteriophage DNA in the form of a plasmid. In order to assure that both daughter bacterial cells receive a copy of the plasmid, a "plasmid addiction system" or "post-segregation system" is used by the cells which ensures that only bacterial cells which receive a copy of the plasmid will survive.

In one embodiment of the invention, a post-segregation system or plasmid addiction system toxin, is used as a toxic agent to a pathogen (such as bacteria) by overexpression of the toxin. Such overexpression of the toxin uncouples the toxin and the antidote, leading to toxicity, and preferably lethality, in the cell containing the overexpressed toxic agent.

For example, in one embodiment, the invention provides toxic agents which specifically target gene products essential for the survival or life cycle of a pathogen (such as replication, packaging etc). In one embodiment, the present invention provides naturally occurring addiction system toxins which have been modified to be expressed in the absence of the addiction system antidote. In another embodiment, the present invention provides naturally occurring addiction system toxins which have been modified to be expressed at higher levels than the addiction system antidote. In one example, an addiction system toxin (e.g., doc, chpBK, kicB, or gef) is used as a toxic agent and is uncoupled from its antidote. In another embodiment of the invention, a chromosomally encoded toxic gene product (such as chpBK, kicB, or gef) is used as a toxic agent to a pathogen by overexpression of the toxic gene product.

In certain embodiments, toxic agents include but are not limited to Shiga-like toxins of *E. coli*, cholera toxin of *Vibrio cholerae*, and cytotoxins of *P. aeruginosa*. For example, phage K139 confers to *V. cholera* a gene product that enhances enzymatic activity of cholera toxin. Such toxins are within the scope of the invention and may be used as a toxic agent in association with the methods and compositions of the invention. In certain embodiments of the invention, the bacteriocidal toxic agent is derived from a bacterium including but not limited to *Staphylococcus aureus, Enterococcus faecalis*, or *Pseudomonas aeruginosa*.

In another embodiment, the antidote of a toxin is the target of a trans-acting ribozyme or toxic agent of the invention. Thus, when the antidote is inactivated by the trans-acting ribozyme or toxic agent, the toxin is no longer neutralized or inactivated by the antidote, thus leading to toxicity, and preferably lethality to the pathogen.

In yet another embodiment, when the antidote is itself an antisense RNA, a sense RNA may be synthesized as a toxic agent and delivered to inactivate the antisense antidote. Thus, when the antidote is inactivated by the sense RNA, the antidote is no longer available to inactivate the toxin, thus leading to toxicity, and preferably lethality.

One example of an addiction system toxin that may be used in connection with the invention is doc (death on curing; Lehnherr H, et al., 1993, J. Mol. Biol. 233:414-28). The protein encoded by doc is lethal or toxic in both Gram-negative and Gram-positive organisms (e.g., *E. coli, P. aeruginosa, Staphylococcus aureus*, and *Enterococcus faecalis*). doc acts as a bacterial cell toxin to which Phd (prevention of host death) is the antidote. Accordingly, the invention provides for plasmids expressing doc which can be delivered to a bacterial pathogen in order to render the pathogen less fit, and preferably eradicate the pathogen. A particular advantage of doc is that doc has little to no toxicity to eukaryotic cells, and thus may be administered safely to a eukaryotic host.

Specific examples of addiction system toxins or chromosomally encoded toxins, or other toxic agents which may be used in connection with the invention include but are not limited to ccdB, kid, perK, parE, doc, higB, chpAK, chpBK, kicB, hoc, srnB', flmA, pmdA, relF, gef, kilA, kilB, kilC, kilE, traL, traE, sigB, hok, pemK, lysostaphin, and kikA. Examples of antidotes which may be used as in the methods of the invention include but are not limited to ccdA, kis, pemI, parD, phd, higA, chpAI, chpBI, kicA, soc, srnC, flmB, pndB, sof, korA, korB, korC, korD, korE, and korF. Thus, the invention herein provides a method of using a an addiction system toxin (such as doc) or other toxic protein, as a toxic agent of the invention. The invention also provides methods for inhibiting or inactivating antidotes of a toxin. The invention further provide co-expression of a toxin and its corresponding antidote for manufacturing purposes.

In certain specific embodiments, the invention provides toxic agents chpBK, kicB, and gef. Each of the proteins of kicB, or gef are lethal in *E. coli* but not in *P. aeruginosa*. Accordingly, the invention provides for the use of kicB or gef in the eradication or treatment of bacterial infections of *E. coli*. In one embodiment, kicB or gef encoding nucleic acids are delivered by a to the *E. coli* by a P1 bacteriophage of the invention containing a transfer plasmid, said transfer plasmid encoding the kicB or gef toxic agents (or both).

In another specific embodiment of the invention, the chpBK protein is a toxic agent of the invention and is lethal to *E. coli* and toxic or lethal in *P. aeruginosa*. Accordingly, the invention provides for the use of chpBK in the eradication or treatment of infections of *E. coli* or *P. aeruginosa*. In one embodiment, chpBK nucleic acids are delivered by a to *E. coli* or *P. aeruginosa* by a P1 bacteriophage of the invention, containing a transfer plasmid, said transfer plasmid encoding the chpBK toxic agent. The antidote protein that antagonizes chpBK function is called ChpB1. Accordingly, the invention provides, for the co-expression of the antidote ChpB1 and chpBK for manufacturing purposes.

In several embodiments of the invention, the toxic gene, such as doc, chpBK, kicB, or gef, is placed under the control of an inducible promoter and is uncoupled from the antidote. In one embodiment, the promoter is the P1 lytic promoter P53. In a preferred embodiment, the promoter is the LEASHI promoter. In a preferred embodiment, for the treatment of *P. aeruginosa* infections, the invention provides *P. aeruginosa* specific promoters, anr, arc or proC.

In other specific embodiments of the invention, a consensus ribosome binding site (GGAGGTGXXXXATG (SEQ ID NO:12), wherein X is any nucleotide) may be inserted immediately upstream of the nucleic acids encoding the toxic agent and leads to increased expression of the toxic agent. The provides for the use of a combination of a promoter and a ribosome entry site(s) to modulate expression of a toxic agent or ribozyme.

It is also within the scope of the invention that more that one toxic agent may be used to eradicate or treat an infection. For example, it is contemplated that two or more toxic agents may be engineered into a single transfer plasmid for delivery by a bacteriophage. Such bacteriophage could serve to deliver nucleic acids encoding multiple toxic agents to target bacteria. Alternatively, two or more transfer plasmids may be carried by a single bacteriophage, wherein each transfer plasmid encodes different toxic agents. In this embodiment, when more than one Tranfer plasmids are used, such plasmids are designed such that the two or more plamids are non-recombinigenic. Such methods of engineering non-recombinigenic sequences are known in the art. Additionally, in this embodiment, the two or more engineered plasmids will preferably have different origins of replication. In this manner, the bacteriophage serves to deliver nucleic acids encoding multiple toxic agents. In yet a third alternative, bacteriophage may be designed to carry multiple toxic agents on multiple transfer plasmids. When two or more toxic agents are encoded within a single bacteriophage, the nucleic acids encoding such toxic agents may be operably linked to the same promoter, or different promoters (e.g., see sections 5.4 and 5.4.1 herein).

5.1.2. Antisense

The invention provides specific nucleic acids which act as toxic agents and are therefore useful as antimicrobial agents. The invention provides antisense RNA molecules which target an RNA of a pathogen or selected cell. Target RNAs of the invention may be pathogen-specific RNAs, tissue-specific cellular RNAs, or disease-specific RNAs. The invention also provides modified and enhanced antisense nucleic acids which target pathogen-specific RNAs, tissue-specific cellular RNAs, or disease-specific RNAs.

The proposed target of the toxic antisense molecule of the invention is the RNA of a gene which plays a critical role in the survival of the pathogen, or which is essential to the pathogen's life cycle. The present invention also encompasses modifications to naturally occurring antisense molecules which modulate the expression of an essential gene product of a pathogen. For example, as described below, one proposed target of an antisense of the invention is the ftsZ gene whose gene product plays a critical role in the initiation of cell division of *E. coli*.

In another embodiment, the toxic agents of the invention comprise antisense molecules designed to have enhanced inhibition of target RNAs. The toxic agents which comprise antisense molecules of the invention are engineered to more specifically bind target RNAs in that the sequences of such toxic antisense molecules are designed to have increased complementarity to a target sequence such as an essential RNA of a pathogen or selected cell. Such toxic antisense molecules are therefore more specific to their targets and hence, have increased efficacy. The invention provides antisense toxic agents and ribozymes which are also modified with a hairpin structure to create a more stable molecule. The antisense toxic agents of the invention may also be expressed to a high level in a target pathogen or cell by any method known or cell by any method known in the art. For example, an antisense toxic agent may be expressed in trans from a multi-copy expression plasmid using a strong regulatable promoter. The antisense toxic agent may also be operably linked to a tissue-specific or pathogen-specific promoter such that the antisense molecule is only expressed in a pathogen or cell which uses the same promoter.

Specifically, the invention provides antisense RNAs which target essential nucleotide sequences, such as DicF1 or a DicF1-like antisense molecule that specifically target a nucleotide sequence which encodes a protein essential for replication or survival. Further, the invention provides modified antisense structures with increased stability to act as lethal agents when expressed in bacteria. The invention also provides toxic sense molecules designed to target essential antisense molecules.

In another embodiment of the invention the toxic agents comprise sense RNA molecules targeted to antisense RNAs which are required for the survival of the pathogen or cell. For example, an antidote of a toxic protein (such as an addiction system toxin) may be in the form of an antisense molecule which regulates the expression of the toxin. Such an antisense antidote allows the pathogen or cell to survive in the presence of such toxin. The invention provides inhibition of the antisense antidote by a toxic agent in the form of a sense RNA molecule.

In certain embodiments a combination of two or more toxic molecules may be delivered to a pathogen (such as *E. coli, P. aeruginosa*, etc.) in order to cause lethality. In this embodiment, the toxic antisense may be directed to the same target, or different targets. When different targets of a pathogen or cell are targeted, such targets may be involved in the same biological pathway within the pathogen or different biological pathways.

In a specific embodiment, the antisense sequence is based on DicF (Bouche F, et al., 1989, Mol Microbiol. 3:991-4). Such modified DicF sequence is referred to as DicF1 (SEQ ID NO:9). Naturally occurring DicF is part of an intercistronic region that when expressed in *Escherichia coli* causes inhibition of cell division. This inhibition does not require the translation of DicF mRNA into protein, instead, DicF RNA exerts its inhibitory effect as an antisense molecule.

The proposed target of DicF is the ftsZ gene whose gene product plays a critical role in the initiation of cell division of *E. coli*. Temperature sensitive mutations of the ftsZ gene indicate that it is essential for viability of *E. coli*. Without limitation as to mechanism, DicF RNA is believed to bind specifically to the 5' untranslated region of ftsZ mRNA, thereby inhibiting ftsZ protein expression. Cells lacking the ftsZ protein are unable to divide and ultimately die. DicF homologs have been identified in a variety of other bacteria although it is not known whether they exert a similar function.

The present invention provides for modified DicF nucleic acids, called DicF1 or DicF1-like RNAs, which are used as antimicrobial agents, or toxic agents of the invention. DicF1 RNA is a superior antisense molecule as compared to the endogenous DicF RNA. It has been modified by increasing its complementarity to the ftsZ 5' untranslated mRNA. It is therefore more specific to its target and hence, has increased efficacy. An auto hairpin structure has further been enhanced to create a more stable molecule. The invention also provides modifications of other naturally occurring antisense molecules, such as nucleotide sequences which have similar functions as DicF in modulating the expression of gene products essential to the pathogen's life cycle or survival. Such nucleic acid is referred to as a DicF1-like nucleic acid. In contrast to the endogenous DicF, the DicF1 or a DicF1-like nucleic acid of the invention may be expressed in trans from a multi-copy expression plasmid. Further, the DicF1 or DicF1-like nucleic acids may be operably linked to a variety of promoters that may be used to control the strength, timing, or distribution of such expression. DicF1 or a DicF1-like nucleic acid may also be expressed in trans from a ribozyme cassette. The combination of these features results in DicF1 or DicF1-like nucleic acid being an effective antimicrobial agent against a pathogen (such as *E. coli*). In other embodiments, modifications to the sequence of an antisense of the invention allows targeting against a variety of other bacteria. In other embodiments, modifications to the sequence of an antisense of the invention allows targeting in a pathogen-specific manner. The invention also provides DicF1-like nucleic acids which may be used as toxic agents in bacteria, bacteria-infected cells, or other pathogens which have complementary RNA targets.

5.1.3. Ribozymes

The present invention provides methods by which a trans-acting ribozyme may be used in addition to the toxic agents of the invention. Further, a multi-ribozyme may be used as an expression system for one or more toxic agents or trans-acting ribozymes. These ribozymes of the invention can be used, for example, to destroy tissue-specific disease, or to treat bacterial, viral, or parasitic infections. The ribozymes of the present invention may comprise one or more multi-ribozymes.

In accordance with the present invention, the multi-ribozyme may comprise one or more ribozymes or one or more ribozyme cassettes. Each cassette in turn may consist of a catalytic core (e.g., containing one or more trans-acting ribozymes or containing one or more toxic agents) and one or more flanking regions. The catalytic core can target a pathogen, by specifically inhibiting a pathogen-specific target. The catalytic core can target a cell (such as a diseased cell), by specifically inhibiting a tissue-specific target (such as disease-specific target). Further, as described in sections below, the multi-ribozymes of the invention also provide a means of delivering toxic agents to a cell, and expressing toxic agents of the invention (including antisense RNA, toxic gene products) in a cell or tissue-specific, or pathogen-specific manner. In one embodiment, the ribozyme cassette may consist of a 5' autocatalytically cleaving ribozyme sequence, a core catalytic ribozyme comprising a trans-acting ribozyme and a 3' autocatalytically cleaving ribozyme. In another embodiment, the multi-ribozymes comprise a cassette including, the enhanced 5' and 3' autocatalytically cleaving ribozyme sequence. In another embodiment, the multi-ribozymes contain one or more internal trans-acting ribozymes. Such trans-acting ribozymes may be directed to the same site on the same RNA, different sites on the same RNA, or different RNAs. Thus, trans-acting ribozymes of the invention may target a pathogen-specific RNA or tissue-specific RNA.

The present invention also provides multi-ribozymes and their use to target RNA in a tissue-specific or pathogen-specific manner for the treatment of disease such as bacterial infection. The invention provides multi-ribozymes containing one or more internal trans-acting ribozyme. Trans-acting ribozymes act in a target-specific manner and therefore may, in certain embodiments, act on a pathogen (such as bacteria) or a selected cell (such as a diseased cell) to enhance the use of toxic agent. In accordance with the present invention, the multi-ribozymes may comprise a) a trans-acting ribozyme or toxic agent flanked by 5' and 3' autocatalytically cleaving ribozymes or enhanced autocatalytically cleaving ribozymes; b) a trans-acting ribozyme or toxic agent flanked by either a 5' or 3' autocatalytically cleaving ribozyme; or c) multi-trans-acting ribozymes and/or multiple toxic agents, flanked by one or both 5' and 3' autocatalytically cleaving ribozymes or enhanced autocatalytically cleaving ribozymes. For example, in a specific embodiment, the invention provides a multi-ribozyme with two trans-acting ribozymes, wherein the first trans-acting ribozyme cleaves an HBV target, and the second trans-acting ribozyme cleaves a HCV target. In this embodiment, it may also be desirable to target the expression of such multi-ribozyme to the liver, e.g., by operative association with a liver-specific promoter. Thus, the multi-ribozymes of the invention may be used to deliver one or more toxic agents to a bacteria or bacteria-infected cell or tissue. In accordance with the present invention the multi-transacting ribozymes may be targeted to the same site on the same RNA, different sites on the same RNA or different RNAs. In accordance with the present invention the multiple toxic agents may be targeted to the same site on the same target (such as a cellular RNA or protein), different sites on the same target or different targets.

The ribozymes of the present invention possesses sufficient catalytic activity to inactivate the RNA of the targeted RNAs. From an antimicrobial perspective, hammerhead-type ribozymes are especially attractive since the molecule inactivates gene expression catalytically through the cleavage of the phosphodiester bond of the mRNA. Furthermore, hammerhead-type ribozymes have been re-engineered to function in an intermolecular or transducer (trans) acting state (Haseloff et al., 1988, Nature 334(6183):585-91; Uhlenbeck. O. C., 1987, Nature 328(6131):59). The catalytic activity of the ribozyme requires a sufficient concentration of the divalent cation, $Mg^{+2}$, and substrate. The substrate can have any sequence as long as the cleavages site contains the recognition element NUX, where N represents any nucleotide, U corresponds to uracil, and X is any nucleotide except G (Koizumi et al., 1989, Nucleic Acids Resonant. 17(17):7059-71). Ribozymes have been widely demonstrated to function in vivo (Christoffersen et al., 1995, J. Med. Chem. 38(12):2023-37; Inokuchi et al., 1994, J. Biol. Chem. 269(15):11361-6). The present invention improves the initial design of hammerhead-type ribozymes (Taira et al., 1991, NAR 19(9):5125-5130) by constructing multi-ribozymes consisting of ribozyme cassettes. Ribozyme cassettes contain one or more cis-acting hammerhead ribozymes flanking a ribozyme that inactivates the targeted RNA(s) as well as one or more flanking sequences. Upon transcription the targeted ribozyme is released as a 60-70 base transcript which not only improves its specificity by reducing non-specific interactions but also improves its catalytic activity as well. This invention includes modifications to and use of the ribozyme described in U.S. Pat. No. 5,824,519 and PCT publications No. WO98/24925, WO97/17433, WO98/24925, WO99/67400, which are incorporated by reference herein in their entirety.

5.2. Nucleic Acids Encoding Toxic Agents or Ribozymes

The invention also provides nucleic acids and expression cassettes which encode the ribozymes and/or toxic agents of the invention. These nucleic acids can be used to express the ribozymes or toxic agents of the invention at the selected site. The site can be tissue-specific in the case of treating tissue-specific cancers or disease, or it can be pathogen-specific in the case of ribozymes or toxic agents that prevent replication of infectious agents to treat infection (e.g., hepatitis, herpes, malaria, tuberculosis, bacterial infections etc.). The invention provides nucleic acids which encode toxic agent(s) and/or ribozyme(s) which are target-specific. The invention also provides nucleic acids which encode toxic agent(s) and/or ribozyme(s) operably linked to a tissue-specific or pathogen-specific promoter.

There are several options for constructing the multi-ribozyme encoding sequences: 1) ribozymes directed to different targets in the same pathogen 2) multiple copies of the same ribozyme 3) multiple ribozymes directed to multiple targets, and 4) multiple ribozymes directed to different sites on the same target. There are also several options for constructing the toxic agent encoding sequences: 1) toxic agents directed to different targets in the same pathogen 2) multiple copies of the same toxic agent 3) multiple toxic agents directed to multiple targets, and multiple toxic agents directed to the same target. Further, toxic agents and ribozymes may be combined in various ways, e.g., a multi-ribozyme and a nucleic acid encoding a toxic agent may be engineered in a single construct under one promoter. The promoter can have the chosen level of specificity as described herein.

The nucleic acids of the invention encode one or more toxic agents of the invention. Thus, nucleic acids encoding toxic proteins of the invention include but are not limited to addiction system toxins. The invention further provides modified and enhanced addiction system toxins which have been engineered to be more toxic or more specific to a particular target pathogen. The present invention provides nucleic acids encoding antisense molecules targeted to RNA of a gene which plays a critical role in the survival of the pathogen, or which is essential to the pathogen's life cycle. The present invention also encompasses nucleic acids comprising modifications to naturally occurring antisense molecules which modulate the expression of an essential gene product of a pathogen.

The nucleic acids of the invention also relate to those encoding antisense molecules of the invention. The invention provides modified and enhanced antisense molecules which have enhanced stability, enhanced complementarity to a target RNA, or enhanced specificity for a target RNA or target pathogen. The invention also provides nucleic acids encoding modified naturally occurring antisense molecules, such as nucleotide sequences which have similar functions as DicF in modulating the expression of gene products essential to the pathogen's life cycle or survival.

The nucleic acids of the invention also relate to nucleic acids encoding sense RNA molecules capable of targeting an essential antisense molecule.

The nucleic acid, encoding a toxic agent selected from the group consisting of ccdB, kid, perK, parE, doc, higB, chpAK, chpBK, kicB, hoc, srnB', flmA, pmdA, relF, gef kilA, kilB, kilC, kilE, traL, traE, sigB, hok, pemK, lysostaphin, and kikA is provided. The nucleic acid encoding the toxic agent DicF1, or DicF1-like, is provided.

In several embodiments, nucleic acids of the invention encode a catalytic multi-ribozyme(s) that contains two separable functional regions including a) a catalytic sequence (also known as the "catalytic core") which cleaves the target RNA, and b) flanking regions which include cis-acting autocatalytically cleaving ribozyme(s). As described above, the catalytic core consists of one or more trans-acting ribozyme(s) and/or one or more toxic agent(s). The present invention provides nucleic acid which encode an internal targeted ribozyme containing two or more trans-acting ribozymes, wherein each of the separate trans-acting ribozymes can be targeted to the same or different target RNA molecules. By nucleic acid complementarity, the binding site directs the ribozyme core to cleave a specific site on the target RNA molecule. The length of flanking sequences have implications not only for specificity, but also for the cleavage efficiency of the individual ribozyme molecules. In the present catalytic ribozyme, the flanking sequences are highly specific for the target RNA, yet allow ready dissociation from the target RNA once cleavage occurs. This permits cycling of the ribozyme and reduces the amount of ribozyme required be effective. A range of binding/dissociation values from 16-21 Kcal is expected to be effective. The present invention provides nucleic acid which encode a two or more toxic agents, wherein each of the toxic agents can be targeted to the same or different target molecules.

The invention additionally provides nucleic acids and expression cassettes which encode the toxic agent and/or ribozymes of the invention. These nucleic acids can be used to express the toxic agent and/or ribozyme of the invention at the selected site. In one embodiment, the nucleic acid comprise a tissue-specific promoter operably linked to a toxic agent. In another embodiment, the nucleic acids and expression cassettes of the invention comprise a tissue-specific promoter operably linked to a sequence encoding a catalytic ribozyme comprising one or more target RNA-specific trans-acting ribozymes and one or more toxic agents. In another embodiment, the nucleic acids comprise a pathogen-specific promoter from a sequence encoding a toxic agent. In another embodiment, the nucleic acids and expression cassettes of the invention comprise a pathogen-specific promoter operably linked to a sequence encoding a 5' autocatalytically cleaving ribozyme sequence, a catalytic ribozyme comprising one or more target RNA-specific trans-acting ribozymes and/or pathogen-specific toxic agents, and a 3' autocatalytically cleaving ribozyme sequence. In accordance with the present invention, the expression cassettes may be engineered to express two or more multi-ribozymes containing trans-acting ribozymes which act on the same or different targets. The expression cassettes may also be engineered to express two or more multi-ribozymes containing 5' and 3' autocatalytically cleaving ribozymes with either slow or enhanced cleavage activity.

The expression cassettes of the invention or the nucleic acids encoding the toxic agents of the invention may be placed into any suitable plasmid known in the art (such as a bacteriophage transfer plasmid, bacterial plasmid, or eukaryotic expression plasmid). The invention also provides novel and modified plasmids for use in accordance with the invention.

At the molecular genetic level the coding sequence for a toxic agent, ribozyme, or multi-ribozyme of the invention may be placed under the control of one or more of the following genetic elements: a naturally occurring strong, intermediate, or weak constitutively expressed or regulated promoter from the targeted microorganism, or an artificially contrived constitutively expressed or regulated promoter containing either a strong, intermediate or weak consensus sequence that accords the desired levels of ribozyme and/or toxic agent expression. The present invention provides promoter elements which are pathogen-specific. The invention provides promoter elements which are used to achieve pathogen-specific expression of the toxic agents of the present invention. The present invention provides promoter elements which are tissue-specific. The invention provides promoter elements which are used to achieve tissue-specific expression of the toxic agents of the present invention. Accordingly, the present invention provides nucleic acids encoding promoter elements which are pathogen-specific. The invention provides promoter elements which are used to achieve pathogen-specific expression of the toxic agent(s) and/or ribozyme(s)

of the present invention. The present invention provides promoter elements which are tissue-specific. The invention provides promoter elements which are used to achieve tissue-specific expression of the toxic agent(s) and/or ribozyme(s) of the present invention.

In one embodiment, the nucleic acid comprise a tissue-specific promoter operably linked to a sequence encoding one or more toxic agent(s). In another embodiment, the nucleic acids comprise a tissue-specific or pathogen-specific promoter operably linked to a sequence encoding at least one autocatalytic ribozyme and one or more trans-acting ribozymes. In another embodiment, the nucleic acids comprise a tissue-specific or pathogen-specific promoter operably linked to a sequence encoding at least one or more toxic agents. In another embodiment, the nucleic acids comprise a pathogen-specific promoter operably linked to a sequence encoding at least one autocatalytic ribozyme and one or more trans-acting ribozymes and one or more toxic agents. In accordance with the present invention, the trans-acting ribozymes and/or toxic agents of the invention may act on the same or different targets.

In yet another embodiment, the present invention provides a novel vector or plasmids encoding the toxic agent(s) and/or ribozyme(s) of the invention. The novel vectors of the present invention may be used to engineer a wide variety of toxic agents and/or ribozymes including, but not limited to, tissue-specific, pathogen-specific, promoter-specific, antimicrobial specific, antiviral specific, anticancer specific, antitumor specific, or target-specific. The invention also relates to a vector or plasmid origin of replication which modulates specificity of the replication of a vector or plasmid in a cell or pathogen. The invention also relates to the copy number of a vector or plasmid in a selected cell or pathogen to modulate the dose of the toxic agent and/or ribozyme.

In a specific embodiment, the invention provides novel plasmids which encode a toxic protein. In another specific embodiment, the invention provides novel plasmids which encode a mutant bacteriophage pac site or a mutant bacteriophage pacABC sequence.

5.2.1. Eucaryotic and Procaryotic Expression Vectors

The present invention encompasses expression systems, both eucaryotic and procaryotic expression vectors, which may be used to express the toxic agents and/or multi-ribozymes of the invention. The DNA expression vectors and viral vectors containing the nucleic acids encoding the toxic agents of the present invention may be produced by recombinant DNA technology using techniques well known in the art. Thus, methods for preparing the expression vectors and viral vectors of the invention by expressing nucleic acid encoding a toxic agent and/or multi-ribozyme sequences are described herein. Methods which are well known to those skilled in the art can be used to construct expression vectors containing gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, nucleic acids capable of encoding a toxic agent and/or ribozyme sequence may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the selected toxic agent and/or multi-ribozyme of the invention. Such host-expression systems represent vehicles by which the sequences encoding the toxic agents or ribozymes of the invention may be introduced into cells, tissues, or pathogens both in vivo and in vitro but also represent cells which may, when transformed or transfected with the appropriate nucleotide coding sequences, to express a toxic agent and/or ribozymes of the invention. These include but are not limited to microorganisms such as bacteria transformed with recombinant bacteriophage DNA, plasmid DNA or cosmid DNA expression vectors containing selected toxic agent(s) and/or multi-ribozyme coding sequences; yeast (e.g., Saccharomyces, Pichia) transformed with recombinant yeast expression vectors containing the selected toxic agent(s) and/or multi-ribozyme coding sequences; insect cell systems infected with recombinant virus expression vectors (e.g., baculovirus) containing the selected toxic agent(s) and/or multi-ribozyme coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing selected toxic agent(s) and/or multi-ribozyme coding sequences; or mammalian cell systems (e.g., COS, CHO, BHK, 293, 3T3) harboring recombinant expression constructs containing promoters derived from the genome of mammalian cells e.g., metallothionein promoter) or from mammalian viruses (e.g., the adenovirus late promoter; the vaccinia virus 7.5K promoter).

5.3. Delivery and Expression of Toxic Agents

The invention also provides a novel vehicle for the delivery of toxic agents or ribozymes of the invention. The invention encompasses DNA expression vectors and viral vectors that contain any of the foregoing coding sequences operatively associated with a regulatory element that directs expression of the coding sequences and genetically engineered host cells that contain any of the foregoing coding sequences operatively associated with a regulatory element that directs the expression of the coding sequences or RNAs in the host cell or pathogen. A key to the present invention is the strategy used to deliver the toxic agent and/or ribozyme to the targeted microorganism or pathogen. Two separate classes of delivery systems can be manufactured, one biologic in nature and the other abiologic.

Accordingly, present invention also provides the delivery of the toxic agents of the invention to cell or pathogen by abiologic or biologic systems. The present invention provides compositions of matter which has resulted from the development of methods and compositions for the delivery of one or more ribozymes and/or toxic agents directed against fundamental and essential cellular processes specific to a targeted microorganism through an inactivated, altered, or modified virus (virion) or bacteriophage delivery vehicles. The present invention also provides abiologic delivery vehicles, capable of delivering a nucleic acid comprising the toxic agent(s) and/or ribozyme(s) into the targeted microorganism.

5.3.1. Biologic Delivery Vehicles

The biologic delivery vehicle of the invention takes advantage of the fact that generalized transducing particles lack DNA originating from the viral delivery vehicle or have a reduced capacity to transfer DNA originating from the viral delivery vehicle. In a preferred embodiment of the invention, the viral delivery vehicle is a bacteriophage, or modified bacteriophage. In one embodiment, such viral or bacteriophage particles only contain sequences of host origin. In other embodiments, such particles contain engineered plasmids/vectors encoding the toxic agent(s) or ribozyme(s) to be delivered. In other embodiments, such particles contain engineered plasmids/vectors encoding the toxic agent(s) or ribozyme(s) to be delivered and contain mutations which inactivate the ability of the delivery vehicle to transfer DNA originating from the delivery vehicle. Consequently, the invention uses a biologic assembly of viral head proteins (packaging elements for the antimicrobial therapeutic) around the nucleic acid containing the necessary genetic elements that will insure the desired level of expression of the toxic agent(s) and/or ribozyme(s). An important features of the present invention are the combination of toxic agents or ribozyme with viral delivery and assembly of the virions using a unique combination of plasmid features.

In one preferred embodiment, the invention provides bacteriophage which deliver a toxic agent of the invention. Bacteriophage of the invention may be constructed to deliver one or more toxic agents of the invention, such as one or more toxic gene products, proteins, antisense RNAs, sense RNAs, or combination thereof. In another embodiment of the invention, a host cell is constructed to express a pathogen-specific toxic agent or ribozyme. In yet another embodiment of the invention, a host cell is constructed to express a repressor of a promoter used in the invention.

In other embodiments, a host cell may be engineered to overexpress an antidote to a toxic agent such that the host cell is protected from toxicity and may be used as a producing strain, or manufacturing strain.

The present invention also encompasses expression systems, which may be used to express the toxic agents and/or ribozymes such as bacteriophage, viral vectors, etc. For example, a variety of bacteriophage systems may be utilized to express the selected ribozyme(s) and/or toxic agent(s) of the invention. For example, such bacteriophage systems represent vehicles by which the sequences encoding the toxic agent(s) and/or ribozyme(s) may be introduced into target bacteria both in vivo and in vitro. In several embodiments, the specific bacteriophage which is selected determines the species of bacteria which is targeted and infected by that bacteriophage.

In one embodiment, delivery of a toxic agent to a pathogen is by use of a bacteriophage or other delivery vehicle which targets the pathogen of interest. In one embodiment, the bacteriophage (or delivery vehicle) delivers the toxic agent or nucleic acids encoding the toxic agent to the pathogen. In a specific embodiment, a toxic agent of the invention is delivered to a bacterial cell by a modified bacteriophage capable of infecting a pathogenic bacteria. In a further embodiment, bacteriophage are selected for their ability to infect a particular species or genera of bacteria, and are used to deliver a toxic agent for the eradication of such bacterial species or genera from a host. In a preferred embodiment, the delivery vehicle or nucleic acids native to the delivery vehicle are modified such that they contain insufficient genetic information for the delivery of nucleic acids native to the delivery vehicle. Thus, the modified delivery vehicle (e.g., virion or bacteriophage) can serve as a molecular vehicle that delivers the ribozyme(s) and/or toxic agent(s) of the invention to the target cell or pathogen, but does not deliver replicable nucleic acids native to the delivery vehicle. Alternatively, an abiologic delivery system (e.g., liposomes) can be used to package nucleic acid carrying the genetic elements necessary and sufficient for the proper expression of the ribozyme(s) and/or toxic agent(s).

The toxic agents and/or ribozymes of the invention may be used to treat infection from a variety of pathogens. These include but are not limited to microorganisms such as bacteria, parasites, and fungi. In specific embodiments of the invention, the toxic agents of the invention, delivered by a viral delivery vehicle (such as a modified bacteriophage are useful to treat microbial infections associated with severe burns, cystic fibrosis, cancer, or other immunocompromising conditions.

5.3.1.1. Delivery & Expression by Viral Vectors

In accordance with the present invention, a wide variety of viruses and viral vectors may be used to deliver the nucleotide sequences encoding the toxic agent(s) and/or ribozymes of the present invention, a few examples of which are described below. In this regard, a variety of viruses may be genetically engineered to express the selected toxic agent(s) and/or ribozymes in order to target a specific pathogen.

The present invention also relates to the delivery of the toxic agents of the invention to cell or pathogen by abiologic or biologic systems. In a specific embodiment, For example, as described herein, a toxic agent of the invention is delivered to a bacterial cell by a bacteriophage capable of infecting a pathogenic bacteria. In a further embodiment, bacteriophage are selected for their ability to infect a particular species of bacteria, and are used to deliver a toxic agent for the eradication of such bacterial species from a host.

The invention provides for use of a virion which can also be any bacteriophage which specifically infects a bacterial pathogen of the present invention as well as any virus which can be specifically targeted to infect the pathogen of the present invention. For example, the bacteriophage can include, but is not limited to, those specific for bacterial cells of the following genera: *Bacillus, Campylobacter, Corynebacterium, Enterobacter, Enterococcus, Escherichia, Klebsiella, Mycobacterium, Pseudomonas, Salmonella, Shigella, Staphylococcus, Streptococcus, Vibrio, Streptomyces, Yersinia* and the like (see, e.g., the American Type Culture Collection Catalogue of Bacteria and Bacteriophages, latest edition, Rockville, Md.), as well as any other bacteriophages now known or later identified to specifically infect a bacterial pathogen of this invention. The invention also provides for the use of a virion which specifically infects a fungal pathogen.

This delivery system consists of a DNA plasmid carrying the nucleic acids coding for the toxic agent(s) and/or ribozyme(s) packaged into viral particles. Specificity is conferred by the promoter driving transcription of the toxic agents and/or ribozymes and by the host specificity of the viral vehicle. Specificity is also conferred by the origin of replication controlling vector replication.

In the virions of the present invention, the non-viral DNA can encode one or more toxic agent(s) and/or one or more ribozyme(s). In the virions, the non-viral DNA can comprises a pathogen-specific or tissue-specific promoter operably linked to a sequence encoding one or more toxic agents or ribozymes.

The nucleic acid delivered by a virion can encode one or more toxic agent(s) and/or one or more ribozyme(s) or a combination thereof. The virion can comprise any nucleic acid encoding a ribozyme or toxic agent, particularly those described herein.

Bacteriophage P1

The invention provides the use of any virion for the delivery of a toxic agent or ribozyme to a target cell. For example, a common bacteriophage of *E. coli*, P1, is an attractive delivery vehicle for the invention for a number of reasons. First and foremost, P1 has a broad intergenera and interspecies range (Yarmolinsky et al., 1988, Mol. Gen. Genet. 113:273-284). The P1 receptor of *E. coli* is the terminal glucose of the lipopolysaccharide (LPS) core lysergic ring of the bacterial outer membrane (Generalized Transduction, p. 2421-2441. In F. Neidhardt (ed.), *Escherichia coli* and *Salmonella*:Cellular and Molecular Biology, 2d ed. Vol. 2, ASM Press, Washington, D.C.). Yarmolinsky and Sternberg report that in addition to *E. coli*, this particular phage has the ability to inject its nucleic acid into a large number (>25) of diverse Gram negative bacteria (Yarmolinsky et al., 1988, Mol. Gen. Genet. 113:273-284). Secondly, P1 can accommodate a significant amount of genetic information, over 2% (100,000 bp) of the DNA of *E. coli* (Generalized Transduction, p. 2421-2441. In F. Neidhardt (ed.), *Escherichia coli* and *Salmonella*:Cellular and Molecular Biology, 2d ed. Vol. 2, ASM Press, Washington, D.C.). Consequently, gene dosage of the ribozymes or toxic agents can be increased through multiplication of the toxic agents and/or ribozymes, thereby increasing the microbicidal activity of the toxic agents and/or ribozymes. Accordingly, bacteriophage P1 is used as the delivery vehicle or molecular syringe. P1 has advantages over certain with lytic phage therapy which may harbor risk of 1) dissemination of undesirable products (e.g., DNA originating from the P1 bacteriophage) to nonpathogenic indigenous microflora, 2) excessively narrow host range, 3) rapid clearance of the material by the reticuloendothelial system of the host and 4) the concern that a lytic infection could become uncontrolled in commensal bacteria in immunocompromised patients. In certain of these embodiments, the P1 delivery system is the preferable delivery vehicle for delivery of a toxic agent to a target pathogenic bacterium. An additional advantage of the P1 delivery vehicle is that phage-mediated transfer of undesirable products may be decreased or avoided when the phage are engineered such that they are incapable of transferring endogenous phage DNA to the host. In this embodiment, the phage particles inject transfer plasmid DNA into target bacterial cells. Expression of the encoded toxic agents may then result in bacterial cell death independent of the bacterium's resistance to antibiotics.

Additionally, a process utilizing in vitro packaging is also possible. In vitro packaging can be accomplished through the addition of PAC-sites to the genetic information of the toxic agent or ribozyme construct. P1 packaging initiates within one of the P1 PAC genes (Steinberg, N., 1987, J. Mol. Biol. 194(3):469-79). It has been reported that the active PAC site is contained within a 161 base-pair segment of the P1 EcoR1 fragment 20 (Steinberg, N., 1987, J. Mol. Biol. 194(3):469-79). Thus, the phage head serves as a molecular syringe that delivers the inactivating ribozyme(s) and/or toxic agent(s) to the pathogen.

In specific preferred embodiments of the invention, a toxic agent is encoded in a Transfer plasmid, and is used in connection with a P1 bacteriophage delivery system. Such Transfer plasmid preferably contains 1) an origin or replication 2) selectable marker 3) Pac ABC genes with a P1 PAC site 4) P1 lytic replicon and 5) nucleic acids encoding one or more toxic agents of the invention (e.g., antisense molecule, ribozyme, or toxic protein, etc). The Transfer plasmid may be produced in a bacterium producing cell (e.g., a P1 lysogen). In preferred embodiments of the invention, the bacteriophage P1 plasmid (e.g., the P1 prophage) is engineered to be incapable of being packaged into a phage head. In this embodiment, only Transfer plasmids are packaged into virions. Such inhibition of P1 plasmid packaging is accomplished by introducing a mutation or deletion in the P1 plasmid that inhibits the P1 plasmid from being packaged into a virion or phage head. Mutation(s) or deletion(s) of the P1 plasmid which inhibit packaging include but are not limited to one or more mutations and/or deletions in the P1 plasmid PAC site. Any mutation(s) and/or deletion(s) of the P1 plasmid which inhibits packaging of the bacteriophage P1 plasmid is with in the scope of the invention. Such mutations or deletions are introduced by standard techniques known in the art. In several embodiments, the P1 lysogen has a temperature sensitive repressor mutation (e.g. C1.100). Preferably, induction of the P1 lysogen leads to the production of P1 phage heads containing only the packaged Transfer plasmid. Bacteriophage containing the packaged Transfer plasmid nucleic acids may then be used to infect a target cell such as a bacterial pathogen. The bacteriophage infects a bacterial pathogen by injecting its nucleic acids into the bacterium. The toxic agent encoded in the bacteriophage nucleic acids is thus delivered to the bacterium. Within the bacterium, the Transfer plasmid nucleic acids recircularize, and the toxic agent is expressed in the bacterium leading to toxicity and death. Similar mutation and/or deletion strategies may be used with the other viral delivery systems of the invention such that the deletion(s) and/or mutation(s) allow packaging of the nucleic acids encoding toxic agent or ribozyme of the invention, but prevent packaging of nucleic acids encoding one or more viral genes or plasmids. Such strategies allow for construction of viral delivery systems which have increased safety (e.g., when used in connection with therapeutics of the invention).

In a specific embodiment, the invention provides a bacteriophage able to package/deliver Transfer plasmid in P1 virions which will infect a pathogenic bacterial target. In another specific embodiment, bacteriophage P1 (PAC site) knockouts able to 10 package/deliver Transfer plasmid DNA but unable to incorporate P1 DNA thus preventing horizontal transfer of undesirable products to non-pathogenic indigenous microflora. In another specific embodiment of the invention, the phage delivery system comprises a Transfer plasmid carrying the genes encoding the antimicrobial agents, a plasmid origin of replication, the P1 lytic origin of replication and a minimal PAC site (e.g., such as the minimal P1 pac site as shown in FIG. 12, SEQ ID NO:7). In this embodiment, the plasmid is maintained in a bacteriophage P1 lysogen unable to package its own DNA. The defective lysogen provides all the replication factors needed to activate the P1 origin of replication on the transfer plasmid and all the structural components necessary to form mature virions. The lysogen also carries the c1.100 temperature-sensitive repressor mutation. C1 is responsible for the repression of functions leading to vegetative phage production. Induction of the lysogen by a temperature shift results in multiplication of DNA, packaging of the transfer plasmid into P1 phage heads and lysis of the production strain. Virions are harvested and used to deliver the Transfer plasmid to the pathogen. The phagehead contains multiple copies of Transfer plasmid DNA and is targeted to pathogenic bacteria by the bacteriophage's natural receptor mediated mechanisms. Upon delivery, plasmid DNA recircularises and expression of the toxic agent under the control of environmental, virulence-regulated or species-specific promoters results in rapid cell death.

In specific embodiments, the invention provides novel Transfer plasmids encoding toxic agents which may be used in combination with a bacteriophage delivery system in order to treat a bacterial infection in a host.

Bacteriophage Lamda

Another example of a system using bacteriophage virions to package DNA carrying ribozymes and/or toxic agents directed against *E. coli* is the bacteriophage lamda. Similar strategies are used to generate virions capable of delivering ribozymes and/or toxic agents directed against other microorganisms. The virions used to package the DNA can be species-specific, such as the virion derived from the bacteriophage lambda coat, or they can possess a broader host range, such as virion derived from bacteriophage P1, as described above. Broad host-range viruses facilitate production of the antimicrobial agents without the loss of species specificity because species-specific promoters are used to direct the transcription of the ribozymes which are directed against species-specific targeted RNA sequences. For example, a lamda bacteriophage entails the use of a plasmid carrying the ribozyme and/or toxic agent, a plasmid origin of replication, a selectable marker for plasmid maintenance, the minimal lambda origin of replication, and cos sites, which are required for packaging of DNA into lambda virions. This plasmid is maintained in a lambda lysogen that is defective in integration/excision and recombination functions. The defective lysogen provides all of the replication factors needed to activate the lambda origin of replication on the plasmid and all of the structural components needed to form mature virions; however, the lysogen is not able to replicate and package its own DNA into the virions. The lysogen may also carry a temperature-sensitive repressor mutation (such as the cI857).

Other Viral Vectors

Retroviral vectors are also commonly used to deliver genes to host cells both in vivo and ex vivo. Retroviral vectors are extremely efficient gene delivery vehicles that cause no detectable harm as they enter the cells. The retroviral nucleic acid may integrate into host chromosomal DNA allowing for long-term persistence and stable transmission to future progeny, such a vector would be useful for the delivery of a toxic agent and/or ribozyme(s) used to target a cellular gene product involved in a chronic or hereditary disorder or to target a viral gene or a microbial gene or a parasitic gene involved in a chronic or persistent infection. An example of an appropriate retroviral vector are, lentiviruses which have the advantage of infecting and transducing non-dividing cells. In such an embodiment, a lentiviral vector encoding a packagable RNA vector genome operably linked to a promoter in which all the functional retroviral auxiliary genes are absent, is used to transfer the DNA encoding the toxic agent and/or ribozyme of the present invention. Examples of such vectors are described in WO 98/17815, WO 98/17816 and WO 98/17817, each of which is incorporated herein by reference in their entirety.

In yet another embodiment, non-integrating viral vectors which infect and transduce non-dividing cells, such as adenoviral vectors may be used to deliver the toxic agent and/or ribozymes of the present invention. Adenoviral vectors have several advantages because the use of such vectors avoids risks associated with permanently altering the host cell genome or of promoting insertional mutagenesis. Adenoviruses are one of the best developed non-integrating viral vectors and can be used to transfer expression cassettes of up to 75 kb. Recombinant adenoviruses can be produced at very high titers, is highly infectious and efficiently transfers genes to a wide variety of non-replicating and replicating cells and is ideal for in vivo mammalian gene transfer.

Adenovirus-based vectors are relatively safe and can be manipulated to encode the desired toxic agent and/or ribozymes and at the same time to be inactivated in terms of their ability to replicate in a normal lytic viral life cycle. Adenovirus has a natural tropism for airway epithelia. Therefore, adenovirus-based vectors are particularly preferred for respiratory gene therapy applications. In a particular embodiment, the adenovirus-based gene therapy vector comprises an adenovirus 2 serotype genome in which the E1a and the E1b regions of the genome, which are involved in early stages of viral replication have been deleted and replaced by nucleotide sequences of interest. In a further embodiment, the adenovirus-based gene therapy vector contains only the essential open reading frame (ORF3 or ORF6 of adenoviral early region 4 (E4) and is deleted of all other E4 open reading frames, or may additionally contain deletions in the E3 regions (e.g., see U.S. Pat. No. 5,670,488, incorporated herein by reference in its entirety). In another embodiment, the adenovirus-based therapy vector used may be a pseudo-adenovirus (PAV), which contain no harmful viral genes and a theoretical capacity for foreign material of nearly 36 kb.

In another embodiment, adeno-associated virus (AAV) systems may be used to deliver the toxic agent and/or ribozymes of the present invention. AAV has a wide host range and AAV vectors have currently have been designed which do not require helper virus. Examples of such AAV vectors are described in WO 97/17458, incorporated herein by reference in its entirety.

Vaccinia viral vectors may be used in accordance with the present invention, as large fragments of DNA are easily cloned into its genome and recombinant attenuated vaccinia variants have been described (Meyer, et al., 1991, J. Gen. Virol. 72:1031-1038). Orthomyxoviruses, including influenza; Paramyxoviruses, including respiratory syncytial virus and Sendai virus; and *Rhabdoviruses* may be engineered to express mutations which result in attenuated phenotypes (see U.S. Pat. No. 5,578,473, issued Nov. 26, 1996). These viral genomes may also be engineered to express foreign nucleotide sequences, such as the selected toxic agent and/or ribozymes of the present invention (see U.S. Pat. No. 5,166, 057, issued Nov. 24, 1992, incorporated herein by reference in its entirety). Reverse genetic techniques can be applied to manipulate negative and positive strand RNA viral genomes to introduce mutations which result in attenuated phenotypes, as demonstrated in influenza virus, Herpes Simplex virus, cytomegalovirus and Epstein-Barr virus, Sindbis virus and poliovirus (see Palese et al., 1996, Proc. Natl. Acad. Sci. USA 93:11354-11358). These techniques may also be utilized to introduce foreign DNA, i.e., the selected toxic agent and/or ribozyme, to create recombinant viral vectors to be used in accordance with the present invention. In addition, attenuated adenoviruses and retroviruses may be engineered to express the toxic agent and/or ribozymes. Therefore, a wide variety of viruses may be engineered to design the ribozymes delivery vehicles of the present invention.

The viral vectors, of the present invention may be engineered to express the toxic agents and/or ribozymes in a tissue specific manner. For example, the promoter of the carcinoembryonic antigen (LEA) is expressed in a proportion of breast, lung and colorectal cancers, but rarely in healthy tissues. In order to target a hepatoma, the α-fetoprotein (AFP) promoter whose activity is restricted to malignant cells. Proliferating cells can be targeted with a flt-1 promoter, which has been shown to allow preferential targeting of proliferating endothelial cells. See Miller et al., 1997, Human Gene Therapy 8:803-815, incorporated herein by reference in its entirety.

5.3.2. Abiologic Delivery Vehicles

Abiologic delivery of one or more toxic agents and/or ribozymes is accomplished by a variety of methods, including packaging plasmid DNA carrying the gene(s) that codes for the toxic agent(s) and/or ribozyme(s) into liposomes or by complexing the plasmid DNA carrying the gene(s) that codes for the toxic agent(s) and/or ribozyme(s) with lipids or liposomes to form DNA-lipid or DNA-liposome complexes. The liposome is composed of cationic and neutral lipids commonly used to transfect cells in vitro. The cationic lipids complex with the plasmid DNA and form liposomes.

A liposome is provided, comprising a nucleic acid comprising a pathogen-specific promoter operably linked to a sequence encoding a trans-acting ribozyme comprising a) a 5' autocatalytically cleaving ribozyme sequence, b) a catalytic ribozyme comprising a target RNA-specific binding site and c) a 3' autocatalytically cleaving ribozyme sequence.

A liposome is provided, comprising a nucleic acid encoding a pathogen-specific promoter operably linked to a sequence encoding one or more toxic agents is provided.

The liposome of the invention, wherein the nucleic acid encodes more than one trans-acting ribozyme and/or more than one toxic agent is provided. The liposome can comprise any ribozyme-encoding nucleic acid, or any toxic agent encoding nucleic agent particularly those described herein. Such nucleic acids may be operably linked to a tissue-specific or pathogen-specific promoter.

The liposomal delivery systems of the invention can be used to deliver a nucleic acid comprising a tissue-specific promoter operably linked to a sequence encoding a multi-ribozyme comprising a) a 5' autocatalytically cleaving ribozyme sequence, b) a catalytic ribozyme comprising a target RNA-specific binding site and c) a 3' autocatalytically cleaving ribozyme sequence.

The liposome delivery system of the invention can be used to deliver a nucleic acid comprising a tissue-specific promoter operably linked to a sequence encoding one or more toxic agents. The liposome delivery system of the invention can be used to deliver a nucleic acid comprising a pathogen-specific promoter operably linked to a sequence encoding one or more toxic agents.

Cationic and neutral liposomes are contemplated by this invention. Cationic liposomes can be complexed with a negatively-charged biologically active molecule (e.g., DNA) by mixing these components and allowing them to charge-associate. Cationic liposomes are particularly useful when the biologically active molecule is a nucleic acid because of the nucleic acids negative charge. Examples of cationic liposomes include lipofectin, lipofectamine, lipofectace and DOTAP (Hawley-Nelson et al., 1992, Focus 15(3):73-83; Felgner et al., 1987, Proc. Natl. Acad. Sci. U.S.A. 84:7413; Stewart et al., 1992, Human Gene Therapy 3:267-275). Procedures for forming cationic liposomes encasing substances are standard in the art (Nicolau et al., 1987, Methods Enzymol. 149:157) and can readily be utilized herein by one of ordinary skill in the art to encase the complex of this invention.

In yet another embodiment of the present invention, the plasmid DNA carrying the gene(s) that codes for the toxic agents and/or ribozymes of the invention are complexed with liposomes using an improved method to achieve increased systemic delivery and gene expression (Templeton et al., 1997, Nature Biotechnology 15: 647-652, incorporated herein by reference in its entirety). In accordance with the present invention, an improved formulation of cationic lipids which greatly increase the efficiency of DNA delivery to host cells, with extended half-life in vivo and procedures to target specific tissues in vivo. For example, but not by limitation, peptides and proteins may be engineered to the outer lipid bilayer, such as liver-specific proteins, leads to substantially enhanced delivery to the liver etc.

In one embodiment of the present invention, systemic delivery and in vivo and ex vivo gene expression is optimized using commercially available cationic lipids, e.g., dimethyl-dioctadeclammonium bromide (DDAB); a biodegradable lipid 1,2-bis(oleoyloxy)-3-(trimethylammonio) propane (DOTAP); these liposomes may be mixed with a neutral lipid, e.g., L-α dioleoyl phosphatidylethanolamine (DOPE) or cholesterol (Chol), two commonly used neutral lipids for systemic delivery. DNA:liposome ratios may be optimized using the methods used by those of skill in the art (e.g., see Templeton et al., 1997, Nature Biotechnology 15: 647-152, incorporated herein by reference in its entirety).

In yet another embodiment of the present invention, the plasmid DNA carrying the nucleic acids encoding the toxic agents and/or ribozymes of the invention may be delivered via polycations, molecules which carry multiple positive charges and are used to achieve gene transfer in vivo and ex vivo. Polycations, such as polyethilenimine, may be used to achieve successful gene transfer in vivo and ex vivo (e.g., see Boletta et al., 1996, J. Am. Soc. Nephrol. 7: 1728, incorporated herein by reference in this entirety.)

The liposomes may be incorporated into a topical ointment for application or delivered in other forms, such as a solution which can be injected into an abscess or delivered systemically, or delivered by an aerosol.

Plasmid DNA coding for the ribozymes or toxic agent is used rather than preformed ribozymes or toxic agent for the following reasons. Plasmid DNA allows the targeted cells to produce the toxic agent or ribozyme and, thus, results in a higher delivered dose to the cell than can be expected by delivery of ribozyme RNA or toxic agent via liposome. The DNA also provides specificity of action based on target sequence specificity. The liposomes deliver their DNA to any cell in the area of administration, including cells of the host. The promoter driving the transcription of the toxic agent or ribozyme is specific for the targeted microorganism and, thus, will be inactive in other cell types. Therefore, liposomal delivery of DNA coding for the toxic agent or ribozyme provides amplification and specificity. The present invention relates to promoter elements which are pathogen-specific or tissue-specific. Such promoter elements are used to achieve pathogen-specific or tissue-specific expression of the toxic agent(s) and/or ribozyme(s) of the present invention. The invention also relates use of an origin of replication which modulates specificity of the replication or copy number of a vector or plasmid in a cell or pathogen.

5.3.2.1. Delivery & Expression Using Multi-Ribozymes

In another embodiment of the invention, expression of a toxic agent is directed by a tissue-specific, pathogen-specific, and/or target-specific ribozyme or ribozyme cassette. The invention provides ribozymes that have the unique characteristic of being both target RNA-specific in their catalytic action, and tissue-specific or pathogen-specific in their expression. A ribozyme can be tissue-specific in the case of treating tissue-specific disease, or it can be pathogen-specific in the case of treating a pathogen such as E. coli. Multi-ribozymes may have one or more target-specific ribozyme(s) (e.g., a trans-acting catalytic ribozyme) as well as elements which control tissue-specific or pathogen-specific expression.

In one embodiment, the nucleic acids of the invention comprise a tissue-specific promoter operably linked to a sequence encoding a) a 5' autocatalytically cleaving ribozyme sequence, b) a catalytic ribozyme comprising a target RNA-specific binding site and c) a 3' autocatalytically cleaving ribozyme sequence.

The tissue-specific promoter in the ribozyme-producing construct results in tissue-specific expression of the ribozyme in tissue(s) that actively transcribe RNA from the selected promoter. Thus, only the target RNA in tissue that utilize the promoter will be cleaved by the ribozyme.

Further, in accordance with the present invention, the multi-ribozyme may consist of one or more ribozyme cassettes. Each cassette in turn may consist of a catalytic core and one or more flanking sequences. In one embodiment, the ribozyme cassette may consist of a 5' autocatalytically cleaving ribozyme sequence, a core catalytic ribozyme comprising a trans-acting ribozyme and a 3' autocatalytically cleaving ribozyme. In yet another embodiment, the catalytic core contains sequences encoding one or more toxic agent(s). In other embodiments, the multi-ribozymes comprise a cassette including, the enhanced 5' and 3' autocatalytically cleaving ribozyme sequence. In another embodiment, the multi-ribozymes contain one or more internal trans-acting ribozymes. In a preferred embodiment, the multi-ribozymes of the present invention include, but are no limited to triple ribozyme cassettes. In another embodiment, multi-ribozymes include but are not limited to one or more triple ribozyme cassettes linked together. In yet another embodiment, the multi-ribozyme comprises a ribozyme cassette containing one or more internal trans-acting ribozyme. In an additional embodiment, the multi-ribozyme comprises a series of one or more ribozyme cassettes containing one or more internal trans-acting ribozymes or any combination thereof. In further embodiments, the multi-ribozyme cassettes or toxic agent(s) are expressed in a tissue-specific or pathogen-specific manner. In a preferred embodiment of the invention, pathogen-specific expression is coupled to a pathogen-specific promoter.

5.4. Promoter Selection

Promoter selection is accomplished using techniques that are available in the art. As used herein, regulatory elements include but are not limited to, inducible and non-inducible promoters, enhancers, operators and other elements known to those skilled in the art that drive and regulate expression. Specifically, the invention provides inducible promoters which have increased transcriptional control and high expression levels. The promoter can be a naturally occurring strong, intermediate or weak constitutively expressed or regulated promoter from the targeted microorganism, or an artificially contrived constitutively expressed or regulated promoter containing either a strong, intermediate or weak consensus sequence that delivers desired levels of toxic agent or ribozyme expression in the targeted microbe.

Promoters specific for the target (e.g., a specific pathogen, genus, etc.) in question can be selected by screening genomic sequences for the ability to activate a promoterless reporter gene. The promoterless reporter gene is based on the strategy developed for use with plasmid pMC1871 (Casadaban et al., 1983, Meth. Enzymol. 100:293). For non-viral pathogens, plasmid capable of stable replication and maintenance in the microorganism understudy is modified by standard molecular biology techniques to carry the coding region of a reporter gene (Sambrook et al. latest edition). The reporter gene can be any of a number of standard reporter genes including but not limited to the lacZ gene of $E.\ coli$, which codes for β-galactosidase. Total genomic DNA is isolated from cells of the pathogen, cleaved with restriction endonucleases to yield fragments of a few hundred basepairs on average. These fragments are then ligated into a unique restriction endonuclease cleavage site at the 5' end of the reporter gene coding region, creating a library of plasmids. The library is then transformed into the pathogen by standard techniques and the resulting transformants are screened for expression of the reporter gene. In the case of lacZ, the transformants can be plated onto medium containing the chromogenic galactosidase substrate X-Gal (5-bromo-4-chloro-3-indolyl-D-galactoside). Transformants that contain a plasmid with an insert carrying a promoter will express β-galactosidase and will turn blue on X-Gal plates. The intensity of the blue color is relative to the level of expression; promoters of different strength can be selected based on the intensity of the blue color.

The above-described screening procedure can be modified to identify regulated promoters. For example, promoters that are regulated by carbon source availability can be screened on plates that contain different carbon sources. Other modifications are possible and will depend, in part, on the organism in question. To test for species-specificity, the identified promoters are transferred to promoterless reporter plasmids capable of replication and maintenance in a different organism. Truly species-specific or pathogen-specific promoters will not activate the expression of the reporter gene in any other species. Obvious modifications can be used to identify and test artificial promoters composed of synthetic oligonucleotides inserted into the promoterless reporter plasmid.

In one embodiment, the nucleic acids of the invention comprise a tissue-specific promoter operably linked to a sequence encoding a 5' autocatalytically cleaving ribozyme sequence, one or more catalytic target-specific trans-acting ribozymes or one or more toxic agents and a 3' autocatalytically cleaving ribozyme sequence.

The tissue-specific promoter in the ribozyme-producing construct results in tissue-specific expression of the ribozyme in tissue(s) that actively transcribe RNA from the selected promoter. Thus, only the target RNA in tissue that utilize the promoter will be cleaved by the ribozyme. The pathogen-specific promoter binding site in the ribozyme-producing construct results in pathogen-specific expression of the ribozyme in pathogens or microbes that actively transcribe RNA from the selected promoter. Thus, only the target RNA in pathogens that utilize the promoter will be cleaved by the ribozyme.

Tissue-specific promoters can be used in the present nucleic acid constructs. Examples of these promoters include the sequences for probasin-promoter, a promoter-specific for prostate epithelium prostate-specific antigen (prostate), keratin, k7 (epidermal sabaceus glands), albumin (liver), fatty acid binding protein (ileum), whey acidic protein (breast), lactalbumin, smooth muscle actin (smooth muscle), etc. In a specific embodiment, a mouse albumin promoter/enhancer is used which consists of nucleotides 338-668 from Genbank accession # U04199, followed by the sequence gagtcgacggatccgg (SEQ ID NO:13), followed by nucleotides 1762-1846 from accession # J04738, followed by the nucleotide sequence tgggggtgggggtgggg (SEQ ID NO:14) followed by nucleotides 1864-2063 of accession # J04738. In one embodiment, the mouse promoter/enhancer is active in hepatocyte (e.g., human hepatocytes, hepatocyte cultures, etc.) and is useful for tissue-specific expression in liver tissue. It will also be clear that target-specific promoters not yet identified can be used to target expression of the present ribozymes to the selected tissue(s). Once a target-specific promoter is identified its binding sequence can be determined by routine methods such as sequence analysis may be used. The promoter is defined by deletion analysis, mutagenesis, footprinting, gel shifts and transfection analyses (Sambrook et al., *Molecular Cloning: A Laboratory Manual,* 2nd Ed., Cold Spring Harbor Laboratory, Cold Spring Harbor, N.Y., 1989). Pathogen-specific promoters can be used in the present nucleic acid constructs.

5.4.1. Bacterial Specific Promoters/Expression

The present invention provides bacterial promoters that allow for tight regulation of transcription and enhanced expression. In one embodiment, a novel promoter called LEASHI has been constructed from three elements (see FIG. 1). The first element, termed RIP is a combination of two consensus sites at −10(TATAAT) and −35(TTGACA) located with respect to transcription initiation. The second element is based on the lacI repressor binding sequence (termed lac operator sequence) which is placed between the −10 and −35 consensus sites. This is in contrast to the conventional lac and tac promoters where the lac operator is found downstream of the −10 consensus element. Placement of the lac operator between the −10 and −35 sites, more effectively blocks RNA polymerase binding to the promoter, thus enhancing transcriptional control from the promoter. Thus, the levels of lacI repressor protein present, which binds to the operator sequence and hence determines the rate of transcription, are controlled in two ways; 1) by endogenously expressed lacI protein and 2) by a plasmid expressing the lacI gene. Under normal conditions, the lacI repressor protein binds to the lac operator sequence and prevents transcription by blocking RNA polymerase binding. The promoter is 'switched on' following the addition of isopropyl B-D-thiogalacto pyranoside, which binds and subsequently titrates out the repressor protein. RNA polymerase can then bind to the promoter and transcription can proceed.

The third element of the LEASHI promoter is termed the UP element. The UP element is an adenine/thymine rich sequence which is placed immediately upstream of the −35 element. Addition of the UP element, further increases expression from this promoter. Accordingly, the invention provides the use of a LEASHI promoter to express the toxic agents of the invention.

In a specific embodiment of the invention, the promoter which is operably linked to a nucleic acid encoding a toxic agent or ribozyme is the LEASHI promoter.

In specific embodiment, a ribozymes of the invention is operably linked to a LEASHI promoter. In another specific embodiment of the invention, a toxic agent of the invention is operably linked to a LEASHI promoter.

In a specific embodiment, the invention encompasses expression of DicF1 from a ribozyme cassette under the control of a regulatable promoter, such as the LEASHI promoter.

In another embodiment of the invention, the lacI operator sequence of the LEASHI promoter is placed 5' of the −35 consensus site. In another embodiment of the invention, the lacI operator sequence of the LEASHI promoter is placed 3' of the −10 consensus site. In other embodiment of the invention, one or more additional lacI operator sequences are added to the LEASHI promoter and are placed 5' to the −35 consensus site and/or 3' of the of the −10 consensus site.

In other specific embodiments, the invention provides for the use of an anr, arc, or proC promoter. Both are transcriptionally off in *E. coli* and on in *Pseudomonas aeruginosa*. These promoters provide the advantage of allowing controlled expression of the toxic agents in the pathogen (*Pseudomonas*), while allowing the packaging strain (*E. coli*) to be protected from the toxic actions of the toxic agent therapeutic. Such promoters are particularly useful to facilitate manufacturing of the delivery vehicle. Such promoters also enable bacterial specific targeting of the gene therapeutic in the patient. In specific embodiments, an anr promoter is operably linked to a sequence encoding a toxic agent (such as doc, gef, chpBK, or kicB, etc), and may be used, for example, for the eradication of *Pseudomonas*.

In other specific embodiments, the invention provides for the use of the TSST-1 promoter. TSST-1 is an environmentally regulated *staphylococcus*-specific promoter. TSST-1 is useful to express doc or other toxic agents. A *staphylococcus* specific phage capable of delivering the transfer plasmid into *S. aureus* strains is used to specifically target the Staphylococcal pathogen.

Other classical bacterial inducible promoters are renowned for their inability to tightly control transcription, and a significant level of background expression is characteristically observed. A significant advantage of the promoter of the present invention is that it will alleviate the high levels of background commonly observed in inducible promoters. A limiting factor leading to high background levels of transcription when a promoter of interest is on a high-copy number plasmid is due to the lack of repressor molecules available to bind to the promoters. The present invention overcomes this problem by using a lacI expression plasmid and secondly, by placement of the lac operator between the −35 and −10 consensus elements which more effectively blocks transcription during normal conditions. Furthermore, the UP element placed immediately upstream of the −35 region enhances transcription from the core promoter.

The invention also relates to the rrnB promoter. In one embodiment of the invention, the promoter is the rrnB promoter is modified such that one or more lacI operator sites are added to the promoter. An example of such a modified rrnB promoter is shown in FIG. 1B. In another embodiment of the invention, the lad operator sequence of the rrnB promoter (SEQ ID NO:2) is placed 3' of the −10 consensus site. In other embodiment of the invention, one or more additional lacI operator sequences are added to the rrnB promoter and are placed 5' to the −35 consensus site and/or 3' of the of the −10 consensus site.

5.5. Host Cells

The present invention encompasses the expression of the toxic agents and/or ribozymes in primary cells, animal, insect, fungal, bacterial, and yeast cells for in vitro screening assay and ex vivo gene therapy. The present invention also encompasses the expression of the toxic agents and/or ribozymes in cell lines for in vitro screening assay and ex vivo gene therapy. In accordance with the present invention, a variety of primary or secondary cells or cell strains may be used including but not limited to cells isolated from skin, bone marrow, liver, pancreas, kidney, adrenal and neurological tissue to name a few. Other cell types that may be used in accordance with the present invention are immune cells (such as T-cells, B-cells, natural killer cells, etc.), macrophages/monocytes, adipoctyes, pericytes, fibroblasts, neuronal cells, reticular cells etc. In a further embodiment, secondary cell lines may be used as engineered responsive cells and tissues in accordance with the present invention, including, but not limited to hepatic cell lines, such as CWSV, NR, Chang liver cells, or other cell lines such as CHO, VERO, BHK, Hela, COS, MDCK, 293, 373, HUVEC, CaSki and W138 cell lines. A toxic agent or ribozyme of the invention may also be expressed in any cell line which is not sensitive to the effects of the toxic agent or ribozyme (e.g., a cell which is resistant to the particular toxic agent or ribozyme, or a cell which co-expresses a neutralizing agent or antidote).

For long term, high-yield production of recombinant proteins, stable expression is preferred. For example, cell lines which stably express the selected toxic agent and/or ribozyme may be engineered. When a toxic agent is to be stably expressed, expression may be controlled by an inducible promoter, or, the cell may be engineered to co-express an antidote to the toxic agent, in order to allow the cell to survive during production of a toxic agent. Rather than using expression vectors which contain viral origins of replication, host cells can be transformed with DNA controlled by appropriate expression control elements (e.g., promoter sequences, enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to grow to form foci which in turn can be cloned and expanded into cell lines. This method may advantageously be used to engineer cell lines. This method may advantageously be used to engineer cell lines which express the selected gene products. Such cell lines would be particularly useful in screening and evaluation of compounds that affect the endogenous activity of the selected gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

5.6. Targets

The present invention provides a toxic agent or a trans-acting ribozyme which targets any cellular, viral, bacterial, fungal, or other single cellular or multicellular organism from any known taxonomic family, genus, or species. Another embodiment of the invention provides a toxic agent which is lethal or toxic to a pathogen such as a bacteria, fungus, yeast, diseased cell. Such toxic agents may be delivered to the pathogen by the methods of the invention. The microorganisms may be any virus, nonvirus, bacterium, or lower eukaryotes such as fungi, yeast, parasites, protozoa, or other eukaryotes that may be considered pathogens of humans, animals, fish, plants, or other forms of life. In several embodiments, the targets of the antimicrobial ribozyme therapeutics described herein are the RNAs of invading or normal flora microorganisms. In other embodiments, the targets of the antimicrobial toxic agent therapeutics described herein include RNAs, proteins, genes and other molecules of invading or normal flora microorganisms. Thus, the invention has important implications in human and veterinary medicine.

The toxic agents of the present invention may be engineered to target essential genes, gene products, or processes necessary for growth of parasites, bacteria, virus life cycles, etc., and expression can be driven with tissue-specific or pathogen-specific promoters. The toxic agents or trans-acting catalytic ribozymes of the present invention may be engineered to target a wide variety of cellular RNAs, tumor or cancer associated with RNAs, bacterial RNAs, parasitic RNA etc. For example, ribozyme targets sites are indicated in Tables 11, 13 and 13 herein. The toxic agent or trans-acting ribozyme can be targeted to noncellular RNAs necessary for growth of parasites, bacteria, virus life cycles, etc., and expression can be driven with tissue-specific or pathogen-specific promoters.

The virion construct used in this method can comprise any nucleic acid encoding a toxic agent or ribozyme, particularly those described herein targeted to essential genes of the pathogen or diseased cell. The virion can be a bacteriophage, or other virus selected for its ability to target a specific cell-type, microorganism or animal. The bacteriophage can be lambda, P1, Phi-11 or other phage. When P1 is the virion, the Tranfer plasmid can further comprise a PAC site and PAC ACB genes. This construct is preferred when using P1. Alternatively, the virion can be selected because it has a broad range of targets.

Important examples which are specifically presented in the application are:

A) Use of the LEASHI promoter with a Bacterial target (such as *E. coli*) to direct expression of the toxic agent such as doc, gef, chpBK, kicB or DicF1;

B) Use of the LEASHI promoter with a Bacterial target (such as *E. coli*) to direct expression of the toxic agent comprising Sof sense RNA;

C) Use of the anr, arc, or proC promoter with a *Pseudomonas* target (such as *P. aeruginosa*) to direct expression of a toxic agent such as doc, gef, chpBK, kicB or DicF1;

D) Use of the TSST-1, hla, or SrcB promoter with a *Staphylococcus* target (such as *S. aureus*) to direct expression of the toxic agent such as doc, gef, chpBK, kicB, pemK, hok, relF, sigB, or lysostaphin;

E) Use of the albumin promoter with a Hepatitis B virus target (chosen to cleave the viral RNA pregenome, S protein, and polymerase/and x protein transcripts using the same ribozyme target site);

F) Use of the albumin promoter with Hepatitis B virus and Hepatitis C targets (using trans-acting ribozyme target sites on both Hepatitis B virus and Hepatitis C);

G) Use of generic promoters active in erythrocytes, using a ribozyme targeted to highly conserved regions of the EMP-1 protein family from *P. falciparum*, which are necessary for cytoadherence and antigenic variation in malaria; and H) Use of the keratin 7 promoter, with trans-acting ribozymes targeted to a specific sites near the translational start site of the E6 protein, a site known to be critical for expression of both the E6 and E7 proteins which are intimately involved in cervical carcinogenesis, as well as a more 3' site in a highly conserved region of the E6 protein.

Examples of bacterial pathogens that can be targeted by a toxic agent or trans-acting ribozyme of the present invention include, but are not limited to, species of the following genera: *Salmonella, Shigella, Chlamydia, Helicobacter, Yersinia, Bordatella, Pseudomonas, Neisseria, Vibrio, Haemophilus, Mycoplasma, Streptomyces, Treponema, Coxiella, Ehrlichia, Brucella, Streptobacillus, Fusospirocheta, Spirillum, Ureaplasma, Spirochaeta, Mycoplasma, Actinomycetes, Borrelia, Bacteroides, Trichomoras, Branhamella, Pasteurella, Clostridium, Corynebacterium, Listeria, Bacillus, Erysipelothrix, Rhodococcus, Escherichia, Klebsiella, Pseudomanas, Enterobacter, Serratia, Staphylococcus, Streptococcus, Legionella, Mycobacterium, Proteus, Campylobacter, Enterococcus, Acinetobacter, Morganella, Moraxella, Citrobacter, Rickettsia, Rochlimeae,* as well as bacterial species such as: *P. aeruginosa; E. coli, P. cepacia, S. epidermis, E. faecalis, S. pneumonias, S. xylosus, S. aureus, N. meningitidis, S. pyogenes, Pasteurella multocida, Treponema pallidum,* and *P. mirabilis.*

The pathogen of the present invention can also include, but is not limited to pathogenic fungi such as *Cryptococcus neoformans; Blastomyces dermatitidis; Aiellomyces dermatitidis; Histoplasma capsulatum; Coccidioides immitis; Candida* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata; Trichophyton* species, *Microsporum* species and *Dermatophyres* species, as well as any other yeast or fungus now known or later identified to be pathogenic.

Furthermore, the pathogen of the present invention can be a parasite, including, but not limited to, members of the Apicomplexa phylum such as, for example, *Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus* and *Gregarina* spp.; *Pneumocystis carinii*; members of the Microspora phylum such as, for example, *Nosema, Enterocytozoon, Encephalitozoon, Septata, Mrazekia, Amblyospora, Ameson, Glugea, Pleistophora* and *Microsporidium* spp.; and members of the Ascetospora phylum such as, for example, *Haplosporidium* spp., as well as species including *Plasmodium falciparum, P. vivax, P. ovale, P. malaria; Toxoplasma gondii; Leishmania mexicana, L. tropica, L. major, L. aethiopica, L. donovani, Trypanosoma cruzi, T. brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidium parvum; Pneumocytis carinii, Babesia bovis, B. divergens, B. microti, Isospora belli, L. hominis; Dientamoebafragilis; Onchocerca volvulus; Ascaris lumbricoides; Necator americanis; Ancylostoma duodenale; Strongyloides stercoralis; Capillaria philippinensis; Angiostrongylus cantonensis; Hymenolepisnana; Diphyllobothrium latum; Echinococcus granulosus, E. multilocularis; Paragonimus westermani, P. caliensis; Chlonorchis sinensis; Opisthorchisfelineas, G. Viverini, Fasciola hepatica, Sarcoptes scabiei, Pediculus humanus; Phthirlus pubis*; and *Dermatobia hominis*, as well as any other parasite now known or later identified to be pathogenic.

Examples of viral pathogens include, but are not limited to, retroviruses (human immunodeficiency viruses), herpes viruses (herpes simplex virus; Epstein Barr virus; varicella zoster virus), orthomyxoviruses (influenza), paramyxoviruses (measles virus; mumps virus; respiratory syncytial virus), picoma viruses (Coxsackie viruses; rhinoviruses), hepatitis viruses (hepatitis C), bunyaviruses (hantavirus; Rift Valley fever virus), arenaviruses (Lassa fever virus), flaviviruses (dengue fever virus; yellow fever virus; chikungunya virus), adenoviruses, bimaviruses, phleboviruses, caliciviruses, hepadnaviruses, orbiviruses, papovaviruses, poxviruses, reoviruses, rotaviruses, rhabdoviruses, parvoviruses, alphaviruses, pestiviruses, rubiviruses, filiviruses, coronaviruses, as well as any virus of the family of picomaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae, and any other virus now known or later identified to be pathogenic.

5.7. Target Selection

One critical component in the development of the therapeutics of the invention is the selection of appropriate targets.

Toxic Agent Targets

The inventions toxic agents are selected based on their ability to inhibit the growth of a pathogen or selected cell or cause lethality in a pathogen or selected cell, or render a pathogen or selected cell less fit. Several specific examples of toxic agents are described herein which serve to illustrate the selection of a toxic agent of the invention.

For example, a toxic agent may be an addiction system toxin (such as doc). Doc encodes a toxin which is translationally coupled to a protein called phd. Phd is an antidote to doc, and acts to neutralize the toxic effects of doc. The two proteins, phd and doc form an operon on the P1 plasmid in which phd precedes doc. Further, the phd gene contains a ribosome entry site and is translated efficiently. The native doc gene however, lacks a recognizable ribosome entry site and is translated poorly. Thus, doc was selected because of its potential toxicity when expressed in a cell or pathogen lacking the corresponding antidote, phd. In this embodiment, doc has been engineered to be uncoupled from phd. For example, doc is engineered into a separate plasmid from phd. The plasmid containing doc has also been engineered such that a ribosome entry site has been constructed upstream of the nucleic acids encoding doc in order to increase the levels of translation of doc. This plasmid is containing the toxic agent and/or ribozyme of the invention is called the Transfer plasmid. In one specific embodiment of the invention, the Transfer plasmid encodes the toxic agent doc.

A packaging strain (e.g., bacteria cell) is then used to package the Transfer plasmid containing doc into a bacteriophage phage head. The packaging strain cells contain the P1 plasmid as well as the Transfer plasmid with the uncoupled doc and ribosome entry site. The packaging strain may also include a third plasmid, if necessary, which encodes additional phd protein which can act to protect the packaging strain against the toxicity of doc (e.g., if the promoter of the Transfer plasmid is leaky and leads to production of doc in the packaging cell).

Thus, the packaging strain acts to package the transfer plasmid containing the toxic agent (such as doc) into phage heads or virions. Phage lysates of the packaging strain contain the infectious bacteriophage virions.

The phage lysates are then used to infect a selected pathogen (e.g., *E. coli, P. aerugunosa*, etc.). Further, the phage lysate may be used to prepare a therapeutic of the invention, such as a pharmaceutical preparation. Phage may be delivered to a bacteria or pathogen or a host with a pathogenic infection by methods described herein, or by any method known in the art. For example, the phage lysates may be lyophilized and delivered to a host in need of treatment for a bacterial infection, fungal infection, etc.

The above targeting method, wherein the virion is a bacteriophage is provided. The bacteriophage can be lambda, P1 or other phage. The targeting method, wherein the Transfer plasmid further comprises a PAC site and PAC ABC genes is also provided. The bacteriophage P1 which is engineered to be packaging deficient is also provided. This construct is preferred when using P1.

Antisense Targets

A toxic agent of the invention may be an antisense molecule selected to target an antidote of a toxic protein, or selected to target an essential RNA critical to the survival of a pathogen or selected cell. The proposed target of the toxic antisense molecule of the invention may also be the RNA of any gene which plays a critical role in the survival of the pathogen, or which is essential to the pathogen's life cycle. The present invention also encompasses modifications to naturally occurring antisense molecules which modulate the expression of an essential gene product of a pathogen. For example, as described below, one proposed target of an antisense of the invention is the ftsZ gene whose gene product plays a critical role in the initiation of cell division of *E. coli*. For example, the toxic agent may be an antisense molecule which is constructed to be modified and enhanced such that is it more homologous to its target RNA. Thus, as in the case of DicF, the antisense sequence has been modified and enhanced to engineer the DicF1 antisense toxic agent, which has increased complementarity to its target RNA. Further, the DicF1 or DicF1-like antisense molecule has enhanced properties in that it may be expressed and delivered by the methods of the invention, thus providing the target cell with increased levels of the toxic antisense RNA.

Third, a toxic agent may be selected to target an essential antisense molecule. Thus, a toxic agent may be a sense molecule which is designed to be complementary to an essential antisense RNA. An example of an essential antisense molecule is Sof. Sof is an antisense antidote for the chromosomally encoded toxin called gef (Poulsen, L., et al., 1991, Mol. Microbiology 5:1639-48). Sof normally acts to regulate the levels of gef in the bacterium. The inventors of the present invention have designed sense molecules which are complementary to Sof. The sense molecules against Sof act to inhibit the ability of Sof to regulate gef, and thus cause toxicity in the pathogen by allowing the endogenous gef levels to become toxic.

Ribozyme Targets

For ribozymes to be effective anti-microbial therapy, it is preferable to target the RNA of, for example, several key proteins, tRNA, rRNA or any other RNA molecule essential for cell viability or fitness, in order to insure complete inactivation and prevent escape of the invading microorganism.

The complexity of human RNA is about 100 fold lower than that for human DNA, and specificity can be achieved with as few as 12-15 base pairs. The stability of the RNA-RNA duplex is effected by several factors, such as GC content, temperature, pH, ionic concentration, and structure. The nearest neighbor rules can provide a useful estimate of the stability of the duplex (Castanotto et al. "Antisense Catalytic RNAs as Therapeutic Agents" *Advances in Pharmacol.* 25:289-317, 1994).

The catalytic ribozyme of the invention also includes a catalytic sequence, which cleaves the target RNA near the middle of the site to which the target RNA-specific sequences bind. In the hammerhead-type of ribozyme, the catalytic sequence is generally highly conserved. The conserved catalytic core residues are 5' CUGANGA 3' and 5' GAAA3' linked by an evolutionarily conserved stem-loop structure.

The most conserved and probably most efficiently cleaved sequence on the target RNA is 5' GUC 3'. However, NUX (wherein X=A, U or C) can also be cleaved efficiently. Such cleavage sites are ubiquitous in most RNAs allowing essentially all RNA's to be targeted (Whitton, J. Lindsay "Antisence Treatment of Viral Infection" *Adv. in Virus Res.* Vol. 44, 1994).

With regard to the selection of the appropriate sites on target RNA, it is known that target site secondary structure can have an effect on cleavage in vitro (Whitton, 1994 supra). A number of procedures are available to select accessible sites in RNA targets. In a preferred procedure, a library screen may be employed to select appropriate sites on the target RNA. Accessibility of the selected site may then be confirmed using techniques known to those skilled in the art. Thus, the selected target molecule's sequence can be routinely screened for potential secondary structure, using the program RNAFOLD (from the PCGENE group of programs or available on the Internet). Thus, reasonable predictions of target accessibility can be made. Computer assisted RNA folding (Castanotto et al., 1994), along with computational analysis for 3-dimensional modeling of RNA (Major et al., *Science* 253:1255-1260, 1991 and Castanotto et al., 1994) is certainly effective in guiding the choice of cleavage sites.

The nucleic acid, wherein at least one trans-acting ribozyme is targeted to a ccdA, kis, pemI, parD, phd, higA, chpAI, chpBI, kicA, soc, sos, srnC, flmB, pndB, sof, korA, korB, korC, korD, korE, or korF transcript of the pathogen is provided. The nucleic acid, wherein at least one trans-acting ribozyme is targeted to the rpoA transcript of the pathogen is provided. The nucleic acid, wherein at least one trans-acting ribozyme is targeted to the secA transcript of the pathogen is provided. The nucleic acid, wherein at least one transacting ribozyme is directed to the dnaG transcript of the pathogen is provided. The nucleic acid, wherein at least one trans-acting ribozyme is directed to the ftsZ transcript of the pathogen is provided. A nucleic acid encoding a multi-ribozyme can encode all or some of the above trans-acting ribozymes. The ribozymes can all be under the control of a single promoter.

For example, several bacterial genes, essential for viability and unrelated in activity, have been selected and are described herein to highlight how the selection of appropriate mRNA targets is carried out for the preferred construction of the antimicrobial agent against prokaryotic targets. Cross-genera RNA targets can be used to design an antimicrobial that can have broad application, modified by the specificity of the promoter. In addition, several toxic agents are described herein to highlight how the selection of appropriate toxic agents is carried out for the preferred construction of the antimicrobial agent against prokaryotic targets.

In one embodiment of the invention, the first ribozyme targets an essential transcription factor, the second ribozyme targets an essential general secretory component, the third ribozyme targets an essential component of the primosome required for DNA biosynthesis and the fourth ribozyme targets an enzyme required for cell division. Consequently, the ribozymes are redundant in the fact that they inhibit growth by specifically targeting a fundamental process required for bacterial growth. Thus, this can minimize the development of resistance to the antimicrobial therapeutic.

For example, one target is the essential protein, rpoA or the alpha subunit of RNA core polymerase. rpoA was selected rather than the other components of the RNA polymerase holoenzyme, because it is thought to facilitate the assembly of an active RNA polymerase enzyme complex. Inactivation of the rpoA transcript results in a decrease in the intracellular concentration of the holoenzyme RNA polymerase rendering the cell less able to respond to changes demanded of it once it has invaded a new host. The nucleotide sequence of rpoA is known for a large number of microorganisms (>20 genera) and they are readily available from GenBank.

A second example of a ribozyme target can be the mRNA of the secA gene from bacteria. The product of this gene is the essential and rate-limiting component of the general secretory pathway in bacteria (Bassford et al., 1994, Nucleic Acids Research Apr. 11, 22(7):1326; Nucleic Acid Research. 22(3): 293-300). SecA has been found in every prokaryotic cell investigated to date. Additionally, its biosynthesis is translationally coupled to the upstream gene, X (Schmidt et al., 1991, J. Bacteriol. 173(20):6605-11), presenting a convenient target for a ribozyme. Inhibition or decreased synthesis of secA is also sufficient to confer a reduction in viability to the cell (Schmidt et al., 1987, J. Bacteriol. 171(2):643-9). Furthermore, as a pathogen responds to changes required of the infectious process a change in the availability of a key protein such as secA will disadvantage the pathogen enabling the host to counteract it. Finally, control over the secretion-responsive expression of secA is at the level of translation (Christoffersen et al., 1995, J. Med. Chem. 38(12):2023-37), and the regulatory sequences within its polycistronic message have been localized to a region comprised of the end of the upstream gene, X, and the beginning of secA. Consequently, inactivation of the transcript by the catalytic cleavage of a ribozyme has profound consequences for the viability of the invading microorganism.

The third ribozyme can target essential factor for DNA biosynthesis, such as DnaG. Every 1 to 2 seconds, at least 1,000 times for each replication fork within *E. coli*, priming of an Okazaki fragment is repeated as a result of an interaction between the cellular primase dnaG (Bouche et al., 1975, J. Biol. Chem. 250:5995-6001) and dnaB (Marians, K. J. 1996, Replication Fork Propagation, p. 749-763. In F. C. Neidhardt (ed.), *Escherichia coli* and *Salmonella*: Cellular and Molecular Biology, 2nd ed, vol. 1. American Society for Microbiology, Washington, D.C.). As would be expected of a protein required every 1 to 2 seconds during replication, a lesion within DnaG or an alteration in its concentration results in an immediate stop phenotype (Marians, K. J. 1996, Replication Fork Propagation, p. 749-763. In F. C. Neidhardt (ed.), *Escherichia coli* and *Salmonella*: Cellular and Molecular Biology, 2nd ed, vol. 1. American Society for Microbiology, Washington, D.C.); Weschler et al., 1971, Mol. Gen. Genet. 113:273-284). Therefore, inactivation of the DnaG message by a ribozyme should have profound cellular consequences in that general priming of the lagging strand is reduced if not eliminated. DnaG is a component of the primosome, a multi-protein complex responsible for priming replication. Any of the components of the primosome, either individually or in any combination, can serve as a target for inactivation of the primosome and, thus, kill the cell. The other components of the primosome are DnaB, DnaC, DnaT, PriA, PriB, and PriC. Thus, the primosome is also sufficiently complex to provide numerous other targets (DnaB, DnaC, DnaT, PriA, PriB and PriC) for inactivation by the trans-acting ribozyme.

A fourth target can be ftsZ. This gene also encodes an essential protein, ftsZ, that is required for cell division in that it is responsible for the initiation of separation. ftsZ was selected because cleavage of the ftsZ RNA leads to inhibition of cell division and a reduction in viability. Any toxic agent or ribozyme which targets ftsZ (such as DicF1) may be used to inhibit division of a cell requiring the ftsZ gene product. Also, for example, upon cleavage of the ftsZ message by a ribozyme, such ribozyme can attack additional copies of the ftsZ message inhibiting the division of the cell. The nucleotide sequence of ftsZ like the other targets selected, is commonly available from GenBank.

It should be clear that any other essential protein of a pathogen can have its message targeted in the present invention, and that determining which proteins are essential can be routinely determined according to standard protocols in the art. In fact, there are over 52,000 viral, 41,000 bacterial and 12,300 fungal sequences deposited in the public section of the Entrez Database at the National Center for Biotechnology Information. Any of these can be used to design the catalytic trans-acting ribozyme of the invention.

In addition to targeting mRNA of essential proteins, ribozymes may be targeted against other RNA species within the cell. Specifically, appropriate targets in bacteria, fungi and other lower eukarytoes include ribosomal RNA such as Small Subunit RNAs (SSU) or Large Subunit (LSU) and tRNA molecules required for protein synthesis. With respect to pathogenic *Staphlococus*, the RNA III moiety in a relatively low abundance transcript which is not translated and should be accessible for cleavage. As long as the RNA targeted contains a canonical ribozyme cleavage domain, the ribozyme therapeutic can hybridize and cleave the complementary RNA, thus impacting the fitness of the microbial cell. Additionally, over 3000 rRNA species have been sequenced and aligned. This information is available from the Ribosomal Database Project and should facilitate rapid design and adaptation of ribozyme(s) against such targets. For example the 16S rRNA molecule of bacteria is especially attractive in that there are over 4000 copies of the 16S rRNA per cell. Consequently, a reduction in number slows the process of protein synthesis in so far as the 16S rRNA molecule is involved in the process of translational initiation. Thus, a toxic agent or ribozyme directed against mRNA and rRNA impacts the fitness of the offending microorganism.

5.8. Protection of Toxic Agent and/or Ribozyme Producing Cells

The nucleic acids coding for the toxic agents or ribozymes can be toxic to the cells that are needed to produce the toxic agent or ribozyme-carrying virions. When using a broad host-range virus like P1, the organism used to produce the virion can be different from the target organism. In this way, the producing strain is resistant to the toxic effects of the toxic agents or ribozymes because they are not efficiently expressed in the producing strain, due to species-specific promoter elements, and the ribozymes will not have any target RNA molecules to attack, due to the species-specific sequences that target the ribozymes. When using a species-specific virus that must be expressed and assembled within a strain of the targeted microorganism, this toxicity becomes a significant concern. The assembly of a virion consisting of anti-*E. coli* ribozyme or toxic agent genes packaged in lambda will illustrate the approach used to circumvent the toxicity. For example, the ribozymes directed against RNA species of *E. coli* is expressed from an artificial promoter containing consensus promoter elements. This promoter provides high level transcription of the ribozyme immediately upon infection of targeted cells. In order to prevent the unwanted death of the producing strain of *E. coli*, transcription is repressed in the producing strain by a mechanism not available to the wildtype strains that are targeted for killing. Sequences constituting the DNA binding sites for a heterologous transcription factor are interspersed between the essential activating elements of the ribozyme promoter. Expression of the heterologous transcription factor in the producing strain results in the occlusion of the activating promoter elements and preventing the binding of RNA polymerase. As an example, the gene for the *Saccharomyces cerevisiae* transcription factor Ste12p may be expressed in *E. coli* and bind to its binding sites, the pheromone response element, located within the ribozyme promoter. Ste12p will not be found in wild strains of *E. coli*; therefore, the ribozyme promoter will be accessible to RNA polymerase following delivery of the plasmid to the targeted cells.

An alternative strategy that can protect the producing strain from the toxicity of the ribozymes employs ribozyme-resistant versions of the targeted RNA molecules. This strategy can be used when the target RNA molecule codes for a protein. The ribozyme target site within the mRNA molecule is mutated by site-directed mutagenesis such that the amino acid sequence of the translated protein does not change but the mRNA sequence no longer serves as a substrate for the ribozyme. For example, hammerhead ribozymes require an NUX sequence within the target mRNA for cleavage to occur. By changing this sequence to something else, the ribozyme will not cleave the mRNA. This type of ribozyme resistant version of the target RNA can be expressed from a plasmid or integrated into the chromosome of the producing strain and thus render this strain resistant to the toxic effects of the ribozyme.

Another strategy that can protect the producing cell from the toxicity of a toxic agent employs co-expression of a neutralizing agent or antidote. Such co-expression of an antidote or neutralization agent protects the packaging cell from the toxic effects of the encoded toxic agent. Such a strategy is particularly useful is the promoter used to express the toxic agent is leaky, and leads to expression of the toxic agent in the producing cell. For example, a packaging strain (e.g., bacteria cell) may used to package the a viral vector containing a toxic agent into a bacteriophage phage head. Survival of the packaging cell or optimization of the quantities of vector or phage made by the producing cell may require co-expression of an antidote or neutralization agent in the producing cell. A neutralization agent is any molecule (such as protein, antisense, sense, or other molecule (such as a drug, chemical, etc.)) which counteracts the toxic effects of a toxic agent. By way of illustration, in a specific example, the packaging strain cells contain a bacteriophage P1 plasmid as well as the Transfer plasmid comprising the toxic agent doc and a ribosome entry site. In the case that the Transfer plasmid is determined to be toxic to the packaging strain, a third plasmid may be introduced, which encodes an antidote to doc, such as the phd protein. The additional plasmid with the antidote acts to protect the packaging strain against the toxicity of doc.

The improvement in the present invention is that a non-replicative delivery system has an advantage in that once the phage coat has injected the nucleic acid into the targeted bacterium, the expression of the toxic agent or ribozyme will destroy the microbe, as opposed to a lytic infection cycle typical of an intact bacteriophage. Consequently, amplification of the phage coat will not be an issue and it is less likely that the non-replicative phage delivery system will generate an immune response such that subsequent use of the delivery system would be jeopardized. Moreover, if the patient has been exposed to a resistant pathogenic microbe and the therapeutic of the invention is effective and neutralizes the invading microbe, then it is expected that the microbial antigens liberated as a result of the action of the therapeutic, will illicit sufficient humoral immunity and cell-mediated immunity to confer protection against subsequent attacks.

5.9. Therapeutics & Pharmaceutical Preparations/Formulations and Methods for Administration The present invention further encompasses the use of a toxic agent and/or ribozymes of the present invention for the treatment of disease, viral infection, parasitic infection and microbial infection. The present invention further provides a method of treating a subject having a proliferative disease of a specific tissue by inhibiting cell proliferation in the tissue, comprising administering to the subject a toxic agent and/or ribozyme operably linked to a tissue-specific promoter sequence, which promoter is specific for the diseased tissue, and whereby the ribozyme and/or toxic agent encoded by the nucleic acid is expressed, cell proliferation is inhibited, and the proliferative disease is treated.

The present invention further provides a method of treating a subject having a pathogenic infection or disease, by inhibiting replication of the pathogen, comprising administering to the subject a toxic agent and/or ribozyme operably linked to a pathogen-specific promoter, whereby the ribozyme and/or toxic agent encoded by the nucleic acid is expressed, the pathogen is inhibited from replicating or is killed or rendered less fit, and the infection or disease is treated. The present invention encompasses the toxic agent(s) and/or ribozyme(s) of the present invention in pharmaceutical formulations.

In several embodiments of the invention, toxic agents or ribozymes of the invention are particularly suited as antimicrobial therapeutics. For example, upon nucleic acid hybridization with the target RNA transcript, a ribozyme-RNA complex achieves a catalytic form that acts as a nuclease to cleave the targeted RNAs. Thus, cleavage deprives the invading microorganism of essential cellular processes which then kills or renders it less fit. Additionally, a toxic agent of the invention may also be used as an antimicrobial therapeutic. A toxic agent may be used alone, or in combination with one or more other toxic agents. Thus, delivery of a toxic agent to an invading microorganism, kills or render it less fit. A toxic agent may also be used in combination with one or more ribozymes. Further, a combination of ribozymes and toxic agents may be used as an antimicrobial therapeutic.

The invention provides use of one or more ribozymes and/or toxic agents directed towards essential, housekeeping, or virulence genes of one or a series of candidate microorganisms. Inactivation of essential proteins and virulence determinants render the invading microbes inactive or slow their growth, while at the same time, the essential processes of the host are not significantly affected.

A method of delivering a toxic agent or ribozyme to a target (e.g., a pathogen) in a subject is provided, comprising a) generating a liposome comprising a promoter and a sequence encoding a toxic agent or ribozyme; and b) delivering the liposome to the subject, whereby the target-specific promoter directs transcription of the toxic agent or ribozyme in the cells of the target. The target can be a pathogen, for example, a bacteria, fungus, yeast, parasite, virus or non-viral pathogen.

A method of targeted delivery of a toxic agent or ribozyme to a pathogen in a subject is provided, comprising a) generating a virion comprising non-viral DNA of the invention; b) combining it with a liposome; and b) delivering the liposome containing the virion to the subject, whereby liposome enters the eukaryotic cell and releases the virion, which delivers the DNA to the pathogen, whereby the pathogen-specific promoter directs transcription of the toxic agent or ribozyme in the cells of the pathogen.

A method of treating an infection in a subject is provided, comprising administering to the subject the liposome comprising DNA comprising a target-specific promoter and a sequence encoding a toxic agent or ribozyme, whereby the toxic agent or ribozyme encoded by the DNA is expressed and the infectious agent is killed or weakened. The liposome used in this method can comprise any ribozyme-encoding nucleic acid, or any toxic agent-encoding nucleic acid, particularly those described herein targeted to genes of the pathogen. The infection can be bacterial, fungal, yeast, parasitic, viral or non-viral.

Parenteral administration, if used, is generally characterized by injection (intravenous, intradermal, subcutaneous and intramuscular). Injectables can be prepared in conventional forms, either as liquid solutions or suspensions, solid forms suitable for solution of or suspension in liquid prior to injection, or as emulsions. A more recently revised approach for parenteral administration involves use of a slow release or sustained release system such that a constant level of dosage is maintained. See, e.g., U.S. Pat. No. 3,610,795, which is incorporated by reference herein. In certain preferred embodiments of the invention administration is parenteral.

The present invention relates to prophylactic administration. For example, many hospital patients or immunocompromised hosts are particularly susceptible to pathogenic infections. Further, many hospital strains of pathogens are resistant to traditional antibiotic treatment, such as Penicillin. The therapeutics of the invention are particularly useful for preventing pathogenic infection or treating infections caused by resistant strains of pathogens.

Suitable carriers for parenteral administration of the substance in a sterile solution or suspension can include sterile saline that can contain additives, such as ethyl oleate or isopropyl myristate, and can be injected, for example, intravenously, as well as into subcutaneous or intramuscular tissues.

Topical administration can be by creams, gels, suppositories, aerosols, sprays, and the like. Ex vivo (extracorporeal)

delivery can be as typically used in other contexts. In certain preferred embodiments of the invention administration is an aerosol. In other preferred embodiments of the invention, administration is as a topical treatment. In one embodiment of the invention, treatment of infections associated with burns or open wounds, topical administration may be preferred.

Oral administration is also provided. Suitable carriers for oral administration include one or more substances which can also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers can be water, pyrogen free saline, pharmaceutically accepted oils, or a mixture of any of these. The liquid can also contain other suitable pharmaceutical additions such as buffers, preservatives, flavoring agents, viscosity or osmo-regulators, stabilizers or suspending agents. Examples of suitable liquid carriers include water with or without various additives, including carboxypolymethylene as a pH-regulated gel.

The therapeutic of the invention can be administered to the subject in amounts sufficient to produce an antibiotic effect or to inhibit or reduce the activity of the target pathogen. Optimal dosages used will vary according to the individual, on the basis of age, size, weight, condition, etc, as well as the particular modulating effect being induced. One skilled in the art will realize that dosages are best optimized by the practicing physician and methods determining dosage are described, for example, in Remington's Pharmaceutical Sciences [Martin, E. W. (ed.) Remington's Pharmaceutical Sciences, latest edition Mack Publishing Co., Easton, Pa.]. Treatment can be at intervals and can be continued for an indefinite period of time, as indicated by monitoring of the signs, symptoms and clinical parameters associated with a particular infection. The parameters associated with infection are well known for many pathogens and can be routinely assessed during the course treatment.

6. Example: Construction & Characterization of Promoters

Classical bacterial inducible promoters are renowned for their inability to tightly control transcription, and a significant level of background expression is characteristically observed.

The Leashi Promoter

The present invention provides bacterial promoters that allow for tight regulation of transcription and enhanced expression. A novel promoter called LEASHI has been constructed from three elements (see FIG. 1A). The first element, termed RIP was a combination of two consensus sites at −10(TATAAT) and −35(TTGACA) located with respect to transcription initiation. The second element was based on the lacI repressor binding sequence (termed lac operator sequence) which was placed between the −10 and −35 consensus sites. Placement of the lac operator between the −10 and −35 sites, more effectively blocked RNA polymerase binding to the promoter, thus enhancing transcriptional control from the promoter. The promoter was designed such that it was 'switched on' following the addition of isopropyl B-D-thiogalacto pyranoside, which binds and subsequently titrates out the repressor protein. RNA polymerase can then bind to the promoter and transcription can proceed.

The third element of the LEASHI promoter was the UP element. The UP element was an adenine/thymine rich sequence which was placed immediately upstream of the −35 element. Addition of the UP element, further increased expression from this promoter.

The LEASHI promoter sequence: (SEQ ID NO:1)

```
5' GATCCTCAGAAAATTATTTTAAATTTCCAATTGACATTGTGAGCGGA
TAACAATATAATGTGTGGA3'
```

A significant advantage of the LEASHI promoter of the present invention is that it alleviates the high levels of background commonly observed in inducible promoters. A limiting factor leading to high background levels of transcription when a promoter of interest is located on a high-copy number plasmid, is due to the lack of repressor molecules available to bind to the promoters. The present invention overcomes this problem by using a lacI expression plasmid and secondly, by placement of the lac operator between the −35 and −10 consensus elements which more effectively blocks transcription during normal conditions. Furthermore, the UP element placed immediately upstream of the −35 region enhanced transcription from the promoter.

The LEASH1 promoter (FIG. 1B) was designed as a lacI-regulated promoter which a broad spectrum promoter activity in a wide variety of bacteria. The IPTG inducible LEASH1 functions in *Escherichia coli* and is tightly regulated. It is active in both Gram-negative and Gram-positive bacteria.

As described herein, ribozymes of the invention have been operably linked to the LEASHI promoter. In another specific embodiment of the invention, a toxic agent of the invention was operably linked to a LEASHI promoter.

The Modified rrnb Promoter

A novel promoter called the modified rrnB has been constructed (see FIG. 1C). Modified rrnB promoter sequence: (SEQ ID NO:2)

```
5'AGAAAGCAAAAATAAATGCTTGACACTGTAGCGGGAAGGCGTATAATG
GAATTGTGAGCGGATAACAATTCACA 3'
```

The Anr, Arc, and Proc Promoters

The Anr (FIG. 1D), proC (FIG. 1E) and Arc (FIG. 1F) promoters are species-specific. Both anr and proC are transcriptionally off in *E. coli* and on in *Pseudomonas aeruginosa*. These promoters provide the advantage of allowing controlled expression of the toxic agents in the pathogen (*Pseudomonas*), while allowing the packaging strain (*E. coli*) to be protected from the toxic actions of the therapeutic. Such promoters are particularly useful to facilitate manufacturing of the delivery vehicle. Such promoters also enable bacterial specific targeting of the gene therapeutic in the patient. *Pseudomonas aeruginosa* 'specific' promoters (5' to 3')

```
ANR promoter
5' ACTCGCGGATCATCTTCACCATCGGCCGCAACT (SEQ ID NO: 3)
CCTGCGGGATATCCTCGTCCTCCTCCTCCACCGGCA
CCCCCATGGTAGCGGCCAGCTCGCGCCCTGCCTGGG
AAAGCTGTACATGCTGATCGGCGGCGTCGGTGCCGG
CGGCCGGGTCTTCCGCCTGCTCGGCGGTGCCGGTCC
GTGCGGCCTTGGCGTCCGCGGCGGCGCGCGATGAGG
GCGGCACCTGGGTGGTGATCCAGCCACTGAGGGTCA
ACATTCCAGTCACTCCGGGAAAAATGGAATTCTTCC
ATTGGATCGGCCCACGCGTCGCGAACTTGAGCCCCC
```

-continued

```
TTTTCGTCGCCCCTTGACAGGGTGCGACAGGTAGTC

GCAGTTGTTTGACGCAAGTCACTGATTGGAAACGCC

ATCGGCCTGTCAGAAATGGTCGTTGCCAGACCTATG

GCTGGCACCCGCATCGCGGCTGCGTTACCCTTACTC

CTGTTGTGCCTTTAACCTAGCAAGGAC
```

ProC promoter
5' AATTCCTCGAAGTCCTTGCGCTGCTTGTCGTTC (SEQ ID NO: 4)

```
ATGATGTCGTAGATCAGCGCATGCACCTGCTTGTGT

TCCAGCGGTGGCAGGTTGATCCGGCGTACATCGCCA

TCCACCCGGATCATGGGTGGCAGGCCGGCGGAGAGG

TGCAGGTCCGAAGCGCCCTGTTTGGCACTGAAGGCG

AGCAGCTCGGTAATATCCATGGGACTCCCCAATTAC

AAGCAAGCAGGTAGAATGCCGCCAAAGCCGCCGTCT

CGGACAAGGAAAACACCGGATGAGCCAGGGTGCTTC

CAGGACACGCGTGGTGTCCTGCGCCAGACGCGGAAC

CTCGACACTGGAACAGGAAGATGGCCATCGAGGCCG

GCGGTTTCGAGGGCGTCGAGCCGACGCCGACCGCAC

TTCCATAGGGCGCAGGTAATGTCCACGATAGCAGAG

AATATTGCAAAGGTTGCCGCGCGCATCCGTGAGGCA

GCGCAAGCTGCGGGGCGCGATCCGGCCACGGTCGGC

CTGCTCGCCGTGAGCAAGACCAAGCCCGCCGCCGCG

GTGCGCGAGGCGCACGCCGCCGGCCTTCGCGACTTC

GGCGAAAACTACCTGCAGGAGGCCCTCGGCAAGCAG

GCCGAACTGGCCGACCTGCCCTTGAACTGGCACTTC

ATCGGCCCCATCCAGTCGAACAAGACGCGGCCCATC

GCCGAGCATTTCCAGTGGGTGCACTCGGTGGACCGG

TTGAAGATCGCGCAGCGCCTGTCGGAGCAACGCCCG

GCCGGGCTGCCGCCCCTGAATGTCTGCCTGCAGGTC

AACGTCAGCGGCGAAGCCAGCAAGTCCGGCTGCGCC

CCCGAGGACCTGCCGGCCCTGGCCGAGGCCGTGAAG

CAACTGCCCAACCTCCGATTGCGTGGCCTGATGGCC

ATCCCCGAACCCACCGCCGAACGCGCCGCGCAACAC

GCCGCGTTCGCCCGCCTGCGCGAACTGCTGCTGGAC

CTGAACCTTGGCCTGGACACCCTGTCCATGGGCATG

AGCGACGACCTCGAGGCAGCCATCGGCGAAGGTGCG

ACCTGGGTCCGCATCGGTACCGCCCTGTTCGGCGCC

CGCGACTACGGCGCGCCGGCTTCTTGAATGAATCCC
```

ARC promoter
5' CTA GAG CTA TTG ATG TGG ATC AAC (SEQ ID NO: 5)

ATT GTC CAC TAG CCG CTG CCG CCT AAT

CTC CAG AAT TGT GAG

Anr, Arc, and proC promoters, which were expressed preferentially in *P. aeruginosa*, have been isolated and shown to express a toxic agent specifically in this pathogenic bacterium (See Tables 1 and 2 and FIG. 2). Specifically, as shown in Table 1, promoters were cloned upstream of the β-lactamase reporter gene in a cassette flanked by multiple transcription terminators. Constructs were transformed into *E. coli* or *P. aeruginosa* and plated onto agar containing different amounts of carbenicillin. Three repeat evaluations gave the same result.

TABLE 1

Evaluation of Promoters Utilizing β-Lactamase as a Reporter Gene

| | E. coli | | P. aeruginosa |
|---|---|---|---|
| Construct | 25 µg/ml carbenicillin | 50 µg/ml Kanamycin | 5 mg/ml carbenicillin |
| empty vector (no promoter) | − | + | − |
| UPRIP β-lactamase | + | + | + |
| proC β-lactamase | − | + | + |
| anr β-lactamase | − | + | + |

As shown in Table 2, the chpBK gene was cloned in both orientations under the control of *P. aeruginosa* promoters proC and anr. Equal quantities of DNA (500 ng) were transformed into *E. coli* and *P. aeruginosa* and plated on agar. Mock transformations were also performed with 'no DNA'. + indicates greater than 100 colonies, − indicates no detectable colonies. Parentheses indicate orientation of the chpBK gene in relation to the promoter. Experiments were repeated at least two times with the same result. Importantly, plasmids using proC and anr to regulate chpBK expression did not induce cell death in *E. coli* indicating lack of transcriptional activation function.

TABLE 2

Evaluation of Promoters that are Expressed Preferentially in *P. aeruginosa*

| Construct | E. coli | P. aeruginosa |
|---|---|---|
| patent vector | + | + |
| anr chpBK (positive) | + | − |
| anr chpBK (negative) | + | + |
| proC chpBK (positive) | + | − |
| proC chpBK (negative) | + | + |

The development of species-specific promoters is particularly important in aspects of the invention in which it is desired to allow indigenous commensal bacteria to be protected from the toxic agents of the invention while targeting the pathogenic *P. aeruginosa*.

TSST-1 Promoter

The environmentally regulated *staphylococcus*-specific promoter TSST-1 has been obtained and a transfer plasmid utilizing this promoter is used to express doc or other toxic agents. A *staphylococcus* specific phage capable of delivering the transfer plasmid into *S. aureus* strains is used to specifically target the Staphylococcal pathogen.

TSST-I promoter (SEQ ID NO:6) (GenBank accession number U93688, see also Lindsay, J. A., et al., 1998, "The gene for toxic shock toxin is carried by a family of mobile pathogenicity islands in *Staphylococcus aureus*" Mol. Microbiol. 29 (2), 527-543):

```
   1 ttatttagca ggaataatta gccagattat cgagggagtt ccagggcaatccaaacattg
  61 ttatatatgc atttataaaa ttttcaagat aatttattat tcatacccttgccctttgtt
 121 tcaaaattat gcccttttt tgcccttgga aacaaccaca ctcctaaattaataggtggt
 181 gtggtttgat catttataat ataacataaa aacaaccacc cagtaactagtatgagtggc
 241 gtagcgacta taacaactct atgttatcaa gatatatgta tatgagtgatgacaaggaag
 301 atgtctcctg tgagaccaac agccagatat atggcctctt gccgggctatatagttcact
 361 cctactatat acacatgtaa ttataacata aaaaaataga caagtaccgaagtacctgcc
 421 taaataacaa caagattaac atgtgaataa tggaaataaa aagtcagcccgaaggctaac
 481 ttacgaatag atgaaaattt gaacacattg ctgtgtctaa aatgattatagcataaataa
 541 cgaatatttc cagctcgaaa ttaatatatt gtaataataa tattttatatctttgttaat
 601 aattatttaa ttgatttaca taaataataa ttgtaaaatt aatttgtaatcgattgcaaa
 661 taagttatag gagaaaataa aatgaataaa aaactattaa caaaaacattgatagcaagt
 721 gctttagttt taacaacagt aggttcaggt tttcattctt cttcaaattataatggtatt
 781 aataacgttg aaaaagctga gcaaacgaca gataacgcat tgtggaaaaatgtaagagac
 841 gctttaaaag acgcgaatat tatcgataaa acagataatg aaaatgtcaaggttacgtat
 901 aaaatagaaa atggtggaga aaataccata gaaggaacag ttaatttagaaaatattagt
 961 acttcaaaca atcctaaaat aaaccctcaa aatgttacaa aaattaatataactagaaaa
1021 aatccgaact accctaatat tgatgctaat aatacatgga aaaaattaccagaaaaattg
1081 aaagaaaaaa atatagtgga acaacggcga caatgtttca atcttaagtacagaccctaa
1141 agatgagact gtattcggta aagtaggaga agataaatca aacgtaagcaatagatacat
1201 caatcctaaa gatataaatg aattcaaatc actaaaaata cttttttccgaggcagatta
1261 ctcctgcctc tttctttgaa cagtgatatc ttctgatcta tgtaacactcaattacttca
1321 gattctttac ctttaacttc ctttaattca tttctctcta tctcctcaaaaagttgtgct
1381 ttttgatttg tgattggagt tgggcgtttt ttcatcgcgt tgtttcaattccttttaag
1441 gtattctaat tctcttctag tcatatcaat tgttttttta cttctcacctttagtgaaat
1501 actcttatcc tttctcttct tgcgttaatg ttgctaatta gtataaaatacatgcgccca
1561 tatattccaa tggtaggaca tttaattctg gattttcagc tattttcataaatctattat
1621 ctgataattt gcttaatcca attttcaagc catagcctaa attccccatccactaagtca
1681 ttttgtttca tatggttta atctacggcc aatctcaaag atagattgaccagcgatgtt
1741 taaagtcata tttcacggat ccacatttac gataaacata tctagttacacaatattatc
1801 ccttactgca acacaggacg tttctcagcg taaaaaacac cactagaaagtgactttaaa
1861 gaatataact aattcaaact tatattaatt aatattcttt aaatgaccactcacactttg
1921 ttttttgcta tttgtaactt taaaatgttg tttgaaatct atattttttgatatagctc
1981 cctatgtaac aaacaatttt taattaatat atatttaaac aagtcaatttagagatcggt
2041 taattcgatt catttaaata atatttatac attctatatg taaacgtttacacatttgaa
2101 gtaaggagaa ttaaaaatga
```

7. Example: Effects of Toxic Agents on Bacterial Growth

In order to demonstrate the methods of the invention, the inventors have expressed and targeted several toxic agents to bacterial pathogens. Toxic agents were selected based on their ability to inhibit the growth of a pathogen or diseased cell or cause lethality in a pathogen or diseased cell. The examples hereinbelow illustrate toxic agents of several naturally occurring phage, plasmid and chromosomally encoded toxic proteins and demonstrated their effectiveness as antimicrobial therapeutic agents.

Specifically, several naturally occurring phage, plasmid and chromosomally encoded toxic proteins have been identified and have demonstrated effective as antimicrobial therapeutic agents, including but not limited to SecA, 16S RNA, dicF, sof, dicF antisense, 16S antisense, toxic proteins of the toxin/antidote pairs doc/Phd, gef/Sof, chpBK/ChpB1, or kicB/KicA.

To illustrate that a toxic agent may be a toxic gene product of an addiction system toxin, a toxic gene product of a chromosomally endcoded toxin, or antisense molecule, nucleic acids encoding doc, gef, chpBK, kicB or DicF1 were engineered into Transfer plasmids for use in the P1 bacteriophage delivery system. Plasmid construction was performed by standard methods known in the art.

As shown in FIG. 3, expression vectors for the cloning of Toxic agents were engineered. Specifically, genes encoding the toxic proteins chpBK, kicB, doc and gef under the control of the lacI-regulated promoter, were cloned into an E. coli vector containing replication origin ColE1 (300-500 copies per cell), pMB1 (15-20 copies per cell) or p15A (10-12 copies per cell) and the selectable marker cat., chloramphenicol or bla, ampicillin. Toxic agents were cloned in an E. coli strain that overexpressed the lacI repressor protein from a lacI expression plasmid. Genes encoding the toxic proteins chpBK, kicB, doc and gef under the control of lacI-regulated promoter, were obtained by PCR and cloned into an E. coli shuttle vector. Lethal agents were cloned in an E. coli strain that overexpressed the lacI repressor protein form a lacI expression plasmid.

Plasmids containing the toxic agents doc or gef were also been engineered such that a ribosome entry site has been constructed upstream of the nucleic acids encoding the toxic agent in order to increase the levels of translation of doc or gef. Plasmids harboring a toxic agent was called a Transfer plasmid. The Transfer plasmid was constructed such that it contained 1) an origin of replication 2) selectable marker 3) P1 PAC site, and PAC ABC genes 4) P1 lytic replicon 5) nucleic acids encoding the toxic agent (e.g., doc, gef, or DicF1).

Specifically, Transfer plasmids were constructed based on pBluescript (ColE1 origin) and pBBR 122 (broad host range origin) parent vectors. The nucleic acids encoding the toxic agents doc or gef were cloned into the broad host range transfer plasmid. The nucleic acid encoding dicF was cloned into the ColE1 transfer plasmid. The structure of each vector is available. Both doc and gef were placed under lacI regulated promoter. The Transfer plasmids were designed to undergo rolling circle replication during the phage lytic cycle.

A packaging strain (e.g., bacteria cell) was then used to package the Transfer plasmid containing the nucleic acid encoding the toxic agent into a bacteriophage phage head. The packaging strain for each of the three toxic agents contained the P1 bacteriophage prophage as well as the Transfer plasmid containing the nucleic acids encoding the toxic agent. In some cases, the packaging strain also contained a third plasmid, if necessary, which encoded additional antidote protein which acted to protect the packaging strain against the toxicity of the toxic agent or the third plasmid encoded additional repressor protein to switch off the promoter of the Transfer plasmid.

Thus, the packaging strain (P1 lysogen) was used to package the transfer plasmid containing the toxic agent (e.g., doc, gef, or DicF1) into phage heads or virions. Phage lysates of the packaging strain contained the infectious bacteriophage virions, and were used to infect bacterial targets in the following manner.

The P1 lysogen (P1cm C1.100) carrying the transfer plasmid with the toxic agent (doc or gef or DicF1) was grown at 30° C. in LB, 10 mM MgSO$_4$, 5 mM CaCl$_2$, 12.5 µ/ml chloramphenicol unit A$_{450}$ reached 0.8 at which time the culture was shifted to a 42° C. water bath and aerated vigorously for 1 h. Chloroform was added and incubation continued for an additional 20 min at 37° C. The phage stock was clarified by centrifugation at 4,000 g for 20 min. DNase (1 µg/ml) and RNase (10 µg/ml) were added and after incubation at 37° C. 30 min the phage were centrifuged at 4,000 g 20 min. Phage particles were precipitated from the phage stocks by adding NaCl to 1 M and polyethylene glycol 6000 to 10% (w/v). After incubation on ice for 2 h the phage were pelleted by centrifugation at 11,000 g for 15 min. The pellet was carefully dissolved in 50 mM Tris.Cl pH 7.5, 10 mM MgSO$_4$, 5 mM CaCl$_2$, 0.01% Gelatin. Polyethylene glycol was removed by extraction's with chloroform.

The phage lysates were then used to infect a selected pathogen (e.g., E. coli). Target cells (10$^5$ CFU/ml, treated with 10 mM MgSO$_4$, 5 mM CaCl$_2$) were infected at various M.O.I s (0.1, 1, 10, 100) with each of the above phage lysate. Following 30 min infection at 30° C. Cell death was assessed by scoring the plates for the total number of colony forming units.

Both types of Transfer plasmids (ColE1 and broad host range based) were transferred by the P1 delivery system to various E. coli strains in vitro. The P1 system was also used to deliver the broad host range transfer plasmid to P. aerugincsa in vitro. The ColE1 transfer plasmid was successfully transferred to E. coli in vivo and the broad host range transfer plasmid has been delivered in vivo to both P. aerugincsa and E. coli.

Results indicated that the infection of the bacterial cells with the phage lysates comprising the infectious virions containing a toxic agent was capable of killing the infected bacterial cells. Further, bacterial cell death was seen to be dose dependent such that higher M.O.I lead to increased cell death. Thus, the methods and compositions of the invention are useful as antimicrobial agents for treating pathogenic infections.

Lethality testing of the toxic agents and has revealed that doc, gef, chpBK and kicB are all bactericidal to E. coli. (See FIG. 4). Specifically, colonies were grown in liquid culture under conditions where the expression of the toxic proteins was repressed. following expression of the protein by induction with IPTG for 1 hour, cultures were plated out overnight onto agar lacking IPTG. The absence of colonies indicates the protein is lethal (see also Table 4 for Results). Constructs were transformed into E. coli and plated onto agar with or without 1 mM IPTG. Equal quantities of DNA (500 ng) were also transformed into P. aeruginosa, S. aureus and E. faecalis. Mock transformations were also performed with 'no DNA.'+ indicates greater than 100 colonies, – indicates no detectable colonies. Experiments were repeated at least two times with the same result. All agents were lethal to E. coli but only doc was toxic in all four.

TABLE 4

Assessment of the Toxic Proteins in E. coli, P. aeruginosa, S. aureus and E. faecalis using the Broad Host Range Plasmid.

| Construct | E. coli | E. coli + IPTG | P. aeruginosa | S. aureus | E. faecalis |
|---|---|---|---|---|---|
| Parent vector | + | + | + | + | + |
| doc | + | – | – | – | – |
| gef | + | – | + | + | + |

TABLE 4-continued

Assessment of the Toxic Proteins in E. coli, P. aeruginosa, S. aureus and E. faecalis using the Broad Host Range Plasmid.

| Construct | E. coli | E. coli + IPTG | P. aeruginosa | S. aureus | E. faecalis |
|---|---|---|---|---|---|
| chpBK | + | − | − | + | + |
| kicB | + | − | + | + | + |

As shown in FIG. 5, the growth of E. coli harboring a doc Expression plasmid was demonstrated to be inhibited when the expression of doc was induced by IPTG. Specifically, cells were grown overnight in LB at 32° C., diluted 1:100 into fresh LB medium and incubated at 32° C. for 180 min. The culture was then divided equally and incubated at 32° in the absence (○) or presence of 2 mM IPTG (○) which results in the expression of the lethal agent doc. Growth was calculated by spectrophotometric measurements with 1 ml samples at OD600.

Unlike traditional antibiotics which merely slow the growth of the bacteria, lethality testing of doc has shown that 99% cell death was achieved when cells were induced with IIPTG for 20 mm. A significant reduction (92% cell death) was also demonstrated when the cells were under no selective pressure to maintain the doc expression plasmid. Thus, the rapid killing of bacteria reduces the potential for selective pressure to give rise to resistant strains, which is important in eradicating multidrug resistant bacteria.

Low Resistance to Doc

In order to examine the frequency of resistance to doc, resistant mutants were isolated. The rationale was to select for spontaneous mutations and no mutagens were used. Following prolonged exposure to sublethal concentrations of 40 doc resistant E. coli clones were isolated. DNA isolated from these clones were tested by transformation to a doc-sensitive cell, however the presence of IPTG did not induce cell killing. This indicates that resistance is due to mutations or recombination events in the doc expression plasmid, suggesting that a chromosomal mutation of the doc target occurs at a very low frequency.

Toxicity to P. aeruginosa

Doc and chpBK have been demonstrated to be toxic to P. aeruginosa. Of particular note is that doc had a broad-spectrum activity in both Gram-negative (E. coli and P. aeruginosa) and Gram-positive (S. aureus and E. faecalis) bacteria (see Table 4, above). As seen in Table 4, the toxic agent doc killed all species of bacteria tested. Doc, gef, chpBK and kicB were all able to kill E. coli. chpBK killed E. coli and P. aeruginosa.

Development of a Bacteriophage Toxic Agent Delivery System

A toxic agent delivery system has been achieved for the use of a bacteriophage P1 system to package and deliver a Transfer plasmid (See FIGS. 6A and 6B) to E. coli and P. aeruginosa. FIG. 6A depicts the Transfer plasmid containing the essential signals for packaging (a pac site and a lytic replicon under the control of the P1 P53 promoter), a selectable marker for detection (bla, amicillin) and ColE1 origin of replication in E. Coli. FIG. 6B depicts the lytic replicon which comprises the C1 repressor-controlled P53 promoter antisense and genes kilA and repL. The kilA gene contains a 52% in frame deletion. P53 antisense is implicated in the stability of the P1 replicon. The methods of the invention are exemplified herein by two transfer plasmids capable of being efficiently packaged in P1 virions for delivery to pathogenic Gram-negative bacteria. Importantly, the delivery system is not under the constraints of superinfection exclusion (FIG. 7). In order to demonstrate delivery efficiency of the Transfer plasmid by the P1 Delivery System to E. coli, the following assay was performed. The E. coli P1 Cm clts100 lysogen carrying the transfer plasmid was induced by thermal induction to produce phage particles. Phage lysates were created with DNase and RNase and precipitated particles were resuspended in 50 mM Tris.Cl pH 7.5, 10 mM $MgSO_4$, 5 mM $CaCl_2$, 0.11% gelatin, E. coli C600 and E. coli P1 C600 target cells ($10^5$ CFU/ml, treated with 10 mM $MgSO_4$, 5 mM $CaCl_2$) were infected with each of the phage lysates. Following 30 min incubation at 30° C., infections were plated onto selection plates and antibiotic resistant colonies were scored. Values indicate number of antibiotic resistant colonies ± standard error, n=6.

Further, the phage-based delivery system is not blocked by a resident phage, such as P1 and lambda, or by compatible plasmids. This is important because analyses of environmental samples suggests that up to 40% of P. aeruginosa strains in the natural ecosystems (lake water, sediment, soil and sewage) contain DNA sequences homologous to phage genomes. The bacteriophage based system is useful to to transfer genetic information in vivo by delivery of a transfer plasmid expressing an antibiotic marker to E. coli and P. aeruginosa in a mouse peritonitis model of infection. Plasmid transfer was confirmed by restriction analysis and sequencing of the plasmid DNA re-isolated from bacteria recovered from the intraperitoneal space. Demonstration of transfer in vivo has also been obtained.

Develop Bacteriophage P1 Knockouts Able to Package Transfer Plasmid DNA but Unable to Incorporate P1 DNA One consideration of using unmodified phage as a delivery vehicle is the potential risk of lysogenic conversion. In order to develop a bacteriophage delivery vector which is capable of delivering a Transfer plasmid, to a target bacteria, but which is unable to deliver its own DNA to a target bacteria, a modified P1 phage was developed.

As shown in FIG. 8, the P1 prophage DNA has been modified to generate a pac site knockout. The disruption cassette contain a nutritional or antibiotic marker flanked by sequences homologous to the P1 prophage. the linear fragment was protected from exonuclease attach by the incorporation of phosphorothioate groups. A double crossover event between the in vitro-altered sequence and the P1 prophage resulted in deletion of the pac site and acquisition of the selectable marker. The function of this knockout serves to inhibit the ability of the p1 bacteriophage to package or transfer its own DNA to a target bacteria.

As shown in FIG. 9, the modified P1 was unable to transfer the chloramphenicol marker associated with its genome, suggesting that phage particles produced from the pac mutants lack phage DNA. The top panel of FIG. 9 shows the physical map of the P1 prophage and predicted P1 knockout following integration of the disruption cassette at the pac site. Arrows indicate location of the PCR primers used to verify the replacement of the P1 pac site with the S. cerevisiae TRP1 gene. The gels shown the products of the PCRs using P1 specific primers (1, 3, 5 and 6) and disruption cassette specific primers (2 and 4) to detect either the wild type P1 prophage r the P1 knockout. Primers 1 and 3 do not bind within the P1 sequences in the disruption cassette therefore PCR with primer 1+2 and 3+4 only detect a specific integration event which results in replacement of the pac site with the S. cerevisiae TRP 1 gene.

As a consequence of the pac site lying within the pacABC operon, the modified phage needed to be complemented in trans with the pacase enzyme. Construction of the pacABC complementing plasmid is shown in (FIG. 10 and Table 5).

TABLE 5

Construction of the pacABC complementing plasmid.

c1-pBSK
clts100-pBSK
Bof-pACYC184
pEDI-clts100-pBSI
C1pro-clts100-pBSK
clmut-clts100-pBSK
Bof-pEDI clts100-pACYC184
Bof-C1mut clts100-pACTC184
Bof-C1pro clts100-pACYC184
TpacABCT-Bof-pEDI clts100-pACYC184
TpacABCT-Bof-C1pro clts100-pACYC184
Tpr94pacABCT Bof-pEDI clts100-pACYC184 cl, cl repressor;
clts100, C1 repressor with temperature sensitive cl. 100 mutation;
Bof, modulator of C1 repressor;
pEDI, promoter;
c1pro, promoter with C1 operator sites Op99a and Op99b;
c1mut, promoter C1pro with mutated operator sites;
pacABC, genes encoding pacase enzyme;
T, transcirption terminatore;
Pr94, promoter with operator site Op94;
pBSK, E. coli vector pBluescript,
pSACYC184, E. coli cloning vector.

P1 pacABC were expressed from an early promoter Pr94. Two phage encoded proteins, C1 repressor and Bof modulator, were used to regulate expression from the Pr94 promoter. Although Bof alone does not bind to DNA, together with C1 it increased the efficiency of the repressor-operator interaction. The cl repressor has the c1ts 100 mutation and was therefore be temperature sensitive. This allowed the coordinated expression during the phage lytic cycle to the pacABC genes.

The complementation plasmid allowed P1 pac mutant to package the Transfer plasmid but not its own viral DNA. Complementation with the pacase enzymes did allow the P1 pac mutants to package the transfer plasmid, however a portion of the phage particles produced from the pac mutants contained P1 viral DNA. Analysis of the chloramphenicol resistant transductants indicated that the majority were unable to produce a second round of multiplication, suggesting that they were defective lysogens. The pac mutants appeared to have acquired a pac site, by recombination with the complementing plasmid, thereby enabling the mutants to package and deliver its own viral DNA.

Southern blot analysis verified that the pacABC genes on the complementing plasmid had been replaced with the ScTRP1 disrupted copy (FIG. 11). Specifically, the P1 mutant lysogens harboring the Transfer plasmid and pac ABC complementing plamsid were growth at 32C and diluted 1:100 into fresh medium every 16 hours. DAN was extracted on day 1, 2, 3, 4, and 5, digested with HindIII and probed with a ScTRP1 EcoR1-BamH1 fragment under high stringency conditions.

In order to prevent reconstruction of functional (pacABC pac enzyme by recombination events between the Transfer plasmid and the modified P1 phage genome, silent mutations were introduced into the complementing plasmid as shown in FIG. 12. Silent mutations in the complementing plasmid pac site lead to a defective pac site even if recombination occurred, and ensured that a defective pac site was be introduced into the P1 pac knockout (FIG. 12). The 162 bp pac site is sufficient to promote pac cleavage and P1 packaging. The positions of the hexanucleotide elements with the HEX4 and HEX3 domains are shown by open boxes. the IHF binding site, consensus sequence 5'-AATCAANNANTTA (SEQ ID NO:8), is indicated. Regulation of pac cleavage involves adenine methylation at 5'-GATC sites. Silent mutations introduced into the pac site are indicated by lower case letters.

In Vivo Delivery of Therapeutic Agents by P1 Virions

All five animal models listed in Table 6 are exemplified herein. LD50's have been established in the peritonitis models for E. coli and P. aeruginosa, and the doses required are high ($10^7$-$10^8$ bacterial cells/animal). Further, a cystic fibrosis model of pseudomonas infection in mice is used to demonstrate efficacy of the toxic agents and methods of the invention for treatment of opportunistic lung infection characteristic of this disease.

TABLE 6

Animal Models for Prokaryotic Gene Therapy

| Animal Model | LD50 |
|---|---|
| E. coli peritonitis | $3 \times 10^8$ cfu |
| Pseudomonas peritonitis | $1 \times 10^7$ cfu |
| Pseudomonas-burn in mice | <10 cfu |
| Pseudomonas-burn in rats | $1 \times 10^8$ cfu |
| Pseudomonas in neutopenic mice | $2 \times 10^3$ cfu |

Peritonitis Models

A Transfer plasmid of the invention has been delivered with the P1 delivery system to E. coli and Pseudomonas in vivo in the mouse peritonitis model. Transfer was confirmed by re-isolation of the plasmid from bacteria recovered from the intraperitoneal space, and by restriction analysis of the recovered plasmid. Results demonstrate that the delivery vehicles of the invention are capable of delivering the toxic agents of the invention to a bacterial target without toxicity to the infected subject.

The immune response to the phage and phage clearance kinetics in vivo has also been examined. Results indicate that single injections of $2 \times 10^9$ lysogen forming units (lfu) of P1 phage per mouse resulted in the production of anti-phage antibodies in 8-14 days. Two groups of 4 mice were injected intraperitoneally (IP) with $2 \times 10^9$ lfu of long circulating P1 phage. Peripheral blood was sampled by tail clip at 1, 4, 8 and 24 hours post injection and titered with E. coli C600 target cells. The previously phage-challenged group had been injected IP with an equivalent dose of the same phage preparation 18 days prior to this experiment. The pre-immune group had no prior treatments. This resulted in rapid clearing of the phage in vivo (FIG. 13). However, for human therapeutic considerations, many infected subjects (especially for pseudomonas) will be immunocompromised and incapable of generating strong immune responses. Accordingly, the Therapeutics and compositions of the invention may be particularly beneficial for such human subjects.

In addition, a long-circulating variant of P1 was selected by passage through mice that results in greater than 200 times more phage remaining in circulation at 24 and 30 hours after injection (FIG. 14). Groups of 6 mice were injected IP with either $5 \times 10^8$ lfu P1 phage or $5 \times 10^8$ lfu long-circulating P1 phage. Peripheral blood was sampled by tail clip at 1, 6, 24, and 30 hours post injection and titered with *E. coli* C600 target cells. The number of viable phage remaining per ml of blood at each time-point is indicated in FIG. 14. The fold improvement in persistence in the circulation is given in the last column of the table (lfu long-circulating P1 phage/lfu original P1 phage). Accordingly, use of the long-circulating P1 is within the scope of the invention. Such variant may be particularly preferable when increased concentrations of phage are desired in the circulation of an infected subject. For example, it may be desired in the case that the subject has a pathogen or bacterial infection in the blood.

Embryonated Hen Egg Model

In order to demonstrate efficacy of the toxic agent delivered by the P1 delivery vehicle, an embryonated hen egg model of infection has been modified from published protocols. Superficially, the hen egg model of Hartl, A., et al., (1997, "*Pseudomonas aeruginosa* infection in embryonated hen's eggs" Arzneim.-Forsch. 47(II): 1061-1064), was modified in the manner in which the eggs were incubated and the shells opened and administration was performed. Briefly, eggs were incubated in the vertical position, wide pole up, with automatic turning in a 90 degree arc every 4 h. Shells were opened on the wide pole end, by reinforcing the shell with adhesive tape and cutting a round hole with a scissors through the tape and shell (opening diameter approx. 1 cm). The underlying shell membrane was moistened with sterile water, then partially removed by tearing off a 1 $cm^2$ portion with a sterile forceps, which exposes the transparent chorioallantoic membrane (CAM). The shell was sealed against moisture loss with more adhesive tape and incubation continued for 18-24 h. Viability was assessed at that time by candling (observing the embryo by holding the egg in front of a bright light source). Observation of spontaneous movement was evidence of viability. Viable eggs were inoculated by pipeting bacterial suspensions onto the CAM. Therapeutic agents were pipeted onto the CAM or injected through the shell at other locations by syringe. Openings in the shell were resealed with tape, incubation continued, and viability was scored at intervals by candling as above. Bacteria and phage were introduced into the egg through an opening made in the shell, which was then sealed and gestation continued.

An embryonated hen egg model was established, as above, which harbors a variety of advantages as an in vivo system. Specifically, the egg model required very low LD50 (<10 cfu/egg for *P. aeruginosa* and >50 cfu/egg for virulent strains of *E. coli*), the egg model is also rapid, self contained and provides for an immature immune system. Human clinical isolates of *E. coli* and *P. aeruginosa* (PA01) consistently produce lethal infections in this model at very low doses of bacteria (100-1000 cells) allowing demonstration of the therapeutic agents. These tests show efficacy for the toxic agent such as doc in vivo.

In order to demonstrate the ability of the delivery vehicles of the invention to deliver a Transfer plasmid in vivo, a Transfer plasmid carrying a kanamycin resistance gene was delivered to *E. coli* and *P. aeruginosa* in vivo, in mice and in embryonated hen eggs. Results indicated that delivery of toxic agent by the P1 system is successful in vivo.

*P. aeruginosa* Hen Egg Model

In vivo plasmid transfer in chicken embryos: The Transfer plasmid pBHR was delivered to bacterial cells by P1 phage in vivo in using embryonated hen eggs, Specifically, groups of six embryonated hen eggs were inoculated via the chorioallantoic membrane on the tenth day of gestation with the bacteria and phage indicated. P1 lysogen which harbors pDoc, a transfer plasmid which encodes the doc gene. This phage preparation was a mixture of particles containing either p1 DNA or pDoc. Phage lysates were approximately a ratio of 99:1 P1 containing phage particles to pDoc containing particles.

Results demonstrated increased survival of eggs when P1 or P1-pDoc lysates are added immediately after inoculation with human clinical *P. aeruginosa* PA01 (FIG. 15).

*E. coli* Hen Egg Model:

A human clinical *E. coli* isolate which is refractory to transduction with P1 DNA has been found to produce a lethal infection in embryonated hen eggs. This isolate was designated EC-4, and is important for two reasons. First, since this strain cannot form a stable P1 lysogen, killing of EC-4 cells by doc-carrying phage preparations demonstrated the lethal activity of the toxic agent doc.

Specifically, P1-pDoc lysates killed EC-4 *E. coli* in vitro more efficiently than P1-pBHR phage alone (see FIG. 16). Specifically, EC-4 cells (500 cfu) were treated with phage containing toxic agent doc (P 1-pDoc) or control transfer plasmid pBHR (P1-pBHR) at the multiplicities of infection (MOI) shown in FIG. 16, plated on non-selected media and counted as a percent of live cells treated with buffer alone. Results indicate that the toxic agent doc was able to render *E. coli* EC-4 less fit and increase killing of the pathogenic bacteria. Additionally, *E coli*. killing was confirmed in vitro: at a P1 MOI of 500-700, doc was able to kill the *E. coli* at a MOI 5-7, i.e. 1% of the total P1 particles (FIG. 16).

Second, existence of this strain in a random sample of clinical isolates from local hospital demonstrated that there were pathogenic bacterial strains in the human population which were resistant to lytic phage therapy but susceptible to Toxic agent phage delivery system. Specifically, as shown in Table 7, below three clinical *E. coli* isolates were compared for their ability to be transduced with P1 DNA (as indicated by acquisition of chloramphenicol resistance) and transduced with transfer plasmid DNA (as indicated by acquisition of kanamycin resistance) relative to laboratory *E. coli* strain C600. All three clinical isolates were transduced with the Transfer plasmid, but only two became lysogenic with P1. These results indicate that a phage resistant mechanism was preventing transduction of P1 viral DNA was unable to prevent delivery of the transfer plasmid to EC-4 cells.

TABLE 7

Clinical Isolates - susceptibility to P1 Transduction.

| *E. coli* | Transduction with P1 DNA | Transduction with Transfer Plasmid DNA | |
|---|---|---|---|
| C600 (lab strain) | $1.9 \times 10^7$ lfu | $7.7 \times 10^5$ lfu | C600 in transduced with P1 DNA and the transfer plasmid |
| EC-1 (Human) | $2.0 \times 10^7$ lfu | $8.5 \times 10^6$ lfu | EC-1 in transduced with P1 DNA and the transfer plasmid |
| EC-2 (Human) | $9 \times 10^6$ lfu | $7.5 \times 10^6$ lfu | EC-2 in transduced with P1 DNA and the transfer plasmid |
| EC-4 (Human) | 0 | $2.8 \times 10^6$ lfu | EC-4 in transduced with P1 DNA and the transfer plasmid |

Further, an infection with $2 \times 10^3$ EC-4 cells was cured in eggs by a P1-pDoc lysate treatment given immediately after inoculation with the bacteria at a P1 MOI of 700-800 (doc containing virions were 1% of total phage particles) (FIG. 17). Specifically, groups of seven embryonated hen eggs were inoculated via the chorioallantoic membrane on the tenth day of gestation with the bacteria and phage indicated. P1-pDoc phage was produced from a P1 lysogen which harbors pDoc, a transfer plasmid encodes the doc gene or control transfer plasmid pBHR. This phage preparation was a mixture of virions containing either P1 DNA or pDoc. Phage lysates were approximately a ratio of 99:1 P1 containing phage particles to pDoc containing particles. These results indicate that a pathogenic infection may be eradicated by a therapeutic of the invention, such as doc via a P1 delivery vehicle.

Mammalian Animal Models

Three mouse and rat models are used to demonstrate the efficacy of the Toxic agents of the invention. Each models uses an immunocompromised animal, which is then followed by a bacterial challenge. The models differ in the route of bacterial challenge and the means of producing the immune impairment.

In two models, immune impairment is produced in a burn model. Specifically, a burn of 10-20% total body surface area in humans or other animals results in a period of immune impairment, involving nearly all branches of the immune system, which lasts from 10-14 days. Two burn models, well documented in the literature (see, e.g., J. P. Waymack, et al, 1988, "An evaluation of cyclophosphamide as an immunomodulator in multiple septic animal models" J. Burns and Clinical Rehabilitation 9(3):271-274; see also Stieritz, D. D. and Holder, I. A., 1975, "Experimental studies of the pathogenesis of infections due to *Pseudomonas aeruginosa*: Description of a burned mouse model" J. Infect. Dis. 131(6): 688-691) for experimental infections with *Pseudomonas aeruginosa*, are used to demonstrate the effectiveness of a toxic agent therapeutic against the types of infections which occur with this type of wound.

The third model utilizes the biological modulator cyclophosphamide to produce an immunocompromised state (leukopenia), in which endogenous microflora of the intestinal tract can invade the body cavity and cause sepsis. This type of sepsis has been documented in human patients with immunodeficiency (see, Furuya, et al, 1993, "Mortality rates amongst mice with endogenous septicemia caused by *Pseudomonas aeruginosa* isolates from various sources." J. Medical Microbiology 39: 141-146; Woods, et al, 1997, "Correlation of *Pseudomonas aeruginosa* virulence factros from clinical and environmental isolates with pathogenicity in the neutropenic mouse" Can. J. Microbiol. 43: 541-551).

Model 1: Adult Mice, Dorsal Burn, Wound Surface Bacterial Challenge

The first model of use is that of Stieritz, D. D. and Holder, I. A. (1975, J. Infect. Dis. 131(6): 688-691); also see Neely, A. N. and Holder, I. A., 1996, "A murine model with aspects of clinical relevance for the study of antibiotic-induced endotoxin release in septic hosts. J. Endotoxin Research 3: 229-235.). Young adult female mice, 22-25 g, ICR strain (or possibly Balb/c, CD1, C3HEB/FeJ, C3H/HeJ, C57BL/6, DBA/2, A/J, CBA, C3H/HeN) are anesthetized with pentobarbitol and shaved of dorsal hair. A heat resistant plastic card with a 1×1.5 inch opening is placed on the shaved back, 0.5 ml ethanol pipetted onto the exposed skin and ignited for a 10 second burn. The flame is extinguished, and the mouse given 1-2 ml saline via intraperitoneal (IP) injection as fluid replacement. This procedure produces a non-lethal, partial thickness burn covering 12-15% of the body surface area of a 22-25 g mouse (Neely and Holder, 1996, supra). One hour after the burn, and after mice have received analgesia (buprenorphine 2 mg/kg, IM), a small inocula of bacteria (100 cfu *P. aeruginosa*) in 0.1 ml saline is injected subcutaneously into the wound. Toxic agent treatment agent or placebo is administered either simultaneously to the same site (also 0.1 ml in saline) or by IP injection (up to 0.5 ml in saline) 1 hour after or shortly before challenge. Animals are observed for sepsis and medicated for pain (buprenorphine 2 mg/kg, IM) at intervals not exceeding 12 h. Normal diet and water is provided ad libitum. Mortality is expected in untreated burned groups within approximately 48 h. Blood samples (10-25 ul) may be taken at 12-24 h intervals by tail bleed to monitor bacterial load. Blood and organs are collected at time of death or euthanasia, to monitor bacterial load and confirm death from *P. aeruginosa* sepsis or clearance of infection in treated animals.

Model 2: Adult Rat, Dorsal Burn, IP or Wound Surface Bacterial Challenge

The second model is that of Waymack et al. (J. P. Waymack, G. D. Warden, J. W. Alexander, P. M. and S. Gonce., 1988, "An evaluation of cyclophosphamide as an immunomodulator in multiple septic animal models". J. Burns and Clinical Rehabilitation 9(3):271-274.). Young male Lewis rats (100-125 g) are anesthetized by IP pentobarbitol injection (~40 mg/kg) and shaved of dorsal hair. The animal is pressed against a heat resistant template that exposes the shaved area (20% of the total body surface area). This template is immersed in a 95° C. waterbath for 10 seconds. After removal from the waterbath, the animals receive 5-10 ml Ringer's Lactate solution by IP injection for fluid maintenance therapy (approximately one half blood volume is recommended) and buprenorphine for analgesia (0.1-0.5 mg/kg, every 12 h). This injury is reported to be a full-thickness burn resulting in zero mortality in the absence of further injury. A 50% lethal dose bacterial challenge ($1 \times 10^8$ cfu *P. aeruginosa* in 0.5 ml saline) is introduced by IP injection on day 4 post-burn or by painting the bacterial suspension on the wound on day 1 post-burn. The IP infection route is reported to produce sepsis within 24 h (i.e. day 5 post-burn) with all deaths occurring by day 12 post-burn. Therefore, an IP injection demonstration may be terminated on day 12 post-burn. Painting of *Pseudomonas* on the burn is reported to result in sepsis 7-8 days after inoculation (day 8-9 post-burn), and survival rates are stable by day 20. Euthanasia of animals subjected to this regimen will be on day 21 post-burn. Normal diet and water will be provided ad libitum. Some animals are treatment with the therapeutic of the invention (P1 phage comprising a Transfer plasmid encoding a toxic agent) which is administered topically to the burn region or by IP injection. Blood samples (50 100 ul) may be taken by retro-orbital bleed of pentobarbitol anesthetized rats at intervals of 12-24 h to monitor bacterial load. Blood and organs are collected at time of death or euthanasia, also to monitor bacterial load and confirm death from *P. aeruginosa* sepsis.

Model 3: Adult Mouse, Antibiotic and Cyclophosphamide Injections, Oral Bacterial Challenge This is the model of endogenous septicemia of Furuya et al. (Furuya, N., Hirakata, Y., Tomono, K., Matsumoto, T., Tateda, K., Kaku, M., and Yamaguchi, K., 1993, "Mortality rates amongst mice with endogenous septicemia caused by *Pseudomonas aeruginosa* isolates from various sources." J. Medical Microbiology 39: 141-146). Mice weighing 20-25 g are housed in a sterile environment (e.g., in an isolator) and given sterile diet and water. IP injections of sodium ampicillin (200 mg/kg) are given on days 1 and 2 to disturb normal intestinal flora and aid colonization by P. aeruginosa. Cyclophosphamide is injected IP (250 mg/kg) on days 6 and 9. This dose induces leukopenia without lethality in the absence of infection. The bacteria are administered to the mice in their drinking water on days 2-4. Treatment with therapeutic of the invention (P1 phage comprising a Transfer plasmid encoding a toxic agent) is started on day 9, and is administered by IP injection. Fecal pellets are be collected before bacterial challenge and at intervals throughout the infection to monitor for the absence and presence of P. aeruginosa. The onset of sepsis is expected 24-48 h after the second dose of cyclophosphamide (day 11), and approximately 80% mortality is expected by day 14. Signs of distress in the animals are treated with buprenorphine (2 mg/kg, twice daily or as needed). Blood samples obtained by tail bleed may also be taken at 12-24 h intervals after day 4. Alternatively, the ampicillin injections can be avoided by introducing the bacteria by IP injection the day after the final cyclophosphamide injection (Woods, D. E., Lam, J. S., Paranchych, D. P., Speert, D. P., Campbell, M., and Godfrey, A. J., 1997, "Correlation of *Pseudomonas aeruginosa* virulence factros from clinical and environmental isolates with pathogenicity in the neutropenic mouse. Can. J. Microbiol. 43:541-551).

TABLE 8

Therapeutic formulations in the following format used in the mouse models:

| Group | Challenge | Phagemid treatment | Approximate # of survivors |
|---|---|---|---|
| 1 | Burn or cyclophosphamide (cyc) | 1000 × moi agent 1 | 6/6 |
| 2 | Burn or cyc | 1000 × moi agent 2 | 6/6 |
| 3-8 | Burn or cyc | 1000 × moi agent (n) | 6/6 |
| 9 | Burn or cyc + $LD_{100}$ pseudomonas | None | 0/6 |
| 10 | Burn or cyc + $LD_{100}$ pseudomonas | 1000 × moi agent 1 | 0/6 6/6 |
| 11 | Burn or cyc + $LD_{100}$ pseudomonas | 1000 × moi agent 2 | 0/6 6/6 |
| 12-17 | Burn or cyc + $LD_{100}$ pseudomonas | 1000 × moi agent 3 | 0/6 6/6 |

Total: up to 112 mice/model × 2 models = 224 mice

TABLE 9

A dose response demonstration is performed as follows:

| Group | Challenge | Phagemid treatment | Approximate # of survivors |
|---|---|---|---|
| 1 | Burn or cyclophosphamide (cyc) | 1000 × moi | 6/6 |
| 2 | Burn or cyc + $LD_{100}$ pseudomonas | None | 0/6 |
| 3 | Burn or cyc + $LD_{100}$ pseudomonas | 1000 × moi | 0/6 6/6 |
| 4 | Burn or cyc + $LD_{100}$ pseudomonas | 100 × moi | 0/6 6/6 |
| 5 | Burn or cyc + $LD_{100}$ pseudomonas | 10 × moi | 0/6 6/6 |
| 6 | Burn or cyc + $LD_{100}$ pseudomonas | 1 × moi | 0/6 6/6 |

Total: up to 36 mice/model/agent × 8 agents × 2 models = 576 mice

TABLE 10

Therapeutic formulations in the following format are used in the rat models:

| Group | Challenge | Phagemid treatment | Approximate # of survivors |
|---|---|---|---|
| 1 | Burn | 1000 × moi | 6/6 |
| 2 | Burn + $LD_{100}$ pseudomonas | None | 0/6 |
| 3 | Burn + $LD_{100}$ pseudomonas | 1000 × moi | 0/6 6/6 |
| 4 | Burn + $LD_{100}$ pseudomonas | 100 × moi | 0/6 6/6 |
| 5 | Burn + $LD_{100}$ pseudomonas | 10 × moi | 0/6 6/6 |
| 6 | Burn + $LD_{100}$ pseudomonas | 1 × moi | 0/6 6/6 |

Total: up to 36 rats/agent × up to 8 agents = 278 rats

Results of animal demonstrations indicate that the phage therapeutics comprising a toxic agent of the invention, is suited to treat bacterial infections of a subject. Other animal models known in the art are within the scope of the invention, including but not limited to models using calves, pigs, lambs, guinea pig, rabbits, etc. In a preferred aspect of the invention, the subject in need of a therapeutic of the invention is a mammal with a burn injury.

Treatment of Opportunistic Infections in a Murine Model of Cystic Fibrosis

The toxic agents of the invention are useful for the treatment of pathogenic infection such as infections associated with cystic fibrosis. As demonstration of the utility of the invention, a mouse model of pseudomonas respiratory infection is used which mimics the type of infection seen in human Cystic Fibrosis (CF) patients. This model uses adult (6-8 week old) mice which carry the DF508 mutation in the cftr gene (C57BL/6 DF508 mice) and their wild type counterparts (C57BL/6 mice), or BALB/c adult mice without cftr mutations. The DF508 mutation is one of the most common mutations found in human CF patients, and the C57BL/6 DF508 mice have many symptoms similar to humans with this disease. After weaning, DF508 cftr homozygous mutants must be maintained on a liquid diet of Peptamin (Clintec Nutrition Co., Deerfield, Mich.) and water containing golytely (Braintree Laboratories, Braintree, Mass.) in order to prevent fatal bowel obstructions which are common in these mice due to their cftr mutation (see Zaidi, T. S., et al, 1999 "Cystic fibrosis transmembrane conductance regulator-mediated corneal epithelial cell ingestion of Pseudomonas aeruginosa is a key component in the pathogenesis of experimental murine keratitis" Infection and Immunity 67(3): 1481-1492). BALB/c mice can also be used if C57BL/6 DF508 mice are not available.

The experimental procedure is as follows (see e.g., Pier, G. B. et al., 1996, "Role of mutant CFTR in hypersusceptibility of cystic fibrosis patients to lung infections" Science 271: 64-67). Adult mice are anesthetized by intraperitoneal injection of a freshly prepared mixture of ketamine hydrochloride (65 mg/kg) and xylazine (13 mg/kg). Then with mice are held in an upright position, and 10 ul of a bacterial suspension is placed in each nostril (20 ul total). Mice are allowed to regain consciousness and then either observed for survival for up to 72 hours, or, sacrificed by $CO_2$ overdose at various time periods up to 24 hours after infection for determination of bacterial loads in various tissues, especially the lungs. Anesthesia is a necessary part of the infection procedure. Unanesthetized mice fail to aspirate the inoculum efficiently and do not become infected. Therapeutic phage comprising one or more toxic agents of the invention are administered, for example, intranasally, intravenously, or intraperitoneally. Mice administered the Therapeutic of the invention survive longer than the untreated control mice. Accordingly, the toxic agents of the invention may be delivered to a subject harboring a pathogenic (e.g., bacterial) infection for the purpose of ameliorating or eradicating the infection.

8. Example: Construction & Characterization of Sof Sense RNA as a Toxic Agent

In order to demonstrate that a toxic agent may be delivered and expressed using a ribozyme cassette, the inventors have engineered a toxic agent directed against an essential molecule called Sof, and delivered the toxic agent in a ribozyme cassette to bacterial cells to cause the death of the bacterial cells.

As described herein above, a toxic agent may be a molecule which is designed to target an essential molecule of a pathogen or selected cell. An example of an essential antisense molecule for bacteria is Sof. Sof is an antisense antidote for a chromosomally encoded toxin called gef. Sof normally acts to regulate the levels of gef in the pathogen, and thus allows the cell to survive in the presence of gef. The inventors of the present invention have designed sense molecules which are complementary to Sof. The sense molecules against Sof acted to inhibit the ability of Sof to regulate gef, and thus caused toxicity in the pathogen by allowing the endogenous gef levels to become toxic to the bacteria.

Specifically, Sof sense was constructed into a triple ribozyme cassette (with 5' and 3' cis-acting ribozymes). The ribozyme cassette containing the Sof sense toxic agent was linked to the LEASHI promoter. The nucleic acids encoding the ribozyme cassette were then used to transform *E. coli*. Bacterial cells were plated onto LB Amp+IPTG. Plates were incubated overnight at 37° C. Plates were then scored for the presence of transformants, size of colonies, growth rate, and morphological differences.

Results of these studies indicated that expression of the Sof sense molecules from the ribozyme cassette lead to toxic effects in the targeted bacteria.

9. Example: Ribozymes and Ribozyme Cassettes

The ribozyme cassettes which are particularly useful in the methods of the invention include but are not limited to the following:

pClip (the genetic element described in FIG. 19) is a modification of pBluescript, wherein the cassette shown is dropped into the Not I site in pBluescript. The toxic agent or trans-acting ribozyme is constructed into the Bgl II site (TGCTCT). Liberation of internal ribozymes or toxic agents from pClip results in a distribution of the toxic agent or ribozyme(s) to approximately 20% nuclear and 80% cytoplasmic, when delivered to a eukaryotic cell. pClip is also used to target prokaryotic cells.

A second ribozyme cassette/vector that is useful in connection with the methods of the invention is pChop. pChop is modified from pClip to convey a more efficient and effective liberation of the internal trans-acting ribozymes or toxic agents. The pChop ribozyme cassette is diagramed in FIG. 20. Liberation of internal catalytic core ribozymes from pChop increases localization to the nucleus when delivered to a eukaryotic cell.

A third ribozyme cassette that was useful in connection with the methods of the invention is pSnip. The pSnip multi-ribozyme is constructed by engineering the pClip cassette 5' to pChop. In addition, the pSnip multi-ribozyme contains catalytic core sequences with two trans-acting ribozymes or toxic agents in each cassette. Each pair of trans-acting ribozymes or toxic agents is linked by a short spacer and stabilized by a hairpin loop located 3' to the pair. FIG. 21 diagrams the schematic of the pSnip cassette.

A trans-acting ribozyme, or antisense toxic agent is synthesized as reverse complementary overlapping oligodeoxynucleotides, which are designed in such a way that when annealed they form single stranded ends identical to those produced by digestion with the restriction endonuclease contained with the region between the two cis-acting ribozymes. In this particular example the restriction endonuclease recognition site is that recognized by Bgl II. Essentially any RNA can be targeted: specificity is conferred by selecting sequences for the ribozyme that are reverse and complementary to sequences flanking the chosen cleavage site in the targeted RNA molecule. The toxic agent(s) or trans-acting ribozymes are then cloned into the cloning region (polylinker) within the double ribozyme cassette to produce the targeted toxic agent or ribozyme. Trans-acting ribozymes targeted to prokaryotic sequences have been constructed including, but not limited to, *Escherichia coli*: secA (EcosecA, AE000119 U00096), gene X (EcosecA, AE000119 U00096) ftsZ (AE000119; U00096), dnaG (AE000388 U00096), rpoA (AE000407 U00096) and tRNA-asp (×14007), *Streptomyces lividins* secA (Z50195), *Enterococcus faecalis*, ftsZ (U94707) *Pseudomonas putida*, dnaG (U85774), *Streptomyces coelicolor* rpoA (X92107), *Staphylococcus warneri* tRNA-Asp (X66089 S42075), *Staphlococcus* RNA III.

The utility of the design using eukaryotic sequences has also been evaluated; a) repetitive B2 transcripts (B2); b) RNA polymerase I (polI); c) Hepatitis B virus (HBV); d) Sonic Hedgehog (SH); e) Human *Papillomavirus* E6/E7 protein (HPV); f) RNA polymerase II (polII); g) Insulin-like Growth Factor 1 (IGF1); h) retinoblastoma protein (RB); i) and j) Multicatalytic Proteinase alpha-subunits C3 and C9 (C3 and C9, respectively); k) telomerase (tel); l) Transforming growth factor beta (TGFβ); m) catalase (CAT); n) Peroxisome proliferation associated receptor (PpaRα); and o) Cytochrome $P_{450}$ 1E1 (p4501E1); KiSS-1, NudC, Androgen Receptor, and SF-1 transcription factor. Target RNAs (with locus names and accession numbers) as well as the selected target sites are presented (Table 11).

TABLE 11

Summary of Targeted RNAs and Target Sites

| Target RNA | EMBL Locus | Accession | Target Site | Functional Testing | |
|---|---|---|---|---|---|
| | | | | in vitro | in vivo |
| pol II | HSRNAP14K | Z27113 | $GTC_{83}$ | ND | ND |
| HBV | XXHEPAV | X02496 | $GTC_{438}$ | IP | + |
| HBV | | X04615 | $GTT_{1944}$ | + | + |
| HBV | | X02496 | $GTT_{1946}$ | + | + |
| HCV | | M62321.1 | $GTC_{325}$ | + | + |
| RB | MUSP105RB | M26391 | $GTC_{264}$ | + | + |
| IGF1 | HUMIGF1B | M37484 | $GTC_{185}$ | ND | ND |
| SH | MMEVX1 | X54239 | $GTC_{558}$ | IP | IP |
| Pol I | MUSRPA40 | D31966 | $GTC_{458}$ | + | + |
| HPV | PPH16 | K02718 (SEQ ID NO:19) | $GTT_{108}$ | IP | + |
| C3 | RATC3AA | J02897 | $GTT_{22}$ | + | + |
| C9 | RNPTSC9 | X533304 | $GTC_{101}$ | + | + |
| B2 | B2-Consensus | ## | $GTT_{24}$ | + | + |
| Tel | MMU33831 | U33831 | $CTA_{63}$ | ND | ND |

TABLE 12

Sites Identified on HPV E6/E7 Target RNAs by Library Selection

| HPV strains | GenBank Accession Number | Nucleotide Triplet and Position |
|---|---|---|
| HPV11 | M14119 | CTC121 |
| HPV16 | K02718 (SEQ ID NO:19) | TTC110 |
| HPV18 | X05015 | ATC123 |
| HPV11 | M14119 | ATA443 |
| HPV16 | K02718 (SEQ ID NO:19) | GTC437 |
| HPV18 | X05015 | ATC444 |
| HPV11 | M14119 | GTC507 |
| HPV16 | K02718 (SEQ ID NO:19) | GTC506 |
| HPV18 | X05015 | ATA507 |

TABLE 13

Sites on HBV RNA Identified by Library Selection Nucleotide Triplet and Site

| Sites on HBV RNA | GenBank Accession Number |
|---|---|
| GTC1473 | X02496 |
| CTC1534 | X02496 |
| CTC1532 | X04615, +* |
| ATC1842 | X02496 |
| ATC1840 | X04615, +* |
| GTT1946 | X02496 |
| GTT1944 | X04615, +* |
| CTC1950 | X02496 |
| CTC1948 | X04615, +# |
| TTC1948 | X75663, X75658 |

*Includes but is not limited to X75664, X75657, X75665, X75663 and X75658.
Includes but is not limited to X75664, X75657, X75656, and X75665.

10. Example: Delivery and In Vivo Testing

Biologic Delivery

The toxic agents and/or ribozymes of the present invention may be delivered by a wide variety of viral vectors and bacteriophage as described herein, and exemplified herein above.

In one embodiment of the invention, a toxic agent is encoded in a Transfer plasmid, and is used in connection with a P1 bacteriophage delivery system. Such Transfer plasmid preferably contains 1) an origin or replication 2) selectable marker 3) P1 PAC site and PAC ABC genes 4) P1 lytic replicon 5) nucleic acids encoding one or more toxic agents of the invention. In a preferred embodiment of the invention, the bacteriophage P1 prophage (P1 plasmid) is engineered such that viral DNA can not be packaged into virions, such as, for example, by deletion of the PAC site from the P1 plasmid.

In another embodiment, the toxic agents and/or ribozymes may be delivered via a plasmid encoding the toxic agents and/or ribozymes, a plasmid origin of replication, a selectable marker for plasmid maintenance, the minimal lambda origin of replication, and cos sites, which are required for packaging of DNA into lambda virions. This plasmid is maintained in a lambda lysogen that is defective in integration/excision and recombination functions. The defective lysogen provides all of the replication factors needed to activate the lambda origin of replication on the plasmid and all of the structural components needed to form mature virions; however, the lysogen is not able to replicate and package its own DNA into the virions. The lysogen also carries the $cI^{857}$ temperature-sensitive repressor mutation. Induction of the lysogen by temperature shift to 42° C. or by other means, such as exposure to 5J/m2 of ultraviolet radiation will mobilize the plasmid and result in its replication and packaging into lambda virions. The virions can then be harvested, purified free of E. coli proteins and be used to deliver the toxic agents and/or ribozyme gene(s) to E. coli. Similar methods are performed for Pseudomonas aerugunosa in order to deliver a toxic agent and/or ribozyme to P. aerugunosa.

Abiologic Delivery

Abiologic delivery of the toxic agent and/or ribozymes is accomplished with constructs that have been engineered to be expressed within the targeted tissue or pathogen. Briefly, the genetic element containing the promoter and the toxic agent and/or ribozyme(s) are complexed with cationic liposomes (Lipofectamine—Gibco BRL) in a 1:10 ratio and are introduced into test animals by either single or multiple injection of 0.2 ml total volume nucleic acid-liposome mixture.

Prophylactic Administration and Prevention of a Cute Bacterial Infection

Following the demonstration that toxic agents and/or ribozymes of the present invention have an in vitro biological activity (either directly on bacterial cultures or in an infectious tissue culture cell assay system), the effectiveness of the toxic agents and/or ribozymes, is shown in in vivo model systems, e.g., as described above. To demonstrate the efficacy of toxic agents and/or ribozymes of the invention in vivo, experimental animal model systems are utilized, such as these described herein. For an initial demonstration of the efficacy of the toxic agents and/or ribozymes in vivo, mice are infected with a microbial pathogen which has previously been shown to be sensitive to the toxic agents and/or ribozymes construct(s) and the effect of toxic agents and/or ribozymes administered in vivo is determined. In the first series of in vivo trials, one determines the effectiveness of toxic agents and/or ribozymes at preventing an acute infection in a murine model system when the toxic agents and/or ribozymes is added directly to the microbe prior to administration in vivo.

The next series of trials demonstrates that the administration of toxic agents and/or ribozymes after infection is effective at preventing an acute bacterial infections. In addition to the clinical status of infected mice, tissues obtained at necropsy are examined histologically and the presence of replicating microorganism in tissue samples is determined by standard methodology. Animals can be infected by various routes (systemic and/or mucosal) and the toxic agents and/or ribozymes are delivered over time after infection by systemic, mucosal, or topical routes. Both abiologic as well as biological delivery of the toxic agents and/or ribozymes is used. The demonstration of a positive effect of the toxic agents and/or ribozymes in controlled experimental model system provides compelling evidence for the efficacy of the preparation and determines whether or not the preparation warrants evaluation under conditions of standard clinical trials.

Throughout this application various publications are referenced. The disclosures of these publications in their entireties are hereby incorporated by reference into this application in order to more fully describe the state of the art to which this invention pertains.

What is claimed is:

1. A recombinant nucleic acid comprising a tissue-specific promoter operably linked to a ribozyme cassette comprising one or more autocatalytically cleaving ribozyme sequences and a trans-acting cleaving ribozyme sequence comprising a target RNA-specific sequence that cleaves an RNA encoded by SEQ ID NO:19 at a nucleotide selected from the group consisting of nucleotide number 108, nucleotide number 437, and nucleotide number 506.

2. The recombinant nucleic acid of claim 1, wherein the target RNA-specific sequence cleaves an RNA encoded by SEQ ID NO:19 at nucleotide number 108.

3. The recombinant nucleic acid of claim 1, wherein the target RNA-specific sequence cleaves an RNA encoded by SEQ ID NO:19 at nucleotide number 437.

4. The recombinant nucleic acid of claim 1, wherein the target RNA-specific sequence cleaves an RNA encoded by SEQ ID NO:19 at nucleotide number 506.

5. The recombinant nucleic acid of claim 1, wherein said nucleic acid comprises two autocatalytically cleaving ribozyme sequences.

6. The recombinant nucleic acid of claim 1, wherein said tissue-specific promoter is a keratin promoter.

7. The recombinant nucleic acid of claim 1, wherein said nucleic acid is contained in a viral vector.

8. The recombinant nucleic acid of claim 7, wherein said viral vector is a retroviral vector.

9. The recombinant nucleic acid of claim 7, wherein said viral vector is an adenoviral vector.

10. The recombinant nucleic acid of claim 7, wherein said viral vector is an adenovirus-associated viral vector.

* * * * *

UNITED STATES PATENT AND TRADEMARK OFFICE
CERTIFICATE OF CORRECTION

PATENT NO.       : 7,575,918 B2                                      Page 1 of 1
APPLICATION NO.  : 10/935962
DATED            : August 18, 2009
INVENTOR(S)      : James S. Norris It is certified that error appears in the above-identified patent and that said Letters Patent is hereby corrected as shown below:

Title Page, item (54); Title of Invention, before "Ribozymes" please insert --Toxic Agents And--;

Column 1, line 2, before "Ribozymes" please insert --Toxic Agents And--.

Signed and Sealed this

Seventeenth Day of November, 2009

David J. Kappos
*Director of the United States Patent and Trademark Office*